(12) United States Patent
Ellison

(10) Patent No.: US 11,328,822 B2
(45) Date of Patent: May 10, 2022

(54) MULTI-PURPOSE INTERACTIVE COGNITIVE PLATFORM

(71) Applicant: CONFLU3NCE LTD, Jerusalem (IL)

(72) Inventor: Tami Robyn Ellison, Jerusalem (IL)

(73) Assignee: Conflu3nce LTD, Jerusalem (IL)

( * ) Notice: Subject to any disclaimer, the term of this patent is extended or adjusted under 35 U.S.C. 154(b) by 203 days.

(21) Appl. No.: 16/550,022

(22) Filed: Aug. 23, 2019

(65) Prior Publication Data

US 2019/0378621 A1  Dec. 12, 2019

Related U.S. Application Data

(63) Continuation-in-part of application No. 16/427,305, filed on May 13, 2019, now Pat. No. 11,158,060, which is a continuation-in-part of application No. 16/262,884, filed on Jan. 30, 2019, now Pat. No. 11,176,675, and a continuation-in-part of application No. 15/884,565, filed on Jan. 31, 2018, now Pat. No. 10,582,189, said application No. 16/262,884 is a continuation-in-part of application No. 15/884,565, filed on Jan. 31, 2018, now Pat. No. 10,582,189, application No. 16/550,022, which is a continuation-in-part of application No. 15/884,565, filed on Jan. 31, 2018, now Pat. No. 10,582,189.

(60) Provisional application No. 62/721,665, filed on Aug. 23, 2018, provisional application No. 62/626,208, filed on Feb. 5, 2018, provisional application No. 62/499,655, filed on Feb. 1, 2017.

(51) Int. Cl.
*G16H 50/30* (2018.01)
*G06F 3/0482* (2013.01)
*G06F 3/01* (2006.01)

(52) U.S. Cl.
CPC ............ *G16H 50/30* (2018.01); *G06F 3/011* (2013.01); *G06F 3/0482* (2013.01)

(58) Field of Classification Search
CPC ....... G06F 3/011; G06F 3/0482; G16H 10/20; G16H 50/20; G16H 50/30
See application file for complete search history.

(56) References Cited

U.S. PATENT DOCUMENTS

| | | | | |
|---|---|---|---|---|
| 8,379,972 B1* | 2/2013 | Wang | ...................... | H04N 5/272 382/162 |
| 8,380,005 B1* | 2/2013 | Jonsson | ................... | G06T 11/60 382/282 |
| 8,699,754 B2* | 4/2014 | Zhang | ................ | G06K 9/00798 382/104 |
| 8,913,128 B2* | 12/2014 | Wu | ........................... | H04N 7/18 348/142 |

(Continued)

*Primary Examiner* — Ian L Lemieux
(74) *Attorney, Agent, or Firm* — David Lewis

(57) ABSTRACT

An interactive cognitive platform is provided that uses image-based interactivities for diagnosis, treatment, and to analyze the progress (for disease and/or treatment) of cognitive diseases via a graphical user interface. The interactivities engage multiple cognitive domains and involve Gestalt principles—aspects which can be personalized to be more effective for each user. The cognitive platform can be used by healthcare workers to produce diagnostics or treatment plans for specific cognitive conditions and diseases with a cognitive component. The cognitive platform can be used for gaming, stress reduction and skills development and performance enhancement for those without cognitive problems.

33 Claims, 25 Drawing Sheets

(56) References Cited

U.S. PATENT DOCUMENTS

| | | | | |
|---|---|---|---|---|
| 10,169,680 | B1* | 1/2019 | Sachdeva | G06F 3/04845 |
| 2008/0304705 | A1* | 12/2008 | Pomerleau | B60R 1/12 |
| | | | | 382/103 |
| 2009/0257650 | A1* | 10/2009 | Lim | G06K 9/00704 |
| | | | | 382/165 |
| 2010/0014781 | A1* | 1/2010 | Liu | H04N 13/261 |
| | | | | 382/285 |
| 2012/0033073 | A1* | 2/2012 | Jo | G06T 7/12 |
| | | | | 348/143 |
| 2012/0189190 | A1* | 7/2012 | Bala | G06T 7/187 |
| | | | | 382/154 |
| 2013/0051671 | A1* | 2/2013 | Barton | G06T 7/12 |
| | | | | 382/173 |
| 2013/0230237 | A1* | 9/2013 | Schlosser | G06T 7/10 |
| | | | | 382/164 |
| 2013/0230254 | A1* | 9/2013 | Wu | G06T 5/006 |
| | | | | 382/199 |
| 2014/0119643 | A1* | 5/2014 | Price | G06T 7/11 |
| | | | | 382/164 |
| 2014/0161359 | A1* | 6/2014 | Magri | G06T 7/13 |
| | | | | 382/199 |
| 2014/0205184 | A1* | 7/2014 | Franke | G06K 9/00805 |
| | | | | 382/154 |
| 2015/0195496 | A1* | 7/2015 | Hayakawa | B60R 1/00 |
| | | | | 348/118 |
| 2015/0221079 | A1* | 8/2015 | Schultz | G01S 17/89 |
| | | | | 382/190 |
| 2021/0342606 | A1* | 11/2021 | Liu | G08G 1/148 |

* cited by examiner

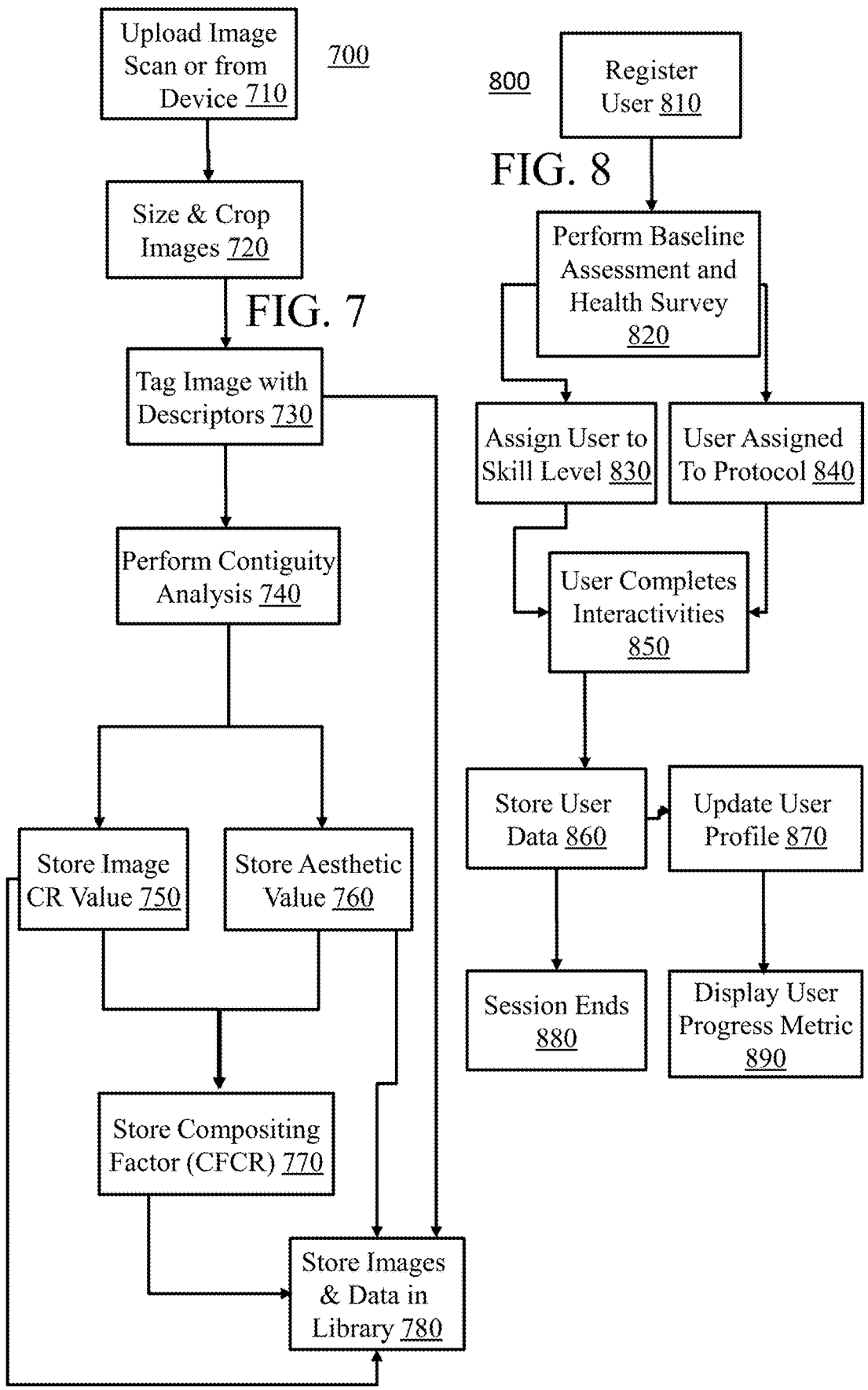

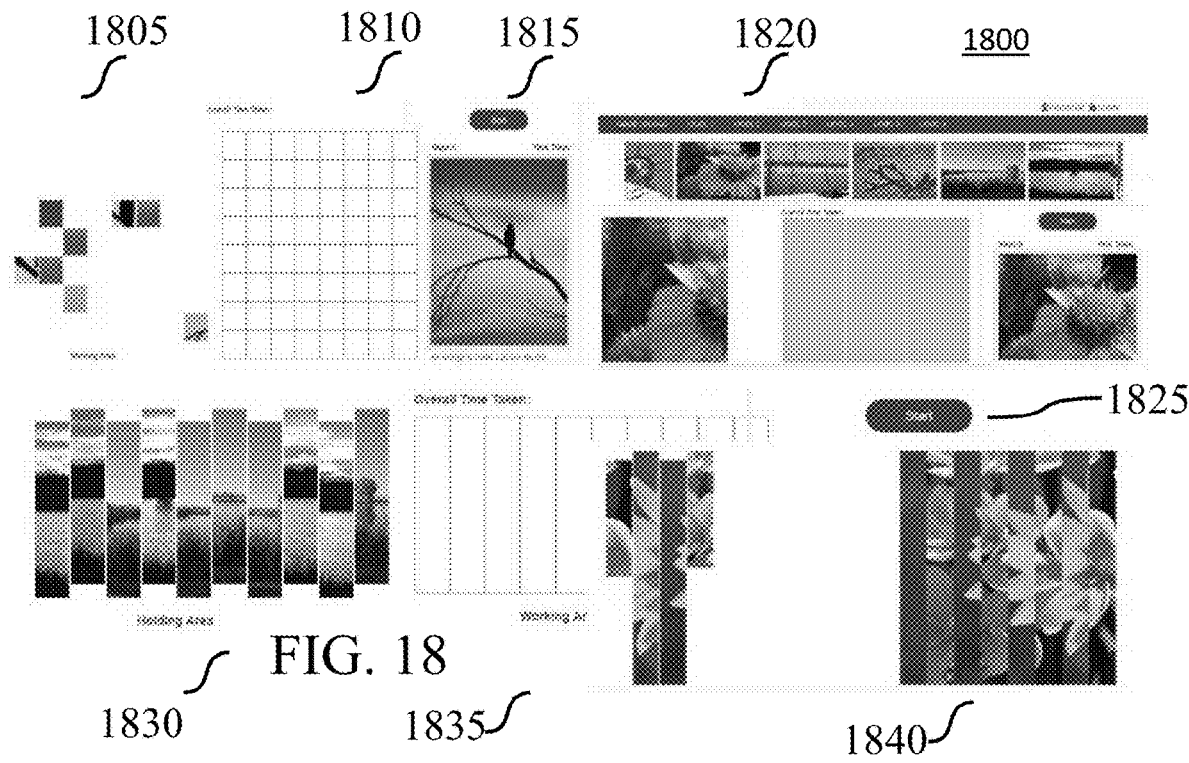

| AE, Rules Table: Contiguity Continuity Range (-1.0 to +1.0) Vertical Disruptor and Irregular Edge | |
|---|---|
| If | Then |
| an image has at least one contiguity which is continuous across the entire width of the image (75-100% +/-3%) | Assign a value of 1.0 |
| the contiguity is continuous across 50-75% +/-3% of the image | Assign a value of 0 |
| the contiguity is <50% or if contiguity # is 0 | Assign a value of -1.0 |
| there is/are Vertical Distractors extending >5% but less than 30% up from any otherwise linear and continuous contiguity, but which has additional complex contiguities | Assign a value of 0.5 |
| VD extends greater than 30% but less than 50%; | Assign a value of -0.5 |
| VD extends greater than 50% but less than 100% | Assign a value of -0.75 |
| VD is equal to or greater than 100% | Assign a value of -1.0 |
| there are 2-3 Vertical Distractor but which are spatially separated, or which individually extend less than 20% from an otherwise linear contiguities | Assign a value of 0.5 |
| there are multiple Vertical Distractors present in the image (e.g trees) | Assign a value of -1.0 |
| there are multiple irregular edges on one or more contigs or if a single contiguity without an adjacent color block >30% of the image | Assign a value of -0.25 |
| there is a single contiguity with a poorly defined edge but which is adjacent to at least one continuous color block or a color block >30% | Assign a value of -0.15 |

FIG. 19B

| AF$_5$ Rules Table. Color Block Depth$_{100}$ and CBD$_{ST}$ | | | | |
|---|---|---|---|---|
| Value | Quadrant 1 | Quadrant 2 | Quadrant 3 | Quadrant 4 |
| 1.00 | A | A | A | A(B) |
| 0.75 | A | A | B | B |
| 0.625 | A | A/B | C | C |
| 0.5 | A | A | B | C |
| 0.5 | A | B | A | B |
| 0.25 | A | B | C | A |
| 0.1 | A | B | C | D |

| AF$_6$ Spatial Color-Contiguity Table (compares AF$_1$ to AF$_2$) | |
|---|---|
| Value | Condition Rules |
| 0 | If AF$_1$ = AF$_2$ |
| 1 | If AF$_1$ is greater than AF$_2$ |
| 2 | If AF$_1$ is less than AF$_2$, unless the contiguity number is equal to 0 |
| -1 | If AF$_1$ = 0 |

FIG. 19C

| Ambiguity Factor | Range | Description/Formula |
|---|---|---|
| Contig Number (AF$_1$) | 0-6 | Sobel or Differential Edge counts using color and thresholded images. Compare b/w area counts |
| Color Block (AF$_2$) | 1.0-6.0 | Sequential color extraction using reduced 2-6 color images, quadrant-based identification of dominant colors (total, Q1-A4, top, bottom, right, left) |
| Linearity (AF$_3$) | -1.0 to +1.0 | $C_{linearity} = C_A + C_D$ where $C_A$ is the angularity across the contiguity and $C_D$ is a break in the contiguity |
| Continuity (AF$_4$) | -1.0 to +1.0 | $C_{cont} = C_{VD} + C_{IE}$ (rules table FIG. 11A) |
| Color Block Depth (100) (AF$_5$) | 0.25 to 1.0 | define color block distribution (rules table FIG. 11B) |
| Spatial Color-Contig (AF$_6$) | -2.0 to +2.0 | compare contiguity number to color block number (rules table FIG. 11C) |
| Ambi Value (Ambiguity Value) | | 0.75 to 2.25 |

MULTI-PURPOSE INTERACTIVE COGNITIVE PLATFORM

PRIORITY CLAIM AND CROSS-REFERENCE TO RELATED APPLICATIONS

This application claims priority benefit of U.S. Provisional Patent Application No. 62/721,665, entitled "MULTI-PURPOSE INTERACTIVE COGNITIVE PLATFORM," filed on Aug. 23, 2018, by Tami Ellison;

this application is a continuation-in-part of U.S. patent application Ser. No. 16/427,305, entitled "SYSTEM AND METHOD FOR CREATING AN IMAGE AND/OR AUTOMATICALLY INTERPRETING IMAGES," filed on May 30, 2019, which in turn is a continuation-in-part of U.S. patent application Ser. No. 16/262,884, "SYSTEM AND METHOD FOR CREATING AN IMAGE AND/OR AUTOMATICALLY INTERPRETING IMAGES" by TAMI ROBYN ELLISON, filed on Jan. 30, 2019; which claims priority benefit of U.S. Provisional Patent Application No. 62/626,208, entitled "SYSTEM AND METHOD FOR IDENTIFYING CONTIGUITY CHARACTERISTICS IN AN IMAGE," filed on Feb. 5, 2018, by Tami Ellison, which is incorporated herein by reference; and also claims priority benefit of U.S. Provisional Patent Application No. 62/721,665, entitled "MULTI-PURPOSE INTERACTIVE COGNITIVE PLATFORM," filed on Aug. 23, 2018, by Tami Ellison, which is incorporated herein by reference; U.S. patent application Ser. No. 16/262,884, "SYSTEM AND METHOD FOR CREATING AN IMAGE AND/OR AUTOMATICALLY INTERPRETING IMAGES" by TAMI ROBYN ELLISON, filed on Jan. 30, 2019 is also a continuation-in-part of U.S. patent application Ser. No. 15/884,565 entitled "SYSTEM AND METHOD FOR GENERATING COMPOSITE IMAGES," filed on Jan. 31, 2018, by Tami Ellison, which claims priority benefit of U.S. Provisional Patent Application No. 62/499,655, entitled "PHOTAGE 2.5D-METHOD AND SYSTEM FOR CREATING DYNAMIC VISUAL ILLUSIONS USING COMPLEX, JUXTAPOSED AMBIGUOUS IMAGES," filed on Feb. 1, 2017, by Tami Robyn Ellison; U.S. patent application Ser. No. 16/427,305, entitled "SYSTEM AND METHOD FOR CREATING AN IMAGE AND/OR AUTOMATICALLY INTERPRETING IMAGES," filed on May 30, 2019, is a continuation-in-part of U.S. patent application Ser. No. 15/884,565 entitled "SYSTEM AND METHOD FOR GENERATING COMPOSITE IMAGES," filed on Jan. 31, 2018, by Tami Ellison, which claims priority benefit of U.S. Provisional Patent Application No. 62/499,655, entitled "PHOTAGE 2.5D—METHOD AND SYSTEM FOR CREATING DYNAMIC VISUAL ILLUSIONS USING COMPLEX, JUXTAPOSED AMBIGUOUS IMAGES," filed on Feb. 1, 2017, by Tami Robyn Ellison; U.S. patent application Ser. No. 16/427,305, entitled "SYSTEM AND METHOD FOR CREATING AN IMAGE AND/OR AUTOMATICALLY INTERPRETING IMAGES," filed on May 30, 2019, claims priority benefit of U.S. Provisional Patent Application No. 62/721,665, entitled "MULTI-PURPOSE INTERACTIVE COGNITIVE PLATFORM," filed on Aug. 23, 2018, by Tami Ellison;

this application is also a continuation-in-part of U.S. patent application Ser. No. 15/884,565, entitled "SYSTEM AND METHOD FOR GENERATING COMPOSITE IMAGES," filed on Jan. 31, 2018, by Tami Ellison, which is incorporated herein by reference; U.S. patent application Ser. No. 15/884,565 claims priority benefit of U.S. Provisional Patent Application No. 62/499,655, entitled "PHOTAGE 2.5D-METHOD AND SYSTEM FOR CREATING DYNAMIC VISUAL ILLUSIONS USING COMPLEX, JUXTAPOSED AMBIGUOUS IMAGES," filed on Feb. 1, 2017, by Tami Robyn Ellison. The contents of all of the above listed applications are incorporated herein by reference, in their entirety

FIELD

This specification generally relates to a multi-purpose interactive cognitive platform.

BACKGROUND

The subject matter discussed in the background section should not be assumed to be prior art merely as a result of its mention in the background section. Similarly, a problem and the understanding of the causes of a problem mentioned in the background section or associated with the subject matter of the background section should not be assumed to have been previously recognized in the prior art. The subject matter in the background section may merely represent different approaches, which in and of themselves may also be inventions.

Cognitive issues affect hundreds of millions of people around the world. Current neurocognitive evaluations are based on decades/century-old siloed skills' tests using simple stimuli Today's "multi-domain" assessments are individual skills assessments compiled into batteries. Not surprisingly, these evaluations are limited by ceiling and floor effects, and lack the sensitivity to detect subtle changes over time, delaying early detection, diagnosis and interventions. Despite tremendous gains in knowledge/technology, there is a lack of non-invasive, objective, quantifiable, authentic multi-domain assessment tools and training products to support brain health and fitness.

Cognitive platforms can be used for a variety of reasons including therapy diagnosis and treatment of cognitive disorders, gaming, and even in the field of artificial intelligence. However, new and improved cognitive platforms able to address deficiencies and limitations of prevailing platforms are needed.

BRIEF DESCRIPTION OF THE FIGURES

In the following drawings like reference numbers are used to refer to like elements. Although the following figures depict various examples of the invention, the invention is not limited to the examples depicted in the figures.

FIG. 7 shows an example of a flowchart of a method of storing images and date to a library for use with an interactive cognitive platform.

FIG. 8 shows an example of a flowchart of a method to build a user profile for a multi-purpose interactive cognitive platform (a method of On-boarding).

FIG. 18 shows an example of a Graphical User Interface (GUI) PICSSi prototype for a multi-purpose interactive cognitive platform.

FIGS. 19A-19D show an example of Rules that can be used for measuring contiguity ranges (19A), color block depth (19B), spatial color contiguity (19C), and ambiguity factor (19D) for a multi-purpose interactive cognitive platform.

DETAILED DESCRIPTION

Although various embodiments are described in this specification may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

The flowchart and block diagrams in the FIGS. illustrate the architecture, functionality, and operations of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In this specification, the term "logic" refers to a specialized circuit, embedded software, middleware, (note embedded software is hardware and middleware includes hardware), software, a specialized processor, a Very Large Scale Integration (VLSI) chip, a configured Application Specific Integrated Circuit (ASIC), a configured Field Programmable Gate Array (FPGA), or other logic circuit optimized and/or configured for the task in question (see U.S. Pat. No. 6,785,872 for methods for converting algorithms into circuits, which is incorporated herein by reference).

The present invention may be a system, a method, and/or a computer program product. The computer program product may include a computer readable storage medium (or media) having computer readable program instructions thereon for causing a processor to carry out aspects of the present invention.

Figure 1:
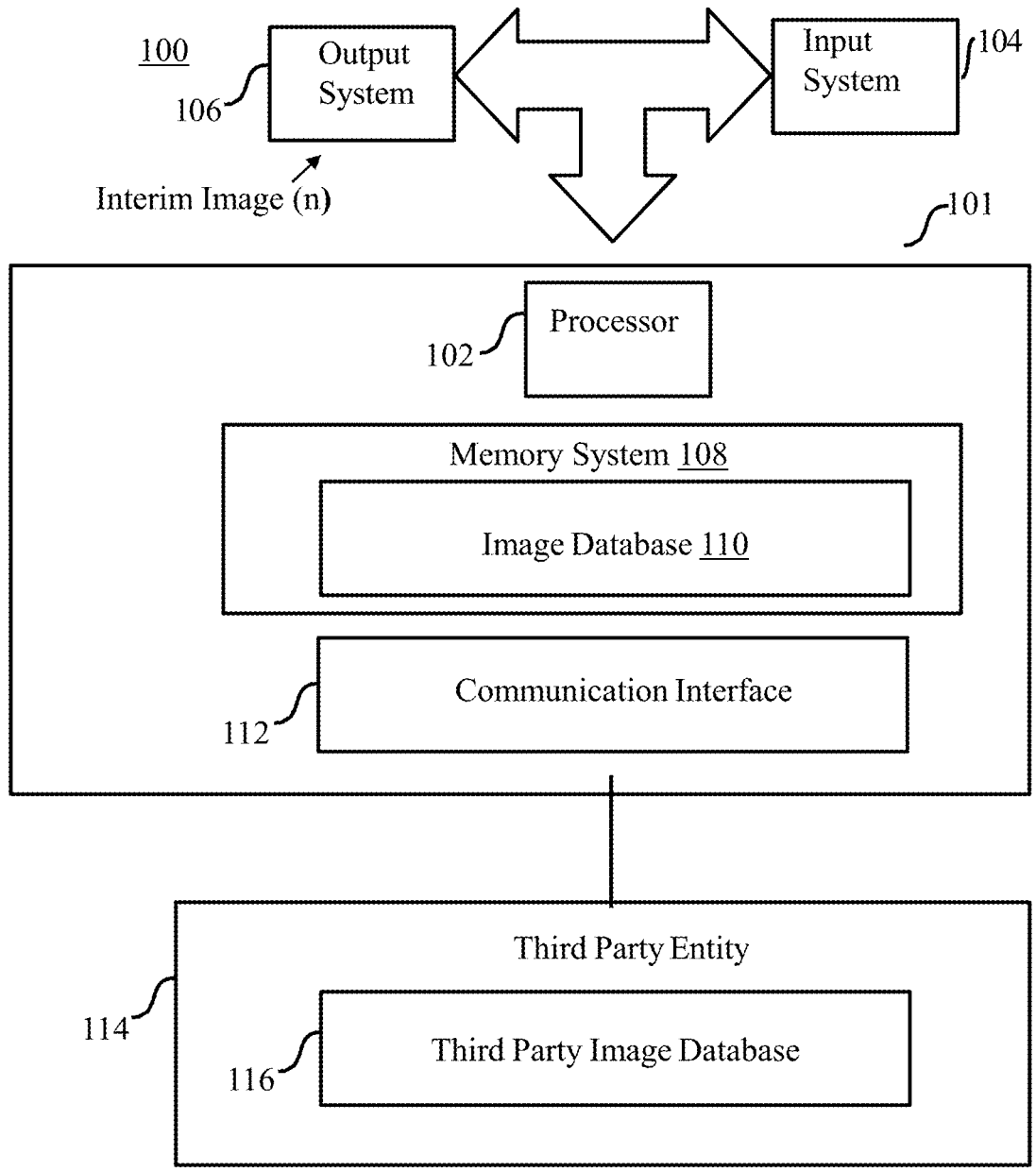
FIG. 1 is a block diagram of an example of a system that analyzes an image for a multi-purpose interactive cognitive platform.

FIG. 1 is a block diagram of an example of system 100 that analyzes an image for an interactive cognitive platform. System 100 may include machine system 101, which has processor system 102, input system 104, output system 106, memory system 108, image database 110, communication interface 112, and third party system 114 and third party database 116. In other embodiments, System 100 may include additional components and/or may not include all of the components listed above.

System 100 relates to a platform in which cognition and cognitive processes can be applied to people and/or machine processes, which utilize, and/or which are modeled on, human cognitive and vision processes. In support of brain health, the platform can be applied to people across the cognitive spectrum towards supporting cognitive function, information and language processing, learning, training, screening, stimulation, skills development, stress reduction, therapy, and remediation purposes. Cognition can be viewed in terms of individual brain and neurological processes as well as holistically considering the totality of conscious and subconscious input and/or stimuli and the interpretation, analysis, storage and translation of such inputs into a wide range of output forms. The platform's image-based interactivities may be used to support human perception, cognition, behavior and interactions with the environment and the world, directly and/or indirectly, such as through a secondary device or other type of interface. The secondary device may be worn, implanted or transmitted signal, in the immediate, short-term and/or for later retrieval.

Cognition can be viewed in terms of allocated cognitive domains responsible for critical functions and processes, including: memory, attention, executive functions, language and communication, sensorimotor, and visual-spatial operations. Each of these domains may include a multiplicity of processes and skills. Each of the processes within a domain and/or multiple domains may be integrated with one or more other processes and/or domains with crossover relationships. Neurocognitive functions provide a framework for how the brain functions and/or a gateway to understanding brain dysfunctions.

Brain processes associated with learning and by default memory and attention operations, among other cognitive domains, can also be described in terms of thinking skills. Thinking skills are traditionally hyphenated into "higher" order thinking skills (HOT) and "lower" order thinking (LOT) skills; a taxonomy first developed by B. S. Bloom in the 1950's and generally applied to educational targets. The principles related to thinking can be generalized to learning where processes require the mustering of both higher order thinking skills including critical, logical, reflective, meta-cognitive, and creative thinking for analyzing, evaluating, synthesizing and creating, together with lower order thinking (LOT) skills which include: applying, understanding and remembering. The totality of higher and lower order thinking skills become integrated when considering cognition and cognitive processes and their participation in perception. HOT and LOT skills can be framed by the domains described previously with the application of the processes within the cognitive framework to help people interact with their environment and the world around them. More recently, the fields of neuroscience and educational practices has gained an appreciation for learning styles—a differentiation which not only applies to learning and training, but also to assessments and how these are conducted to integrate individual learning styles, including: auditory, verbal (linguistic) visual-spatial, kinesthetic (movement), among others. Individuals can have a bias toward a particular learning style, but generally display a mix of learning styles which can be differentially manifested depending on task requirements.

Different learning styles may be accommodated in a variety of ways. In embodiments of the platform, a visually driven system (e.g., with visual sensory input), provide triggers for visual memory—an important driver and/or indicator of cognition. Further, the associative connections to visual memories and pattern recognition can be used to integrate different learning styles. Learning in this case not defined by books but rather by inputs and associating neural connections. From a pure learning standpoint, instructions are provided in text, images, and/or audio format. The assessments integrate verbal descriptive responses; kinesthetics (moving puzzle piece parts). Rewards for task completion may be in the form of audio output, and may include background music to provide audio lifts (e.g., music commonly associated with a positive outcome and/or a victory). The platform may allow users to express responses and/or demonstrate capabilities, incorporate non-visual content, and expression, which may support a mix of learning styles. When designing interactivities and companion tests/assessments both processes are relevant—the activity and assessments (or described as tests in academic settings).

Brain processes, whether in healthy and/or impaired individuals, can be further framed within the context of top-down processes and bottom-up processes. In bottom-up processing sensory input can be received, assembled and integrated through multiple steps; whereas, in top-down processing cognition draws on, uses and applies models, ideas, and expectations (inferences) to interpret sensory data and generally leads to some kind of output and/or response. Sensory input and the upstream and/or downstream processes, including analysis can be complex. For example, recognizing the nuances of fire can mean discriminating between a building which is on fire, an out-of-control conflagration versus a single candle burning on dining room table or knowing that a pot on a stove is potentially hot (an associated connection to fire). Associative neuronal connections to concepts and practices all require some kind of sensory input and the integration of multiple sensory inputs, (seeing the fire, feeling the heat, smelling smoke), prior knowledge and memory inputs (top-down inputs) and woven together in a rich web of connections.

Sensory input can include: visual, auditory, tactile, motor/kinesthetic movement, gustatory among other types of inputs which can be sensed directly and/or indirectly or transduced through a secondary medium and/or device, including an implantable or wearable, as well as through computer-brain/neural interfaces and other human-machine interfaces, whether through permanent or temporary interactions.

A significant body of research has been dedicated to understanding cognitive function as it relates to brain health, well-being, reasoning, decision-making, learning styles, skills development in healthy individuals and in those with changes in brain health associated with disease conditions. A diversity of processes, changes, differences and impacts, and/or altered states which are reflected in the range of diseases and conditions with overlapping symptoms and impacts on one or more cognitive processes. Conditions with a cognitive component, include: ADHD, ADD, Autism, Multiple Sclerosis, Parkinson's Disease, Type II Diabetes, Atrial Fibrillation, aging/mild cognitive impairment, Alzheimer's disease, and Dementias, stress, Chemotherapy, post-anesthesia cognitive dysfunction, schizophrenia, among other transient, progressive, acute and/or chronic physiological, psychological neuromuscular and other conditions.

The platform described here is designed to support brain health through diagnostic assessment, intervention, and treatment modalities; and, to engage cognition in support of learning and skills development and training enhancements as a standalone methodology delivered through the platform, and/or in conjunction with other assessment tools, devices and/or therapies, such as exercise equipment and/or with a passive and/or active exercise protocols including whole body vibration, transcranial magnetic processes, and/or as an adjunct modality, and/or assessments to support cognitive well-being and cognitive processes.

The platform can be used as part of a system to help support brain health as a potential treatment modality, an intervention that can be delivered as a device-based intervention using smart devices, such as a computer, tablet, phone or other type of interfacing device. For example the interfacing device may be a hands-on interactive or in view-only mode; and/or delivered offline as either a hands-on manipulative and/or in view-only mode. Offline, the platform materials and interactive tools can be projected and/or printed on a pre-sectioned substrate or a substrate, which can be sectioned, allowing the parts to be manipulated (e.g., as a picture puzzle that needs to be assembled); or, which have been printed or transferred onto a different medium, and/or are presented in view-only mode printed and/or projected on a substrate; and/or a hybrid of online and offline components. The platform may be include a subset of overlapping assessments which can be conducted with both the device-based and offline tools for crossover multi-modal analysis and tracking. The platform can provide a distinction between verbal and non-verbal users; and with use cases including minimally conscious individuals who can access the view-only options. In these embodiments, assessments of interactions requires the use of biometrics such as eye-tracking and EEG as an index of engagement.

The platform provides a method for developing a treatment plan for a patient, or for delivering a multiplicity of interactivities, interventions and/or user engagements according to healthcare workers (e.g., clinicians, researchers) or other user and/or system protocols to meet and/or address individual and/or group cognitive and/or training requirements for healthy individuals as well as for those who are experiencing cognitive challenges in order to address individual cognitive domains a part of holistically engaging multiple cognitive domain processes and skills as an integrated system. An interactivity is an activity that the user (e.g., a patient) participates in, as part of interacting with the platform. Interactivities include games, puzzles, therapeutic exercises, diagnostic tests, for example. A user can be any one of the following: a patient, an individual, a healthcare worker, a researcher, a professional gamer, game maker, and/or a clinician, for example. In some embodiments, the term "user" can refer to any one or all of the above. In any of the embodiments, each of the terms a patient, an individual, a healthcare worker, a researcher, a professional gamer, game maker, and/or a clinician may be substituted one for another to obtain a different embodiment. In some embodiments, the term healthcare worker can refer to any worker in the healthcare industry including, but not limited to, a researcher, a doctor, a clinician, therapist, a nurse, and a laboratory technician.

System 100 provides a multi-purpose interactive cognitive platform for cognitive well-being and skills training, and assessment/diagnosis of cognitive dysfunction. System 100 provides a platform for healthcare workers to implement assessments for a variety of cognitive functions and dysfunctions.

System 100 is a network of systems including multiple machines communicating via a network, which may be used for treatment and diagnosis, for example, by analyzing images and/or creating artistic images by combining multiple images into one image, such as by interweaving multiple images with one another. The image sets may embed multiple Gestalt principles (figure-ground, closure, continuation), engaging top-down cognition and bottom-up sensory processing, as users virtually reassemble the spatially separated image parts in virtually reconstructing the intact image.

In one embodiment, the cognitive platform is a PICSSi/Mem+ prototype which is designed to engage cognition with a simple question, such as "what do you see?" The term "Mem+" refers to testing for memory plus other aspects of cognition related to memory. The PICSSi/Mem+ system uses real-world images—enriched visual stimuli—to cooperatively engage global cognition (skills and processes across multiple cognitive domains). Using real-world images combined with the simple question, improves the quantity and quality of captured data (as compared to if other images and/or questions were used), allowing for direct measurements of overall cognitive status as well as domain-specific task/skill metrics, towards developing sensitive, reliable cognitive tools. In an embodiment, the question is open ended. In an embodiment, the question is one that only requires a one word or one phrase response. In an embodiment, the question is 7 or less words. In an embodiment, the question is 10 or less words. In an embodiment, the question is 15 or less words. In an embodiment, the question is 20 or less words. In an embodiment, the question requires that the user analyze interweaved image sets, focusing a range of cognitive in the process, including language and memory domains, but also attention, visual spatial and executive functions processes and skills. In situations where some users may not have firsthand experience with the content of an image, for example, a field of sunflowers, but the user has experienced flowers, the image set can still be of value in training, treatment and assessment. Similarly, while lakes are familiar to a significant number of people, even those who have never experienced a lake can recognize a lake in its relationship to water and/or a body of water.

In one embodiment, the platform can be deployed in and through a device with components on a tablet, computer, phone, television, smart device and/or other virtual, augmented and/or mixed reality device and/or medium as part of the Internet of Things (IoT) ecosystem of interconnected devices. The interactive components can be used in hands-on and/or hands-free and/or view-only mode. The hands-on mode may include manipulatives with multiple types of input devices including touch-screens, mouse, stylus, pads, and/or Tangible User Interface props, virtual projections, voice commands, and/or other types of input devices. The hands-free modality may include multiple types of interfaces, including neural feedback, eye-tracking, biofeedback, sensors implanted into the human body, sensors attached to the human body wearable, and/or other types of add-on system and/or device, or other biometrics tools. The input may include wifi (e.g., via a radio frequency local area network), infrared, ultraviolet, low frequency sound, ultrasound, and/or Bluetooth, for example.

In an embodiment, a tangible user interface (TUI) is a user interface in which the user interacts with digital information through the physical environment. The TUI gives physical form to digital information, and may include sensor to sense the manipulation of physical objects and materials other than a keyboard. In an embodiment, a TUI of this specification does not include a mouse (although, in this embodiment, mouse input may be used, without a TUI, instead a TUI and/or in addition to a TUI, a mouse is not included in the scope of the term TUI of this specification). The TUI prop provides a tactile interface, giving digital information, such as digital puzzle pieces, a physical form. The TUI prop transforms digital information in manipulatable and perceptible parts of the platform. TUI props, within the Internet of Things space, can be embedded with additional sensors to capture otherwise inaccessible user data through traditional active surface devices or other types of inputs. In an embodiment, a TUI may include a physical representation that is computationally coupled to underlying digital information, such as images and text. In an embodiment, a TUI includes space-multiplex both input and output, concurrent access and/or manipulation of interface components, specific devices (via which input is sensed); spatially aware computational devices; and/or spatially reconfigurable of device.

In one embodiment, the platform includes offline interactive components which can be delivered visually through printed matter, including, but not limited to: paper, plastic, glass and/or wood substrates. The offline components can include manipulatives where images are printed in sections on wood substrates. In one embodiment, each component image is printed on four (4) 14 cm×3 cm substrates, for a total single composed picture of 14 cm×12 cm in size. Different sized manipulatives can be printed based on the substrate used, including varying the width of the sections, and number of sections, including half and quarter-sized sections and smaller. In one embodiment, individual image manipulatives can be printed on a chip-board substrate and cut accordingly, or a printed image can be section and mounted onto a substrate rather than being printed, transferred and/or sublimated onto a substrate, or use snap-together sections which can be split and/or combined together. In one embodiment, the hybrid system would include the use of a TUI prop. In an embodiment, the prop's digital display surface would show an image section or image part which would be "released" to an active surface when the user correctly places the image part, displayed on the prop surface, proximal to the mapped game board surface.

In one embodiment, the platform can include all of its integrated components, including: image library, image sets, image database which includes: integrated software, delivery and server-side storage, interactivities, skill levels, interactivity progressions algorithms, complexity values, composite values, user interfaces, user data tracking, real-time feedback, data logging, assessments, reporting and alert tools to provide users and/or professionals with one or more metrics of cognitive status. In one embodiment, the platform can also be represented as multiple modules which can be interchanged and/or configured to meet individual and group requirements according to clinical health specifications.

Machine system 101 includes one or more machines that run an image analysis system. Each machine of machine system 101 may run the cognitive platform/image analysis system independently and/or as a distributed system. Machine system 101 may include one or more Internet servers, network servers, a system for analyzing images, may include one or more mobile machines and/or may include other machines that include machine vision, for example.

In at least one embodiment, in machine system 101, each image and/or each image of a plurality of images may be analyzed to identify contiguity characteristics in the image that facilitate identification of visual qualities and characteristics indicative of how the viewer observes the image for use in treatment and/or diagnosis of cognitive issues. In an embodiment, a contiguity is a continuous region having relatively uniform and identifiable color and content characteristics, and which may span the entire width of an image or a portion of it. In an embodiment, a contiguity is a region that is recognized by the system as one region.

As an aside, the value of a color may be represented as Hue-Saturation-Value instead of by wavelength of light. The pixel values may be used to represent the Hue-Saturation-Value or the color. Alternatively, each color may be represented by a separate pixel value. Returning to the discussion of uniformity, in another embodiment, a color is considered uniform if the variation of the pixel value representing the color varies by less than 10%, less than 5%, or less than 1% (depending on the embodiment). In another embodiment, a color is considered uniform if the variation of the pixel value representing the color varies by 10% or less, 5% or less, or 1% or less (depending on the embodiment). In another embodiment, a color is considered uniform if the variation of the pixel value representing the color varies by no more than 25 bits, no more than 15 bits, no more than 5 bits, no more than 3 bits, or no more than 2 bits (depending on the embodiment).

In an embodiment, contiguities (which may be referred to as "contigs") may be compared to, horizon-like edges according to certain characteristics and may include horizontal edges that are associated with a horizon. However contiguities may also contain significantly more information beyond just information about edges. A contiguity may be any generally horizontal feature, such as a line or a block of pixels that are within a predetermined threshold of uniformity of color between pixels that are within a predetermined number of pixels or distance form one another (thereby having a "local uniformity"). Local uniformity refers to the uniformity in color between nearby and/or neighboring pixels. In an embodiment, contiguities extend for at least half the width of the image. Contiguities may be associated with a multiplicity of characteristics within a given image and any given contiguity may be associated relationships between that contiguity and other contiguities that are in the same components of the image and as conveyed in a composite image. Contiguity characteristics include: contiguity number, contiguity stacking, linearity, continuity, angularity, depth/saliency, regularity, and color composition. Contiguities may be framed by their content, color and context information.

In an embodiment, the contiguities that are of interest are those that extend horizontally across the image, which for example extend at least 75% of the width of the image (in other embodiments smaller or larger percentages of the width may be used). In an embodiment, the contiguities of interest can make an angle of 45 degrees or less with a horizontal line (in other embodiments the angle may be 75 degrees or less, 60 degrees or less, 30 degrees or less, or 15 degrees or less, for example). A contiguity can separate regions of the image and/or may define a region of the image. In at least one embodiment, the contiguity characteristics may include contiguity lines that separate different color segments in the image, e.g. the contiguities may form edges between the color segments. A contiguity line may separate a contiguity from other regions. In at least one embodiment, the images display landscape scenes in which the contiguity lines are naturally occurring horizon edges, horizon type edges, and/or border lines (e.g., edges that extend more than 50% of the width of the image and that are at an angle of less than 45 degrees). In an embodiment a contiguity line may also be horizontal. For example, in urban settings contiguity lines can be horizontal, but which depends on the subject matter. The edges of the contiguity may separate color sections of the image, for example the edges of a contiguity may separate between the background and the foreground, between objects, between different parts of a background, between different parts of a foreground, different parts of an object, and/or the like.

The contiguity characteristics may enable a person viewing the image to mentally organize parts of the scene displayed in the image into different areas that allow the viewer to understand what is shown, and can be used to train a computer vision system to recognize continuities even between disrupted contiguities, which may be absent or obstructed. The terms disrupt and disruptor are used interchangeably with the terms distract and distractor. Either may be substituted one for the other to obtain different embodiments. The contiguity lines can provide a contrast, enabling the person's brain or the computer vision system to organize and evaluate the image and to resolve ambiguities in the image, image set, and/or image scene. In at least one embodiment, contiguities may be used to inform image classification (that is may be at least one factor used in determining the classification of an image) and can be used to identify content and aid in finding objects and/or regions in the image. The classification of an image is at least a part of identifying the content of the image. A classification system may have categories and subcategories and the smallest subcategories may be objects or parts of objects that are identified.

In at least one embodiment, contiguity may be defined and used to train systems to recognize parts of a whole. For example, a contiguity may correspond to (and thereby identifying the contiguity identifies) a single object or a contiguity may correspond to (and thereby identifying the contiguity identifies) a distinctive part of an object. When training a machine, contiguities may need to be identified in both single images as well as composites, and in composite images the contiguities may be split (or divided) by the other images of the composite image. A composite image is an image formed by combining at least two images together. For example, the at least two images may be interweaved with one another. The figure and ground relationships in a composite image is another value vis-a-vis training sets that may be used to further define relationships of objects in an image. An element, object, or region of an image is in the figure position when the element object or region is located where a main character of photograph would be located. An element, object, or region is in the ground position if the element, object, or region forms a contiguity that stretches across the image.

In at least one embodiment of the cognitive platform, the user's ability to recognize the parts of the whole, to apply a label, to virtually reconstruct the hyphenated mage segments, to differentially focus attention on the figure or ground positioned image in a composite musters coordinated multi-cognitive domain engagement in resolving the ambiguities inherent in the image sets based on the user's knowledge, experience and memories. In at least one embodiment, the user's interactions with the image sets, i.e. the composite of interweaved image sections, is through the gamified image parts and the interactivities mix defined by the user, a clinician, a therapist or researcher.

As another example, two contiguities may, or contiguity lines may section off, a region of an image that is one object or a group of related objects. Contiguities may be seen as familiar horizon lines, interfaces with a known and/or predictable color, color "context," and/or content characteristics, and may include information about the location of shapes and information about the density of a feature. The "context" of the color context refers to an assigned context, a context that is known for other reasons, a context that is predictable, and/or a context that is probabilistically inferred. The determination of the context may be based on the source of the data and/or user input specifying the context. For example, if the data has a known context, the accuracy of identifying objects may be improved and/or facilitated. The word "density" may refer to a concentration of colors or to the saliency of elements within a defined space which may have additional context, optionally, as a result of the co-localization of the elements within a given context to help in its identification and/or correct placement of the image part as the users works through the platform's interactivities. For example, the interface with a vertically positioned blue of relatively uniform density is likely to be a sky. A dark element on the surface or at the interface is likely to be a ship—all based on known contexts, associations and references that were previously learned over time.

As a further example, bodies of water often form contiguities and are regions of high density of water droplets. As another example, color blocks may aid in the identification of objects or regions contained in an image or a plurality of images or image scene. The context may aid in interpreting whether a contiguity is water. Water is transparent, but reflects the colors around it—a stormy sea with dark clouds will have very different characteristics than a calm sea or lake reflecting a blue sky with still water. Nonetheless, based on the context both can still be recognized and/or inferred as a body of water.

In at least one embodiment, the system 101 may be configured to identify the contiguity lines by applying various image processing filters to the image, e.g. Sobel, thresholding, and/or the like, to identify the contiguities in the image. In at least one embodiment, the system can be configured to perform a stitch analysis of the image to designate the contiguity characteristics that are preferred for use for analyzing components in the image and to facilitate identifying images with similar or overlapping characteristics.

Contiguities may be analyzed by juxtaposing non-adjacent image segments and masking a portion of the image in the process, which provides a rapid snapshot of the symmetrical and/or asymmetrical, color differences and contiguity regularity and continuity in deriving Aesthetic and Ambiguity Ratings towards developing a Compositing Factor for an image (such as by using a 1:3 stitch). Stitching may involve removing (or masking) portions of an image. For example, vertical sections of the image may be removed or masked. Throughout the specification the terms "remove" and "mask" and their conjugations, when used in reference to removing or masking part of an image are used interchangeably. Throughout the specification, the terms "remove" and "mask" and their conjugations may be substituted one for another to obtain different embodiments. The vertical sections removed may be of the same size as one another and equally spaced from one another. The juxtaposition and masking may be part of a stitching method where an image may be divided into 3 sections and section 1 is juxtaposed next to section 3. Section 2 may be masked in the process and gradually revealed as the stitched image is peeled. Measurements may be taken of the combination of one or more contiguities based on the complexity of the images comprising the image sets for image analysis purposes (FIG. 20A-E show an example of the a stitch and peel process). For example, the system can be configured to identify and designate contiguity lines that are horizontal, vertical, within a predetermined degree of angle deviation and/or the like, according to predetermined parameters provided to the system. Peeling or backstitching refers to putting back parts of the image that were masked or removed. In at least one embodiment, the stitch analysis may enable the system to identify contiguity characteristics that are obstructed by objects in the image that segment the contiguity line. In at least one embodiment, the stitch analysis may be implemented by dividing the image into a predetermined number of sections, e.g., three sections. At least one of the sections can be manipulated, e.g. shifted, to mask or overlap another section in the image. The overlapping section can then be peeled off the masked section to reveal portions of the masked section such that the contiguity line can be identified from the portions of the image being revealed via the peeling. An abrupt change in pixel value or Hue-Saturation-Value (HSV) in regions of the stitched image may indicate a potential disruption in the contiguity making the region a target region for further evaluation. A minimal change (within predetermined thresholds/limits) in pixel uniformity or a progression along a hue spectrum in other regions of the contiguity represents continuity of the contiguity across the width of the image.

In at least one embodiment, the system can be configured to identify the contiguity lines by applying various image processing filters to the image, e.g., via a Sobel filter, thresholding, and/or the like, to identify the contiguities in the image. In at least one embodiment, the system can be configured to perform a stitch analysis of the image to designate the contiguity characteristics that are preferred for use for analyzing components in the image and to facilitate identifying images with similar or overlapping characteristics. For example, the system can be configured to identify and designate contiguity lines that are horizontal, vertical, within a predetermined degree of angle deviation and/or the like, according to predetermined parameters provided to the system. In at least one embodiment, the stitch analysis can enable the system to identify contiguity characteristics that are obstructed by objects in the image that segment the contiguity line. In at least one embodiment, the stitch analysis can be implemented by dividing the image into a predetermined number of sections, e.g. three sections. At least one of the sections can be manipulated, e.g. shifted, to mask or overlap one other section in the image. The overlapping section can then be peeled off the masked section to reveal portions of the masked section such that the contiguity line can be identified from the portions of the image being revealed via the peeling.

The identification and analyses of contiguities in images is used to assign contiguity characteristics, complexity values and figure-ground specifications as these relate to the image itself and its relationship to other images when combined as a composite with one or more additional images.

Processor system 102 may include any one of, some of, any combination of, or all of multiple parallel processors, a single processor, a system of processors having one or more central processors and/or one or more specialized processors dedicated to specific tasks.

Input system 104 may include any one of, some of, any combination of, or all of a keyboard system, a mouse system, a trackball system, a track pad system, buttons on a handheld system, a scanner system, a microphone system, a connection to a sound system, and/or a connection and/or interface system to a computer system, intranet, and/or internet (e.g., IrDA, USB), for example Input system 104 may include a graphical user interface that third parties can interact with.

Output system 106 may include any one of, some of, any combination of, or all of a display, a monitor system, a handheld display system, a printer system, a speaker system, a connection or interface system to a sound system, an interface system to peripheral devices and/or a connection and/or interface system to a computer system, intranet, and/or internet, for example. Output system 106 may include a network interface via which third parties interact with machine system 101. Input system 104 and output system 106 may be the same system or different system.

Memory system 108 may include, for example, any one of, some of, any combination of, or all of a long-term storage system, such as a hard drive; a short-term storage system, such as random access memory; a removable storage system, such as a floppy drive or a removable drive; and/or flash memory. Memory system 108 may include one or more machine-readable mediums that may store a variety of different types of information. The term machine-readable medium is used to refer to any non-transient medium capable carrying information that is readable by a machine. One example of a machine-readable medium is a non-transient computer-readable medium. Another example of a machine-readable medium is paper having holes that are detected that trigger different mechanical, electrical, and/or logic responses. Memory system 108 may store one or more images for users to select from and/or that users may use.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server.

In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Image database 110 may be a database of images that may be analyzed, that were analyzed, and/or from which composite images may be formed. Optionally image 110 may include a relational database. Optionally, image database 110 may associate with images and/or portions of an image attributes, such as contiguity, ambiguity, juxtaposition (which is rating of a contiguity, which will be discussed further below), a color map and/or other color properties, saliency, complexity, aesthetic value, edge information, context information, content and/or category description, spatial information about contiguities, and/or threshold information. Optionally, image database 110 may be associated with a database server for retrieving information from image database 110. Optionally, the image server (if present) may be a relational database and the database server may be executed by processor system 102 or by its own processor system.

Communication interface 112 is an interface, via which communications are sent to and from machine system 101. Communications interface 112 may be part of input system 104 and/or output system 106.

Third party system 114 is a third party system and interacts with machine systems 101 to analyze images. Third party system 114 may include third party database 116, which stored images of the third party system 114. Third party system 114 is optional.

Processor system 102 may be communicatively linked input system 104, output system 106, memory system 108, and communication interface 112. Processor system 102 may be communicatively linked via any one of, some of, any combination of, or all of electrical cables, fiber optic cables, and/or means of sending signals through air or water (e.g. wireless communications), or the like. Some examples of means of sending signals through air and/or water include systems for transmitting electromagnetic waves such as infrared and/or radio waves and/or systems for sending sound waves.

In at least one embodiment, machine system 101 may be configured to implement the platform and/or receive an image from third party system 114, for example. The image may be stored in the image database 108, which may store other images. Processor system 102 may retrieve, and/or the image may be provided, image to processor system 102 for the contiguity analysis. Processor system 102 may implement a user interface for testing user, providing therapy to users, analyzing tests taken by users, plan and or construct a therapy and/or test and/or training regimen for a user. In at least one embodiment, machine system 101 may be configured to size and crop the image to a predetermined size and/or to divide the image into sections and each section may be sized and cropped. The cropping may remove portions of the image or the portions of the image that are not wanted, or edges of the image that cause the image to be too large for generating the composite image, and/or to centralize dominant contiguities and color blocks in the image or in a portion of an image. In at least one embodiment, machine system 101 can be configured to generate an image grid map. The image grid map may be generated, for example, by designating the Cartesian coordinate system to the image designating numerical coordinates of the image. In at least one embodiment, the numerical coordinates may be pixel locations of the image or may be used to construct (and/or define) quadrants, sub-quadrants and/or some other predetermined areas of the image.

Figure 2:
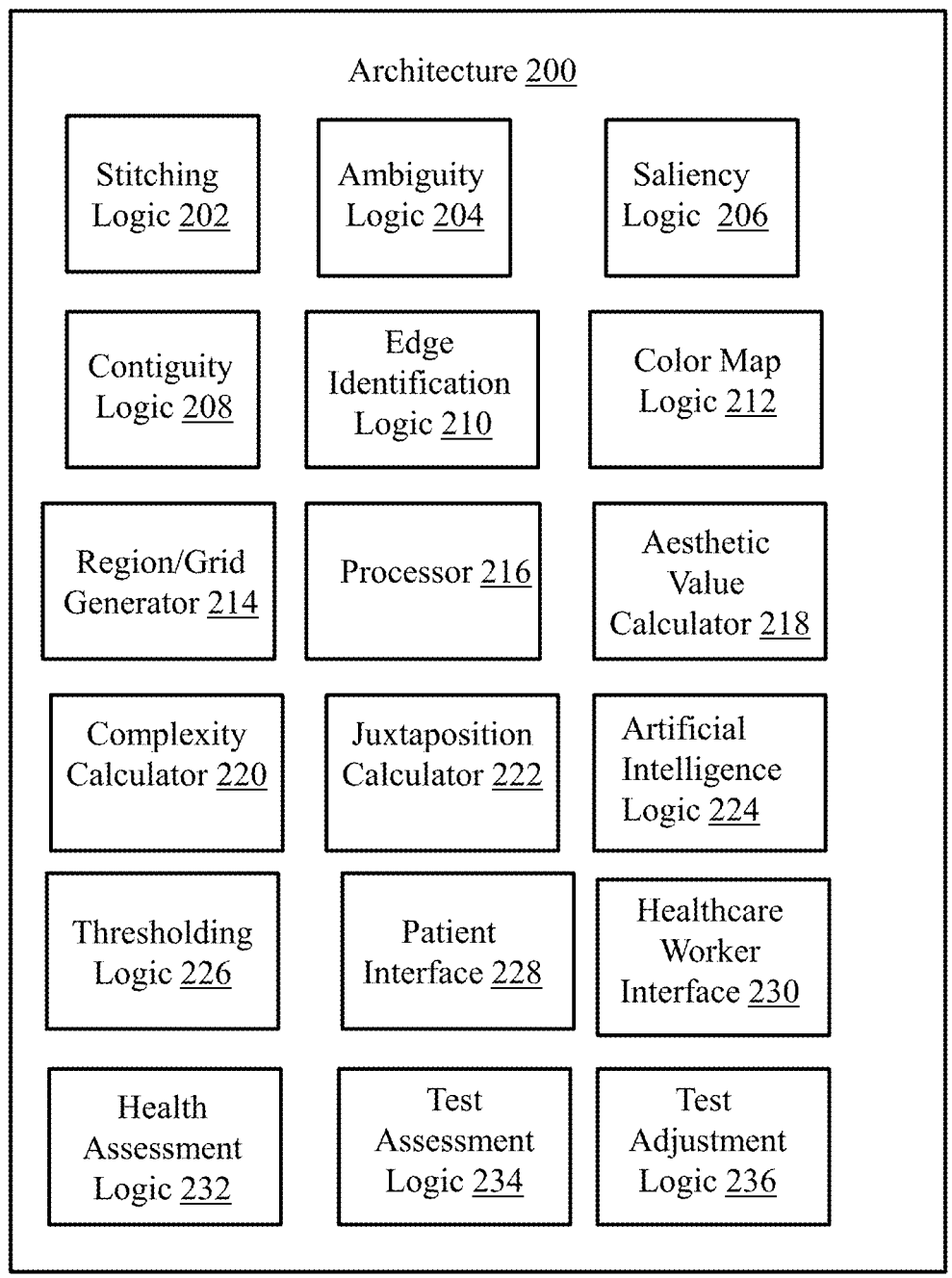
FIG. 2 is a block diagram of an embodiment of the architecture of the machine system of FIG. 1.

FIG. 2 is a block diagram of the architecture 200 of machine system 101, which may be designed to analyze an image and/or create composite images for an interactive cognitive platform. Architecture 200 may include stitching logic 202, ambiguity logic 204, and saliency logic 206, contiguity logic 208, edge identification logic 210, and color map logic 212, region/grid generator 214, processor system 216, aesthetic value calculator 218, complexity calculator 220, juxtaposition calculator 222, the artificial intelligence logic 224, thresholding logic 226, sizing and cropping logic 228, patient interface 229, healthcare worker interface 230, health assessment logic 232 is the logic that correlates the performance and progress of a user with the user's health assessment 232, test assessment logic 234, and test adjustment logic 236. In other embodiments, architecture 200 may include additional components and/or may not include all of the components listed above.

Stitching logic 202 performs the stitching of an image. During the stitching a portion of an image (e.g., one or more horizontal strips) may be removed from the image. After removing the portions of the image, the image may be analyzed, such as by computing the contiguity, and optionally other characteristics of the image, such as the saliency, color block depth, ambiguity, color map, edge detection, color threshold map, brightness and/or threshold map. After removing the portions of the image, and analyzing the image, the portions may be returned. After each portion of the image is restored, the image is again analyzed to determine contiguities, determine contiguity characteristics, perform a multi-contiguity analysis, and optionally determine other characteristics.

Ambiguity logic 204 determines the ambiguity of an image and/or of a portion of an image. The ambiguity is a measure of the degree to which there are elements that may have multiple interpretations.

Saliency logic 206 computes the saliency of an object, image, or portion of an image. The saliency is a measure of the contrast within and between objects or elements. Specifically, the saliency is a measure of internal contrast. Regions of high saliency may be regions that include a foreground type object. In other words, if the saliency is above a predetermined threshold value the saliency may be one or one of multiple factors used to determine whether a region is a foreground object or part of a foreground object. Alternatively, the saliency value may be part of a formula for determining whether a region is part of a foreground object.

Contiguity logic 208 identifies contiguities in an image and/or contiguity lines in an object. Contiguity lines may aid in identifying separate regions that have different meaning from one another, such as separating land from sky, foreground from background, street from buildings, plains from mountains or hills.

Edge identification logic 210 may identify edges in an image. In an embodiment, edge identification logic may divide images into regions that have pixels with brightness values above and below a particular threshold and/or have a wavelength of color within a particular window, to help identify regions in the image. Edge identification logic 210 may also divide regions that are below a particular color threshold. Color map logic 212 maps the color of different regions. The image may be separated out into images of different colors and color maps of the image may be constructed (e.g., a blue image made from the blue pixels of the image, a red image made from the red pixels of the image and a green image made from the green pixels of an image.

Region/grid generator 214 may generate a grid and/or divide the image into multiple regions (e.g., quadrants, halves, thirds, eighths), which may be further divided into sub-regions. The regions, subregions, and grid may be used to identify the locations of elements in an image. Processor system 216 may be an embodiment of processor system 102, and may be capable of implementing a stitching analysis, determining contiguities, computing aesthetic value, complexity, and/or juxtaposition of an image and/or portions of an image.

Artificial intelligence logic 224 may be a neural network or other artificial intelligence logic. Artificial intelligence logic 224 may receive a training set of images, and/or stitched images that are associated with the contiguity values, an identification of contiguities, an identification of contiguity lines, an aesthetic value, a complexity value, and/or juxtaposition values, and an identification of objects and/or of object parts in the image. After receiving the training set, artificial intelligence logic 224 may be trained to identify objects based on the stitched images that are associated with the contiguity values, an identification of contiguities, an identification of contiguity lines, an aesthetic value, a complexity value, and/or juxtaposition values, for example. Thresholding logic 226 creates a derived image by setting all pixels above a threshold to one value and below the threshold to another value, which may be helpful in identifying edges and/or other features. Thresholding logic 226 is optional and may be part of edge identification logic 210. Sizing and cropping logic 228 may automatically size and crop the image or portions of the image.

Patient interface 229 is the interface via which the patient (whom may be referred to as a patient user) interacts with the system 200. Patient interface 229 may be used by the patient for taking assessments, which may be in the forms of game, for measuring cognitive ability. Alternatively or additionally, patient interface 229 may be used for providing therapy to the patient (or other user).

Healthcare worker interface 230 is the interface via which the healthcare worker interacts with the system 200 for collaborating with other healthcare workers, reviewing test results and/or progress of patients, and/or for assigning assessment and/or therapy to patients.

Health assessment logic 232 is the logic that correlates the performance and progress of a user with the user's health. Health assessment logic 232 may assess cognitive abilities of a patient and/or progress of a patient in response to a therapeutic treatment (the treatment may be in the form of games played on system 200 by the patient and/or other treatments). Health assessment logic 232 may be based on previous performances by the user, how the user's performance compares with other patients at the same difficulty level, how the user's performance compares with the general public, Test Assessment Logic 234 is the logic that assesses the performance and progress of a patient user in taking a particular test or group of tests.

Test Adjustment Logic 236 is the logic that adjusts the difficulty of the test based on the user's skill level. In some embodiments, the difficulty may need to be increases due to the user becoming more comfortable with the test (becoming an "expert" on the test). In some embodiments, the test difficulty may be reduced because the user is not getting enough of the answers right. In some embodiments, if the user is not getting 50%, 40%, 30% 25%, 20%, 15%, 10%, 5% or less right, and/or if the patient is taking a longer time, by a predetermined threshold (e.g., by 1, 1.5, 2, 2.5, 3, or 3.5 standard deviations) than most patients, for example, the difficulty level is adjusted down. In at least one embodiment, speed and/or accuracy thresholds may be set based on one or more of the following: gender, age, and known cognitive health status. In some embodiments, if the user is getting more than 50%, 40%, 30% 25%, 20%, 15%, 10%, 5% right, and/or if the patient is taking a less time than an average person by a predetermined threshold (e.g., by 1, 1.5, 2, 2.5, 3, or 3.5 standard deviations) the difficulty level is adjusted up.

Figure 3:
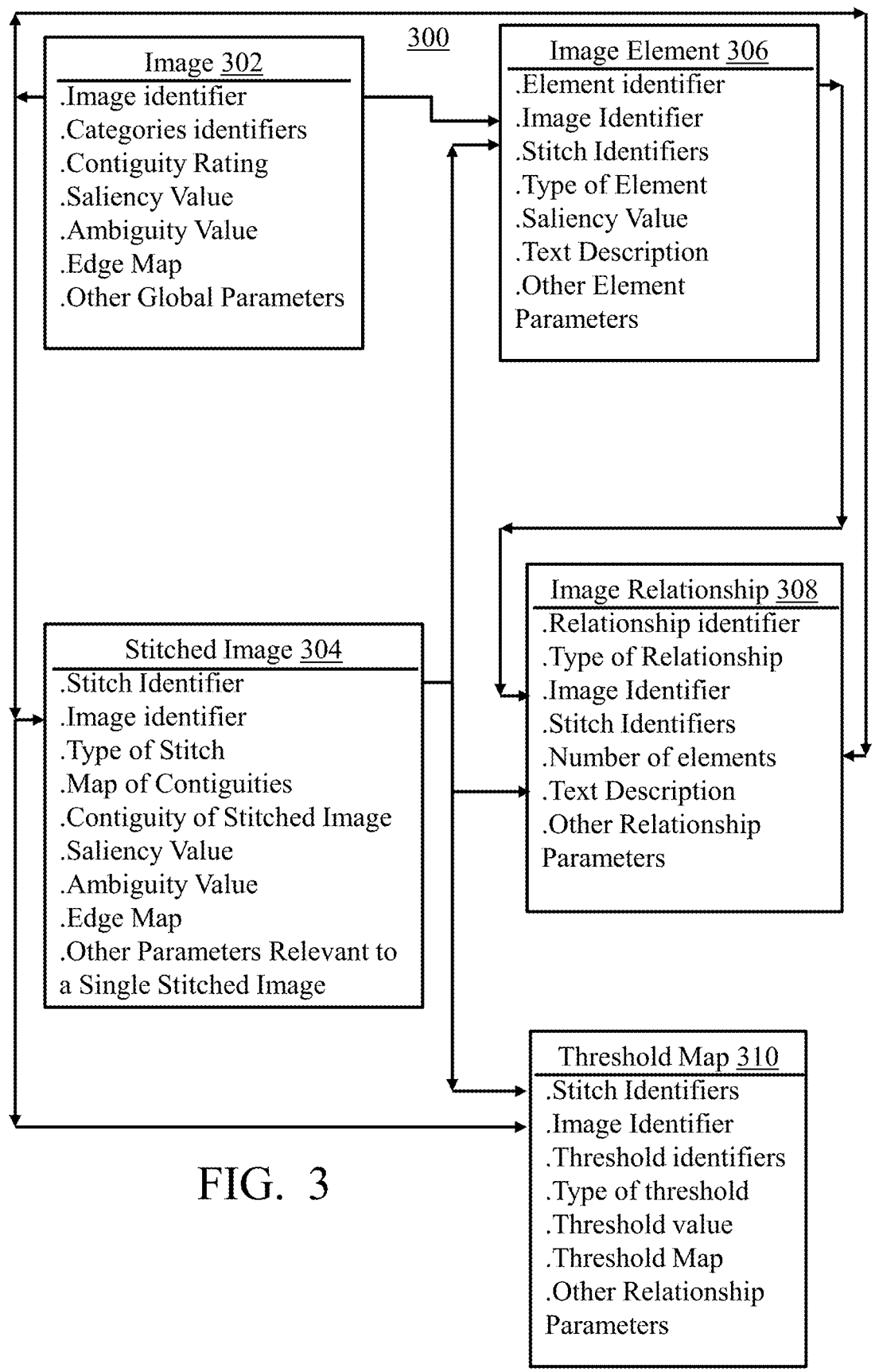
FIG. 3 shows an example of entity relationship diagrams of an embodiment of a database schema of the system of FIGS. 1 and 2.

FIG. 3 shows an example of entity relationship diagrams of an embodiment of a database schema 300 of the system of FIGS. 1 and 2. Database schema 300 may include an image table 302, a stitched image table 304, an image element table 306, a relationship image table 308, and threshold map 310. In other embodiments, database schema 300 may include additional components (such as tables) and/or may not include all of the components (e.g., tables) listed above.

Image table 302 may include various attributes associated with the image. A particular object in a table may be found by searching the attributes of the object. For example, a user may find a particular image by searching for an image having a particular set of attributes. For example, image table 302 may include among its attributes an image identifier, category identifier, a saliency value, and a contiguity rating value (or juxtaposition value), edge map, and/or other attributes such as content and/or color preferences. Image table 302 may also include an edge value, which may be generated by an edge identification table. The image identifier is a primary key and a unique identifier of an image.

Each of the stitched image table 304, an image element table 306, a relationship image table 308, and threshold map 310, have the image identifier as a key, so that each threshold map, image relation, image element may be associated with one image. The stitched image table 304 lists each stitched image of each image. Each image may have multiple stitched images. The attributes of the stitched image table 304 may include the image identifier, stitched image identifier, map of contiguities, stitched image contiguities, saliency value, ambiguity value, edge map, and other attributes. The image identifier identifies the image that the stitched image was generated from, and the stitched image identifier uniquely identifies the stitched image. Stitched image table 304 may also include a type, which describes the type of stitch, which may indicate how much of the image was removed and/or the portion removed. The saliency, ambiguity, and edge map may be the saliency value, ambiguity, and edge map of the stitched image.

Image element table 306 may be a table of elements identified in images. Image element table 306 includes an image identifier identifying which image the element was found in, and an element identifier identifying the element. Image element table 306 includes an image identifier, relationship identifier, stitched identifier, type of element, text description, and/or other attributes. Image element table 306 may include a descriptor that identifies any relationship that involves the element. Image element table 306 may include a type of element that describes the type of element.

Relationship table 308 may be a table of relationships identified in images. Relationship table 308 includes an image identifier, relationship identifier, stitched identifier, type of relations, text description, number of elements and other elements. The image identifier identifies which image the relationship was found in, and the relationship identifier uniquely identifies the relationship. Relationship table 308 may include a descriptor that identifies any objects in the image that are related by the relationship.

Threshold map table 310 may be a table that lists all the threshold maps. The attributes of threshold table 310 may include a relationship identifier, stitch identifier, type of threshold, threshold value, threshold map. The image identifier identifies the image from which the threshold map was created, and a threshold map identifier identifies the threshold map. The type of threshold indicates the type threshold, such as whether the threshold map is a black and white threshold map or color threshold map. Threshold attribute is the value used as the threshold for making the threshold map.

FIGS. 6-7 provide methods for performing contiguity analyses for use in cognitive platforms. Images can be analyzed using manual and/or automated methods to derive Ambiguity and Aesthetic values based on one or more dominant image contiguities. Contiguity analysis can be conducted for both online and offline components of the platform as the images can be printed from digital files. The digital files can be used by the platform and/or transferred to a medium or a substrate such as paper, metal, and wood. Data based on a manual analysis of contiguity characteristics can be entered manually into the digital platform or using a hybrid system of manually entering data using a series of prompted fields with a stylus or other marking device, and where the data is attached to the image and used to calculate Ambiguity, Aesthetic and Compositing Factor values for each image (and Saliency values as a subset of Ambiguity Factors (AF1, AF2, AF5, AF6). The automation of the process facilitates deriving the Compositing Factor for 2- and 3-image composited images whether as part of the digital platform or if used with offline components in assigning skill levels to image sets.

Figure 4:
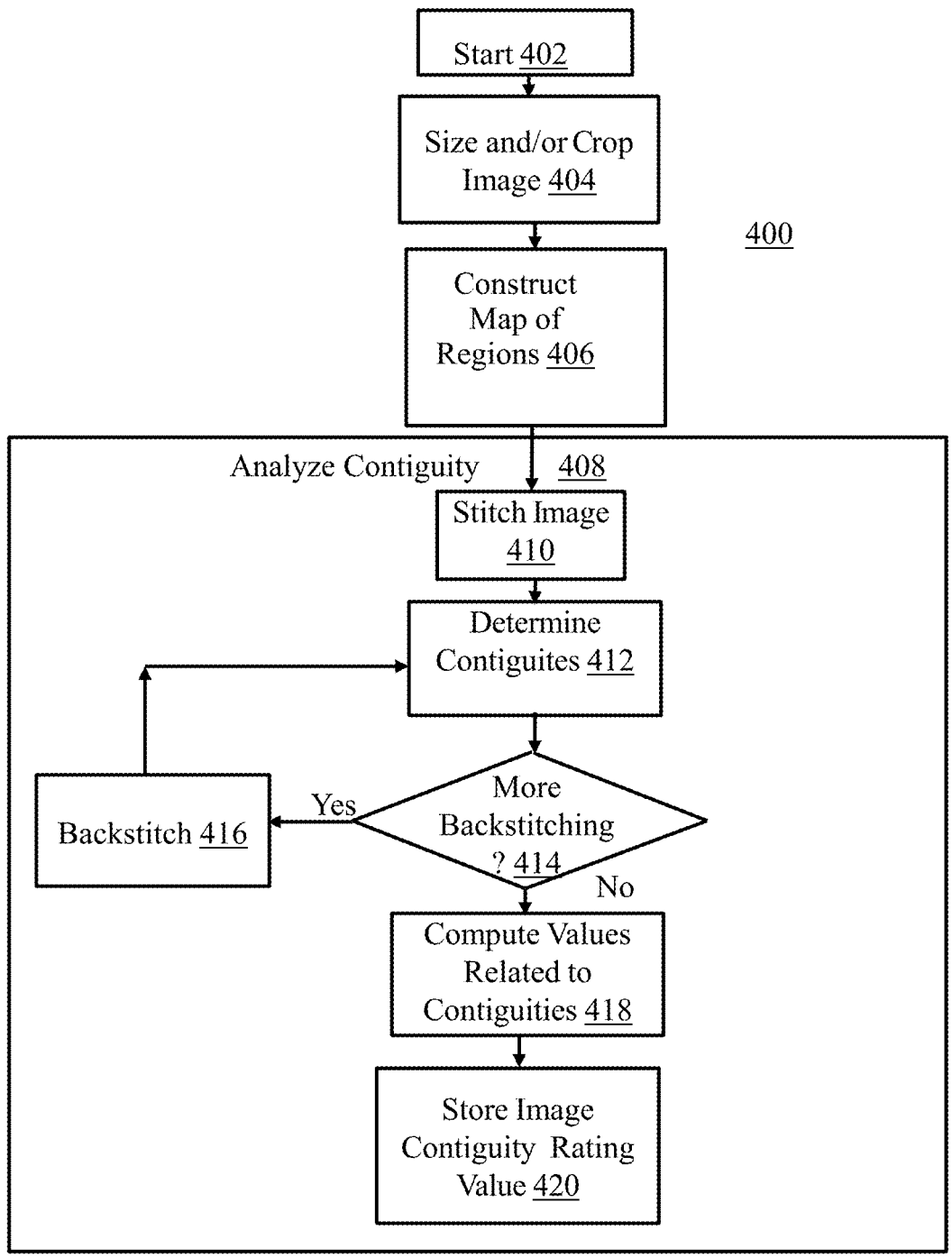
FIG. 4 shows an example of a flowchart for performing a contiguity analysis of an image for a multi-purpose interactive cognitive platform.

FIG. 4 shows an example of a flowchart 400 for performing a contiguity analysis of an image for use in interactive cognitive platforms. In step 402, method 400 starts. For example, in step 402, one or more images are received, retrieved, captured, taken and/or formed, via processor system 102 and/or communication interface 112.

In step 404, the image may be sized and cropped (step 404 is optional), via processor 112 and/or sizing and cropping logic 228. In other words, the image may be enlarged or reduced and/or edges may be removed by processor 112 and/or sizing and cropping logic 228. In at least one embodiment, machine system 101 may be configured to size and crop the image to a predetermined size. The cropping may remove portions of the image that are not wanted, or edges of the image that cause the image to be too large for generating the composite image, and to centralize dominant contiguities and color blocks.

In step 406, a quadrant map and an image grid map are generated, via region/grid generator 214. In at least one embodiment, machine system 101, via region/grid generator 214, may generate a quadrant map, which can equally divide the image into quadrants spanning the entire area of the image (or into another number of regions, such as halves, thirds, fifths, sixths, eighths, etc. In at least one embodiment, the quadrants can be arranged along a Cartesian coordinate system including an X-axis and a Y-axis, in which the center of the Cartesian coordinate system can be predetermined according to predetermined parameters, such as position of dominant content, color blocks, and/or the like. The dominant content may be content that occupies either a majority of the image or a greater portion of the image than other content identified. For example, a single contiguity that is larger than all other contiguities may be the dominant content. In other embodiments, other coordinate systems may be used, such as polar coordinates, hyperbolic coordinates, elliptical coordinates, etc.

In at least one embodiment, machine system 101, via region/grid generator 214, may be configured to generate the image grid map. The image grid map can be generated, for example, by designating the Cartesian coordinate system to the image designating numerical coordinates of the image. In at least one embodiment, the numerical coordinates can be pixel locations of the image or can be used to construct quadrants or some other predetermined areas of the image. The coordinates generated by region/grid generator 214 may be the pixel coordinates or may be the pixel coordinate plus (or minus) an additive constant and multiplied (or divided) by a scaling factor. In at least one embodiment, machine system 101, via region/grid generator 214, is configured to generate a measurement area within the image grid map. The measurement area may be designated as a predetermined area of the image grid map in which the contiguity characteristics may be identified. In at least one embodiment, the measurement area enables identification of objects in the image.

In step 408, the contiguities of the image are analyzed, via contiguity logic 208. In at least one embodiment, machine system 101, via contiguity logic 208, is configured to analyze the image to identify contiguities in the image. In at least one embodiment, the contiguity of the image can include contiguity lines, e.g. the edges that separate different regions of the image according to color differences between the areas, color combinations, and/or the like. The identification of the contiguities may be performed by identifying edges and/or regions having a uniform coloring and/or brightness (within a predetermined threshold). In at least one embodiment, the contiguities can enable a viewer of the image to identify objects, backgrounds, foregrounds, or the like in the image. The contiguities may appear in different locations within the image according to the visual content of the image, image set, or image scene comprised of at least one image. Optionally, the contiguities are identified, via contiguity logic 208, prior to performing any of the substeps of step 408. Contiguity logic 208 may call edge identification logic 210 and/or thresholding logic 226 to assist in identifying contiguities.

In step 410, one or more images are stitched, via stitching logic 202, by removing one more parts of the image. Optionally, the parts removed may be rectangular sections stretching from the top of the image the bottom of the image. For example, the middle third of the image may be removed.

In step 412, the contiguities of the stitched image are identified and/or analyzed, by contiguity logic 208. Contiguity logic 208 may call stitching logic 202 to facilitate identifying contiguities. The stitching may further facilitate determining contiguities (that were not previously identified) and determining objects that interfere with the contiguity, breaking up the contiguities. Color blocks that have similar color but different colors may create object interference—interference that make it difficult to distinguish the border between two or more objects. Stitching and peeling (via stitching logic 202 and/or contiguity logic 208) may facilitate identifying two separate contiguities and/or separate objects despite the object interference and may help bracket the location of a border between where two color regions and/or two objects. In at least one embodiment, the stitch analysis may include masking and progressively peeling portions of the image to enable analyzing a reduced portion of the image to enable defining contiguity characteristics, e.g. contiguity lines, horizon lines, interfaces breaking up the lines, linearities, continuities, regularities, object locations, for example. The steps for angularities, stitching and peeling are discussed further below.

In step 414, a determination is made whether predetermined criteria are met indicating to backstitch the image. For example, in an embodiment, a determination may be made whether the image has been backstitched and, if the image has not been backstitched, whether the image should be backstitched. In another embodiment, the user may enter input that indicates whether to backstitch the image, and if it is determined that the input indicates that the user wants the backstitching to be performed, then it is determined that the backstitching is desired. If it is desired to backstitch, the method proceeds to step 416. In step 416 the image is backstitched. Optionally, each time step 416 is performed a fraction of the image that was previously removed (or masked) is put back into the image (or unmasked). After step 416, the method returns to step 412, where the backstitched image analyzed (e.g., for contiguities). Steps 412, 414, and 416 may be performed multiple times, until all of the backstitching desired is performed.

In at least one embodiment, machine system 101, can be configured to perform the serial backstitch to an image, set of images, or a scene within an image. The serial backstitch may compress the contiguity edge analysis by arranging in an adjacent manner the non-adjacent sections of an image. The serial backstitch can be configured to compress the image on which the contiguity and/or edge analysis is performed by bringing together non-adjacent sections of the image.

Returning to step 414, if all the backstitching needed has been performed, the method proceeds to step 418. In step 418, the computations of the multiple implementations of step 416 are combined. For example, the values representing the contiguity characteristics that were determined in each backstitch are averaged by the total number backstitching steps 416 were performed. The backstitching and evaluation of contiguities is discussed further below.

In step 420, an image contiguity rating ("CR") value (ambiguity value, or juxtaposition value) is stored in association with the image. In this specification the terms juxtaposition value and contiguity rating value and ambiguity value are used interchangeably. Throughout this specification either term may be substituted for the other term to obtain different embodiments. The locations of the contiguities are also stored in association with the data, for further analysis of the image. In at least one embodiment, machine system 101 can be configured to store the image CR value. The image CR value can include a rating that enables machine system 101 to determine an image compatibility for use in generating the composite images. Composite images may be a combination of multiple images. For example, two or more images may be interwoven with one another to form a composite image. The image CR value may be based on multiple parameters, such as the definiteness of the contiguity in the image (e.g., how much contrast exists between the contiguity and surrounding regions), the number of contiguities identified in the image, spatial distribution of the contiguities, the width of the contiguities, the color composition of the contiguities, and/or the angularity of the contiguity (that is, the angularity is the angle at which contiguity is oriented—a larger angle between the horizontal axis and the contiguity may detract from the contiguity and therefore lower the CR, in a convention in which a higher CR value represents more contiguities with a higher distinctiveness of individual contiguities, where viewed in isolation of the other contiguities).

Figure 5:
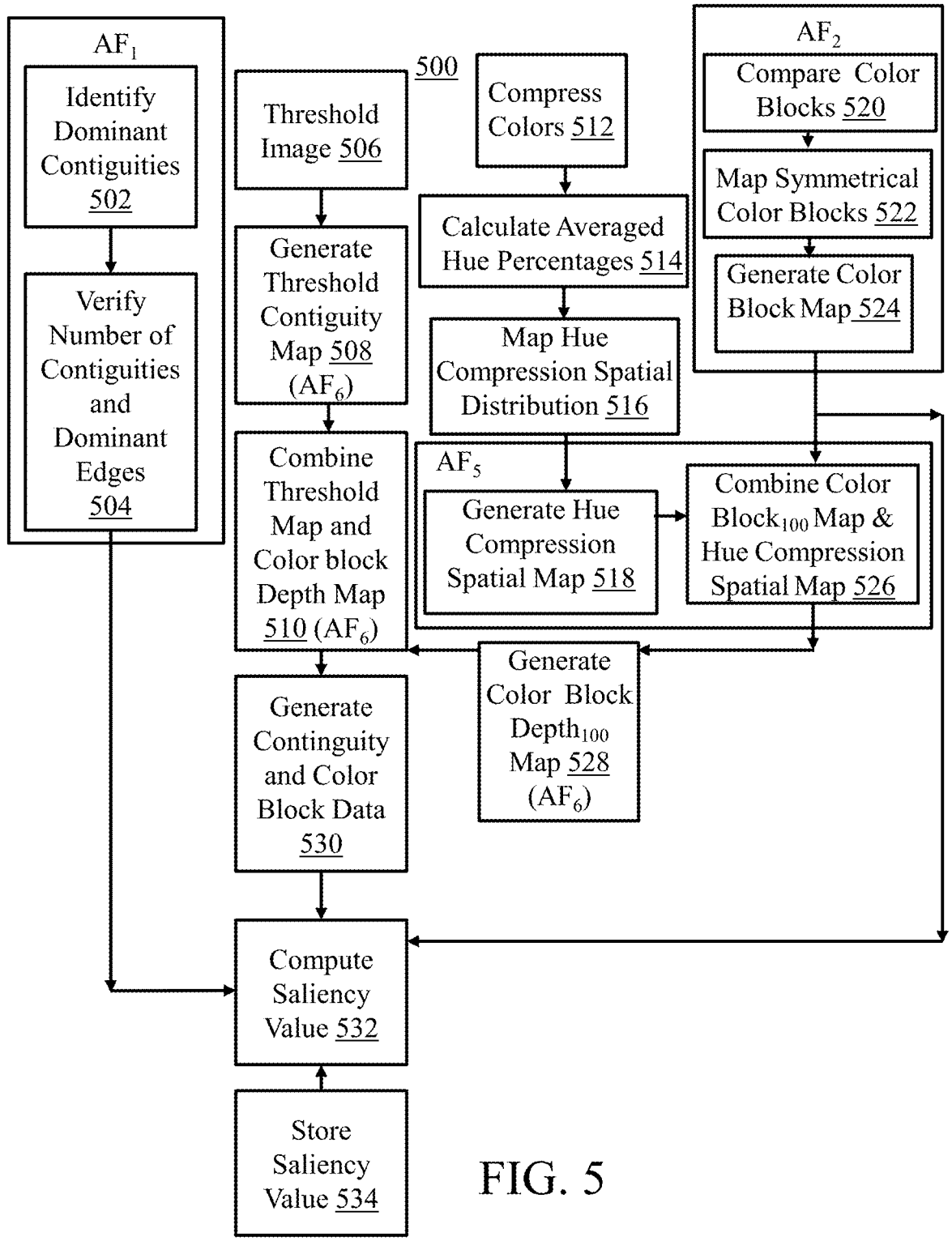
FIG. 5 shows an example of flowchart of an embodiment of a method for computing parameters associated with contiguities and/or contiguity lines for a multi-purpose interactive cognitive platform.

FIG. 5 schematically illustrates a method 500 for generating a contiguity rating value and other related parameters for use in cognitive platforms. In step 502, dominant contiguities are identified by edge identification logic 210. In at least one embodiment, machine system 101 is configured to identify dominant contiguities. The dominant contiguities can be identified, for example, implementing Sobel filters to the image, or another edge identification method, and then using the edges to determine the size and distinctiveness of each contiguity. The dominant contiguities can be determined by the edges of the image as well as the color blocks in the image. For example, each contiguity may be assigned a score. In an embodiment, a contiguity that includes a dominant edge is a dominant contiguity. Dominant edges are dominant contiguities, but not all dominant contiguities may not be dominant edges as a contiguity can also be a color block.

Continuing with the description of step 502, in step 502, the total number of contiguities and dominant edges are also identified in the image. In an embodiment, a dominant edge is an edge that extends across at least a majority of the image. In an embodiment, a dominant edge is an edge that is longer than the majority of other edges. In an embodiment, a dominant edge is an edge that is longer than the majority of edges and extends more horizontally than vertically, and/or extends diagonally. In an embodiment, a dominant edge-type contiguity would extend horizontally across 75% or more of the image. In at least one embodiment, machine system 101 is configured to verify the total number of contiguities, which include the dominant edges in the image, which may be in any direction. The dominant edge can be determined by performing a corner and border identification of the image and identifying edges between color blocks that are above a predetermined contrast and/or threshold level. A dominant edge can have a CR value between 0.75-2.25. In at least one embodiment the dominant edge/contiguity is the edge/contiguity that is used for making measurements, and which contributes to the image's switch capacity. Optionally, a dominant edge has a contrast between adjacent regions that is above a predetermined threshold. For example, in an embodiment, a dominant edge has a contrast of at least 8:1, at least 10:1, at least 20:1, or at least 100:1.

In step 504 thresholding is performed by threshold logic 226. Thresholding logic 226 may form a binary image by setting pixels of the original image above the threshold to white (or black) and the pixels below the threshold being set to black (white). The threshold may be for brightness, a particular color, and/or hue. In at least one embodiment, machine system 101, by thresholding logic 226, may be configured to apply a threshold filter function to the image. The threshold filter function of thresholding logic 226 may aid in partitioning the image into foreground and background parts. The thresholding of thresholding logic 226 may be based on a particular reduction of the colors in the image. The reduction of the color in the image may be performed by representing a color that is not in the color palette of the machine that made the image with the closest color in the palette and/or a dithering pattern of the close colors. The threshold filter function of thresholding logic 226 may generate a binary image of the image to enable edge recognition or detection between the foreground, the background, and/or objects in the image, for example. The terms recognition and detection are used in interchangeably throughout the specification. Throughout this specification, each may be substituted for the other to obtain different embodiments. The threshold filter function may include computing, by thresholding logic 226, a histogram, and clustering the colors into bins and setting the threshold, so as to operate between two clusters of bins. Thresholding logic 226 may choose the threshold based on color, hue, or brightness level that divides between colors, hues or brightnesses that are associated with different levels of entropy (e.g., perhaps pixels having a brightness of above 200 are associated with regions having more entropy than those below the threshold and so the binary image is formed with the threshold set at a brightness of 200). The threshold of thresholding logic 226 may be set based on an object attribute. For example, pixels that are known to be associated with a particular attribute or interest (e.g., an object of interest) tend to have a particular color or brightness and so the threshold may be set and a color or brightness above or below that particular color. The threshold of thresholding logic 226 may be based on spatial filtering. For example, certain regions of the image may be removed from the image, prior to setting the threshold. In at least one embodiment, a multi-level thresholding filter can be implemented by thresholding logic 226 to designate a separate threshold for each of the red, green, and blue components of the image, which can then be combined, for example. Alternatively, multiple brightness thresholds may be set by thresholding logic 226 to produce multiple binary images.

In step 506, thresholding logic 226 may generate a threshold-spatial map (which may be referred to as a T-spatial map). The threshold spatial map stores the locations (e.g., the pixel coordinates of each pixel of the original image that has a value above a threshold and/or each pixel of the original image that has a pixel blue below a threshold may be stored as the T-spatial map). In at least one embodiment, machine system 101 can be configured to generate, by thresholding logic 226, the T-spatial map, for example, by implementing a threshold filter to the image. The application of the T-spatial map to an image helps define edges, contiguities, and dominant contiguities. The line in the image that divides between regions of the image having the pixels that are above and below the threshold may be and/or may be related to edges, contiguity lines, and dominant contiguities in the image. Similarly, the regions having pixels of one of the two types, may be contiguities or may be parts of contiguities (depending on the size and shape of the region, whether the region is identified as being part of a larger region and/or other characteristics of the region).

In step 512, color hues are compressed, by color map logic 212. The compression of the colors may involve, for each pixel determining which of a predetermined number of colors the pixel of the original image is closest to. In at least one embodiment, machine system 101 can be configured to compress the color hues. The color hue compression may reduce the colors in the image to a predetermined number of colors, for example, to a number of colors that is within a range of 2-6 colors, for example.

In step 514 the averaged hue percentages are computed, by color map logic 212. For example, for each of the predetermined colors the percentage of the total number of pixels in the image that are binned with (closest to) one of the predetermined colors. Thus, if one of the colors (e.g., red) has 2500 pixels associated with that color and the image has 1096×1096 pixels, then there are 2500*100%/(1096×1096)=0.2% red pixels. In at least one embodiment, machine system 101 can be configured to calculate, via color map logic 212, the averaged hue percentages. Optionally, a map is constructed having the pixel locations (e.g., pixel coordinates) of each color. The averaged hue percentages of the colors may be identified in the image locations.

In step 516, the hue compression ("HC") spatial distribution is mapped by the color map logic 212. In at least one embodiment, machine system 101 may be configured, by the color map logic 212, to map the hue compression spatial distribution. In other words, the probability of a pixel having a particular color being in a particular region is computed (e.g., as the percentage of the pixels in a particular region having that color). The HC spatial distribution can be correlated to location according to a higher-order probability distribution and/or correlation between the pixels of the image and the location of the colors in the image. The higher order probability refers to other information that may skew the probability distribution. For example, perhaps, as a result of binning the pixels, it is known that 30% of the pixels are blue. Perhaps, as a result of user input, prior images, a category to which the image belongs (or other information), it is expected that the image includes a region in the upper half of the image representing the sky, and as a result, based on prior images there, is a 90% chance of a blue pixel being located in the upper half of the image and only a 10% chance that a blue pixel is located the lower half of the image. Then for this image, there is a 27% chance that pixels in the upper half of the image are blue and 3% chance that pixels in the lower half are blue. The likelihood of a particular pixel being a particular color, depending on where the pixel is in the image, may be affected by the context, saliencies, and a knowledge reference matching pixel distribution (that is, based on prior distributions of the pixels of prior similar images).

In step 518, a hue compression spatial map may be generated by color map logic 212. In at least one embodiment, machine system 101 can be configured to generate the hue compression spatial map. The hue compression spatial map provides a mapping of the colors provided through the hue compression. As part of step 518, color map logic 212 may compute the locations of color blocks (each color block has the color of the average of the color of the block or the hue with the most pixels in its bin). Optionally, each block of a grid is overlaid on the image and is assigned its average color as the color of that block, by color map logic 212.

In step 522 color blocks are compared to one another, by color map logic 212. In at least one embodiment, machine system 101 can be configured, by color map 212, to compare the color blocks, which may determine different color blocks in the image and may determine similarities and dissimilarities within and across the image grid map. Regions of color blocks (where each region is a group of adjacent blocks of the same color) may be compared according to different quadrants in the image grid. The comparing of the color blocks may be in order to determine the different values. For example, in a black and white image, the color block comparison can differentiate between colors having a binary value of zero for white color blocks and a binary value of one for black color blocks. In a second example, the image may include color blocks such as green and blue, where each color is represented by a distinct value, which enables comparing the color blocks within the image grid map.

In step 524, symmetrically-placed color blocks may be mapped by color map logic 212. In at least one embodiment, machine system 101, by color map logic 212, may map color blocks that have a symmetrical shape. Machine system 101, by color map logic 212, may determine that the color blocks are symmetrical according to the pixel location or the location within the grid of the color block pixels on the image grid map and may evaluate the asymmetry of a color block, by color map logic 212. In at least one embodiment, the number of grid boxes of the color block on the image grid map may be compared, by color map logic 212, to determine the edges of a region having adjacent block of the same color to determine whether the region of having a group of color blocks of the same color is symmetric, across and within the region of the color blocks of the same color, and may be compared to color block depth$_{ST}$ (CBD$_{ST}$) data obtained as being symmetrical or showing symmetrical color characteristics, such as blue hues in a region of sky. The "ST" in the subscript of the term "color block" stands for the word "stitch," and the number "ST" indicates the percentage of the total image that remains after the stitching. For example, color block depth67 means a color block value performed in an image that was stitched by removing ⅓ of the image leaving ⅔ of the image and the value assigned according to rules described in FIG. 11B. The shape of the region of blocks having the same color may be indicative of an underlying contiguity and may place limits on the size and shape of the underlying contiguity. Using the bins, the color block depth may be computed. The image is divided into four blocks, where each block is a quadrant of the image. For each quadrant the color with the most pixels in that color's bin is determined, and that is the "color mode" for the block (the "color mode" of a block is the color—of the 2-6 colors into which the image is mapped that occurs most often in that block). If all four quadrants have the same color mode, the color block depth is 1. If two adjacent blocks have one color mode and the other two adjacent blocks have another color mode, the color block depth is 0.75. If two adjacent blocks have one color mode and the other two blocks have each have a color mode different from one another and different from the first two blocks, the value is 0.5. If two nonadjacent blocks have one color mode and the other two nonadjacent blocks have another color, the color mode block depth is 0.5. If all quadrants have different color block modes, the color block depth has a value of 0. If two nonadjacent blocks have one color mode and the other two blocks each have a color mode that is different from one another and different from the first two blocks, the color block depth is 0. Each quadrant may be further subdivided into quadrants and a color block depth may be computed for each quadrant. The color block depth may be computed for different degrees of the stitched or backstitched image.

In step 526, a color block depth 100 (CBD$_{100}$) map is generated by color map logic 212. In at least one embodiment, machine system 101 can be configured to generate the CBD$_{100}$ map. The image may be divided into a predetermined number of blocks. Quadrants that can be defined as positive and negative values arranged on the Cartesian coordinate system or with a numerical label, Q1, Q2, Q3 and Q4. The number of color block patterns identified by machine system 101, in each quadrant, relative to other quadrants in the image can provide a relational analysis of different color portions of the image, their distribution and symmetry, and which can be mapped onto the grid of the map to generate the CBD$_{100}$ map. The nuanced differences are regions which are subjected to further analysis. As quadrants are drilled down into sub-quadrants (and sub-sub-Qs) is where CB differences become more evident allowing for the identification of IE and VD. Each quadrant may be analyzed individually, and any quadrant that has features that correspond to something of interest may be further divided into quadrants (or other sectors) and analyzed individually and each sub-quadrant, having features corresponding something of interest may be further subdivided and analyzed individually. The process of identifying sectors having features corresponding to something of interest and then further subdividing those sectors may be continued until there are two few pixels in the sectors with which to make further analysis (e.g., when each sector only has one pixel).

The values for CBD$_{100}$ are based on the rules which will be described, below, in FIG. 11B. The color block map of the original intact image and the various stitched images may be compared and the characteristics of the image derived from the color maps from each stitch may be averaged.

In step 528, the hue compression spatial map and CBD$_{100}$ map are combined (e.g., integrated or superimposed on one another, so that one map appears foreground and the other map appears as background). In at least one embodiment, machine system 101 combines the hue compression spatial map and the CBD$_{100}$ map. The hue compression spatial map generated from the threshold function may be aligned with the CBD$_{100}$ map to provide a unified map for recognizing the necessary edges for designating the contiguities in the image based on the color composition. The combined hue compression spatial map and CBD$_{100}$ map may be used to maintain the embedded color information of the image.

In step 530, a CBD$_{100}$ is generated in at least one embodiment, machine system 101 can be configured to generate the CBD$_{100}$, which is the composited map including the overlaid information obtained by aligning the hue compression spatial map and the CBD$_{100}$ map.

In step 532, the T-spatial map and the CBD$_{100}$ are combined. In at least one embodiment, machine system 101 can be configured to combine (e.g., integrate) the T-spatial map and the CBD$_{100}$.

In step 534, a contiguity number (or value) is generated by contiguity logic 208. Color block data and spatial data may also be generated by contiguity logic 208, as part of step 534. In at least one embodiment, as part of step 534, machine system 101 may generate the contiguity number, the color blocks and the spatial data. The contiguity number may be the number of contiguities designated in the image based on predetermined parameters (e.g., based on predetermined thresholds for threshold maps and predetermined number of stitches and peels, are predetermined set of bins of hue, and predetermined grid, and block size for the blocks of the regions of color blocks having the same color).

In step 536 an image saliency value is generated. In at least one embodiment, machine system 101 can be configured to generate the image saliency value. The image saliency value provides a unique quality for a group of pixels or for a single pixel relative to surrounding pixels and the rest of the image, and enables easier analysis of the image. In one embodiment, the saliency is represented by a combination of contiguity factors including: contiguity number, number of color blocks, color block depth 100, and the spatial color contiguity comparison. Regions where color or brightness differences may be present are identified by the differences in the distribution and the number contiguities and color blocks in an image.

The image saliency value sets a contour for extracting information from the image to enable edge detection, e.g. each pixel in a region that is similar with respect to a predetermined characteristic or computed property, such as color, intensity, texture or the like. In other words, since the saliency value is an indication of whether a particular region is of interest (e.g., as a result of having a different color, brightness, texture, and/or other characteristics than neighboring regions) if the saliency value crosses a particular threshold value the region may be further analyzed to determine characteristics of sub-regions with the region of interest. In this specification, the words brightness and intensity are interchangeable, either may be substituted for the other wherever they occur to obtain different embodiments.

In step 538, the saliency value is stored in image database 110 and/or passed on to other methods that make use of the saliency. The image saliency value, which is a measure of internal contrast, contributes to the dominance of a subset of image characteristics defined in part or whole by continuous and/or a contiguous group of color blocks of recognized elements and their corresponding juxtapositions (or Contiguity Rating-CR values), or as defined by the shape of the group of color blocks. As will be discussed further below, the ambiguity value is given by $\text{Ambi}_{SAL} = \Sigma(AF_1 + AF_2 + AF_5 + AF_6)$.

$AF_1$, $AF_2$, $AF_5$, and $AF_6$ are discussed further below, and the steps of FIG. 5A that compute each ambiguity factor is indicated in FIG. 5A. In an embodiment, if $\text{Ambi}_{SAL} < 5.5$, the images contains a significant amount of nuanced or poorly defined distractions—no clear attention focus, save for the contiguities present in the image. Images in this category can be used to focus on nuanced details as an attractor and/or distractor element. If $\text{Ambi}_{SAL}$ is between 5.5-14 then there is a balanced color blocking and contiguity/edge sharpness (an optimal range for looking at details in an image and/or for focusing on a particular object or element in the image. If $\text{Ambi}_{SAL} > 14$, the image contains a significant number of discontinuous contiguities, little or no color symmetry, and the objects may be disrupted; there are lots of parts to look at. Images in this category can be used to focus on nuanced details as attractor and/or distractor element).

Figure 6A:
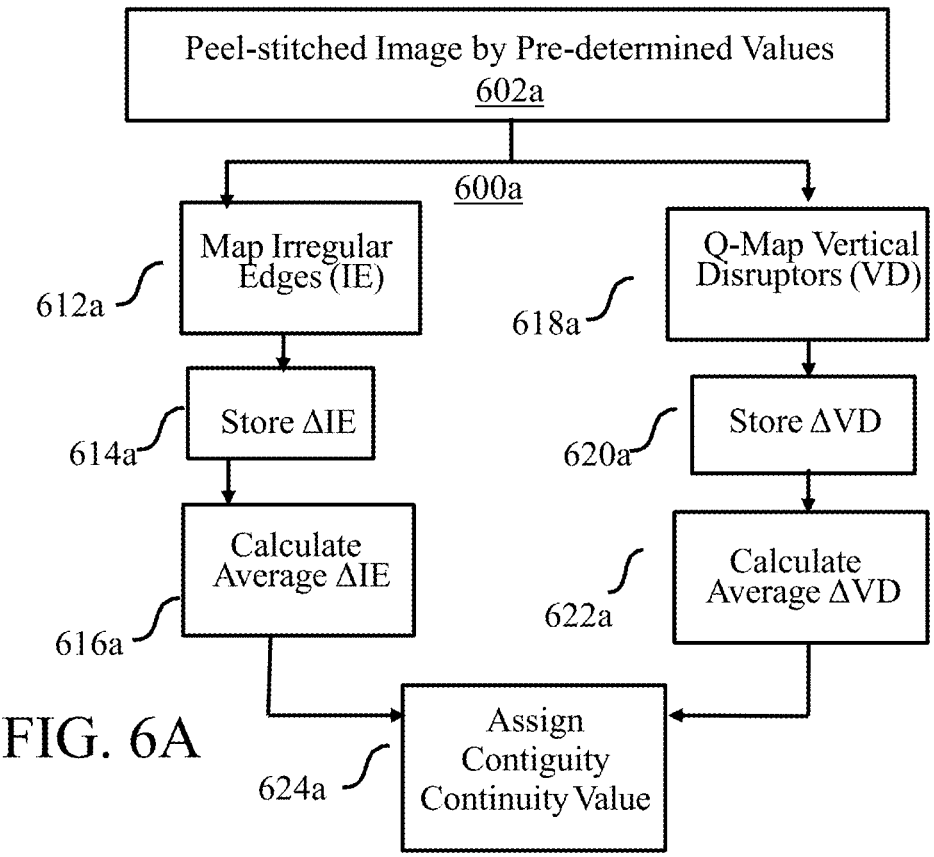
FIGS. 6A and B show an example of a flowchart of a method of computing contiguity continuity values using a stitched image for a multi-purpose interactive cognitive platform.

FIG. 6A schematically illustrates a method 600a of peeling, according to at least one embodiment for use in cognitive platforms. In step 610a, peeling operations are performed at predetermined values, such as predetermined percentages of stitching and/or peeling. In at least one embodiment, machine system 101 can be configured to peel a first section (e.g., a first 30% of the image), and then a second section at the predetermined values (a second 30% of the image). Alternatively, the different percentage could be used, such as 25% or 10%.

In step 612a, irregular edges (IE) are mapped. In step 612a, a map of irregular edges is computed. The map may be based on the regions (e.g., quadrants and blocks of the quadrants) of the region map, and the map for each region may be computed. In at least one embodiment, machine system 101 can be configured to map the irregular edges, which can be edges that include shapes, contrast hue, and/or color difference with the surrounding areas. The edge irregularity may be computed by computing differences between edge parameters, such as the differences in the angle, contrast, brightness, color, and hue of the edge. Differences between edge irregularities of different degrees of stitching/peeling and/or thresholding may also be computed.

Using either the original image or the stitched image, deviations off the X-axis relative to the dominant contiguity may be evaluated setting up a grid to define the Intrusion Area, which is the area that the vertical intrusion intrudes into an area above (and/or optionally below) the dominant contiguity. The vertical disruption by a Vertical Disruptor (VD) can be in the contiguity may be objects of interest, and the fact that a region is a vertical disruptor may be used as one factor of multiple factors that indicate that a region is part of an object of interest and/or that the object may be a foreground object. If the suspected IE extends beyond one or more adjacent grid boxes, or extends along the X-axis for 3 or more grid boxes, which for example may be 0.1 inch to ⅛ inch (when the image is viewed in the size that the image will be printed or presented) and/or fills 1 or more grid boxes more than 20% and/or extends beyond the boundaries of one or more grid boxes, the intrusion is evaluated as a Vertical Disruptor. Vertical Disruptors are irregular edges, so all Vertical Disruptors are irregular edges, but not all irregular edges are Vertical Disruptors. In an embodiment, in step 612a, the irregular edges that are not Vertical Disruptors are mapped. In measuring a VD, the size of the boxes should be chosen so that the area of the Vertical Disruptor arrived at by using the number of boxes that the width and height of the Vertical Disruptor fit is within 40% of the area of the vertical disruptor when using the actual height and width to compute the area of the vertical disruptor (as an approximation of the actual area of the vertical disruptor). The area of the intrusion may be computed in other ways (such as by counting the number of pixels used to represent the intrusion divided by the number of pixels in the region that intrusion intrudes into). A stitched image may be used to remove regions known to contain one or more Vertical Disruptor. In step 1, the dominant contiguity is identified on a thresholded or edged image (stitched or original). In step 2, the grid is boxes (or pixels occupied by the intrusion are identified and counted and/or identified. In step 3, intrusion areas are classified as non-regular (irregular) or classified or as Vertical Disruptors depending on the size of the intrusion.

In step 614a, the edge irregularities and optionally the differences in edge irregularities are stored.

In step 616*a*, the average position and/or contour of the irregular edges are calculated. In at least one embodiment, machine system 101 can be configured to calculate the average irregular edges. The average position and/or contour of the irregular edges may be computed by averaging the differences in the edge irregularities (e.g., including one value of no difference corresponding to the baseline value itself), and then adding the average values of the position to the baseline values (of the location and contour of the irregular edges) of the contiguities.

In step 618*a*, vertical disruptors in the contiguity and/or contiguity lines are mapped. In step 618*a*, a map of vertical disruptors is computed as a baseline computation of the position and other parameters (e.g., the contrast or degree of disruption) of the vertical disruptor. In at least one embodiment, machine system 101 may be configured to map the vertical disruptors. The vertical disruptors may be objects or elements identified in the image that extend into a vertical plane from a horizontal line, e.g., from a contiguity. Vertical disruptors are horizontal features that disrupt contiguity lines and/or contiguities. The map may be based on the regions (quadrants) of the region map, and a map for each region may be computed. In at least one embodiment, machine system 101 can be configured to map the vertical disruptors. Differences between the vertical disruptors of different degrees of stitching/peeling and/or thresholding may also be computed.

In step 620*a*, the vertical disruptors and optionally the differences in the positions of the vertical disruptors are stored.

In step 622*a*, an average vertical disruptor may be calculated by averaging the differences in the vertical disruptor (e.g., including one value of no difference corresponding to the baseline value itself) and then adding the average of the differences to the baseline values of the vertical disruptor, and/or the spatial separation between multiple VDs stored. In at least one embodiment, machine system 101 can be configured to calculate the average width span, height and/or density (co-localization) of the vertical disruptors.

In step 624*a*, a contiguity continuity value (CV) is computed (e.g., based on steps 616*a* and 622*a*). In at least one embodiment, machine system 101 can be configured to assign the contiguity continuity value, which is the value assigned to the contiguity and represents the degree to which there are disruptions in the contiguity across the X-axis, e.g., where the X-axis is the horizontal plain of the image. For example, the contiguity continuity value can have a value within a range of −1.0 to 1.0. The contiguity continuity value may be assigned according to the values obtained for the vertical disruptors and irregular edges. For example, where the contiguity extends across the image within a range of 75 to 100 percent, a contiguity value range of 1 may be assigned. Where the contiguity line extends across the image width within a range of 50 to 75 percent, a value of 0 may be assigned. Where contiguity extends across the image within a range of 0 and 50 percent, or the contiguity is zero, a value of −1 may be assigned. In alternative embodiments other values and methods of computing the contiguity continuity may be used. For example, the percentage of the width of the image that the contiguity extends (or the percentage of the width of the image that the contiguity extends minus 50%) may be used as the contiguity continuity value (so that the contiguity continuity value is a continuous variable).

Figure 6B:
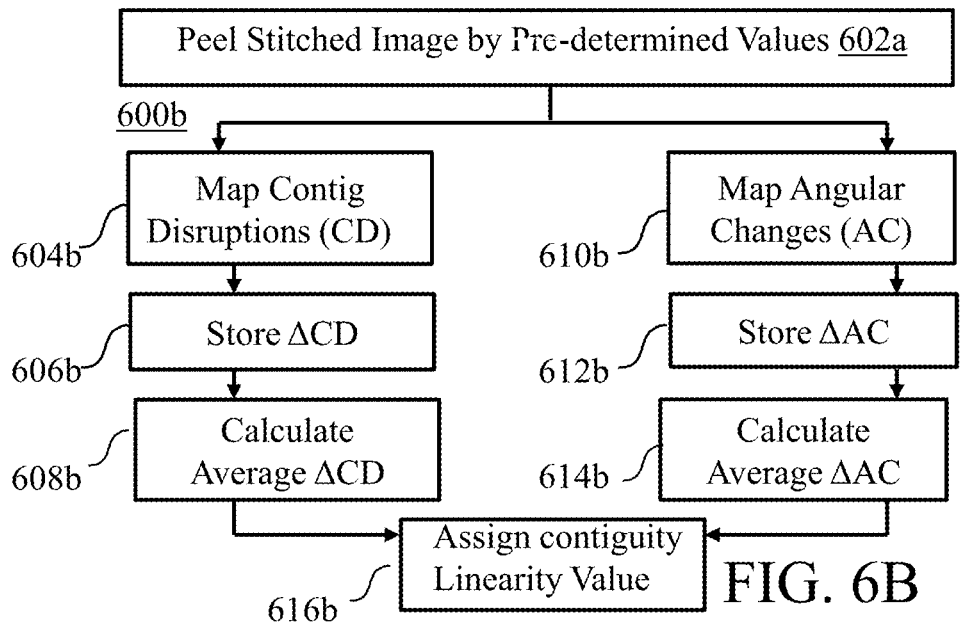

The method of FIG. 6B is part of the method of FIG. 6A. Step 602 of FIGS. 6A and 6B may be the same step.

In step 604*b*, the position and shape (and optionally other parameters) of the contiguity disruptions (CD) are mapped to establish a baseline of the shape, dimensions, and/or position of the disruptions. Contiguity disruptions are breaks or partial breaks into a contiguity. For example, a region in which the width of the contiguity is less than the adjacent regions (e.g., by more than 10% or 15%) may be considered a contiguity disruption (in other embodiments other criteria and/or percentages may be used for determining a contiguity disruption). Note that the terminology used here the length of contiguity extends generally along the horizontal axis or at an acute angle with the horizontal axis of the image, and the width of the contiguity extends along the vertical axis of the image or at an acute angle to the vertical axis of the image. In at least one embodiment, machine system 101 can be configured to map the contiguity disruptions. The contiguity disruptions are mapped to enable machine system 101 to locate the contiguity disruptions in the image, e.g. where there are objects or portions of the image that disrupt the contiguity in the image. The map may be based on the regions (quadrants) of the region map, and map for each region may be computed. In at least one embodiment, machine system 101 can be configured to map the contiguity disruptions, which may also include vertical disruptions in contiguities or contiguity lines. Optionally, differences in one or more contiguity's linearity and continuity may also be computed and compared using different degrees of stitching/peeling and/or thresholding.

In step 606*b*, the contiguity disruptors and optionally the differences in contiguity disruptions are stored.

In step 608*b*, an average contiguity disruption is computed, by averaging the differences in the contiguity disruption (e.g., including one value of no difference corresponding to the baseline value itself) and then adding the average of the differences to the baseline values of the contiguity disruption. In at least one embodiment, machine system 101 can be configured to calculate the average contiguity disruption.

In step 610*b*, angular changes (AC) in the contiguity and/or contiguity lines are mapped, to establish baseline values. In at least one embodiment, machine system 101 can be configured to map angular change of the contiguity line. The angular change (AC) can be the angle at which the contiguity in the image relative to an X-axis (a horizontal axis), e.g., horizontal plain of the image. The map may be based on the regions (quadrants) of the region map, and map for each region may be computed. Optionally, difference between angular changes in contiguities of different degrees of stitching/peeling and/or thresholding may also be computed. In step 812, the angular changes and optionally the differences in angular changes are stored.

In step 614*b*, an average angular change (AC) is calculated, by averaging the differences in the angular change (e.g., including one value of no difference corresponding to the baseline value itself) and then adding the average of the differences to the baseline values of the angular change. In at least one embodiment, machine system 101 may be configured to calculate the average angular change. The average angular change can be the average angular change of the dominant contiguity, another designated contiguity or all contiguities in the image.

In step 616*b*, a contiguity linearity value is computed, which may be based on steps 808 and 814. In at least one embodiment, machine system 101 can be configured to assign the contiguity linearity value, which is the value assigned to the contiguity for a deviation of the X-axis, e.g., horizontal plain of the image. For example, in an embodiment, the contiguity linearity value can have a value within a range of −1.0 to 1.0 and is derived from the average contiguity changes (Step 608b) and angular changes (Step 616b) using measurement boxes, which may be computed in steps 406 (FIG. 4) and/or step 606 (FIG. 6) of Ser. No. 16/427,305. The measurement boxes (or regions of other shapes) may be boxes formed by the grid. The contiguity disruptor and angular change may be computed for each region (in steps 804 and 810) and then the values of each region for the contiguity disruptor and angular change may be averaged over the entire images in steps 808 and 816, and then the two averages (the contiguity disruptor and angular change) may be used to compute the contiguity linearity in step 818. Although in FIGS. 6-8 average values are computed by computing a baseline value and then averaging the differences of subsequent measurements taken at different degrees of stitching and/or thresholding, in other embodiments, the average values may be computed in other ways, such as by remeasuring the edge irregularities, the vertical disruptors, the continuity contiguity, and/or the continuity linearity, and averaging the entire measurement.

In an embodiment, each of the steps of method 600 is a distinct step. In another embodiment, although depicted as distinct steps in FIG. 6, step 610-690 may not be distinct steps. In other embodiments, method 600 may not have all of the above steps and/or may have other steps in addition to or instead of those listed above. The steps of method 600 may be performed in another order. Subsets of the steps listed above as part of method 600 may be used to form their own method.

FIG. 7 provides a method 700 for analyzing the content of images. Sub-library images can contain regional content and/or culturally-sensitive content, and/or images designed to meet a particular cognitive protocol for a subset of users with a particular cognitive profile. Images and image sets can be selected by the system as part of a protocol and/or treatment schema, and/or to assess the user's cognitive status; and/or in the case of a registered user image sets and game boards containing images and image sets can be user-defined (e.g., personalized), based on a set of rules designed to match user interests and preferences to their skill level at a point in time, and through a protocol which defines progressions for users. User activities can be stored so as to retrieve their data and/or to allow for the completion of a saved interactive or for the regimen to progress to the next level according to the user's training and/or therapeutic protocol.

In step 710, an image is uploaded or scanned by a user or healthcare worker. The image can be an image selected by a user to be part of that user's personalized cognitive test, game or interactivity. The user may find the image by searching the internet, or the user may choose a personal image from a photograph, for example, in the user's library. In some embodiments, the user is a healthcare worker who is preparing a cognitive platform configuration to be used for diagnosis, treatment, or research. The healthcare worker may choose the image that is appropriate for a particular patient or group of patients. The image may be described as an image of interest.

In step 720, the image of interest is sized and/or cropped to a predetermined size automatically or by a user. The cropping may remove portions of the image or the portions of the image that are not wanted, or edges of the image that cause the image to be too large for generating the composite image, and/or to centralize dominant contiguities and color blocks in the image or in a portion of an image or other salient features.

In step 730, each image in the library is tagged with descriptive elements. The descriptive elements can define the image's action, content and color; each image can also be tagged with an optional display box which identifies image content. To address non-English speaking users, alternative text labeling in the user's native or preferred language can be included to maximize the value of the interactivity for specific cognitive interventions, language remediation and/or training purposes. The image may be tagged with descriptors with human input to ensure specificity and accuracy, because image programs may not provide sufficient accuracy in generating image captions or descriptions. In some embodiments, once the image of choice is tagged with descriptors, the image is stored in association with its data in the library 780.

In step 740 the contiguity analysis is performed. Each image in the library is ranked according to its complexity based on content complexity and contiguity characteristics among other factors. The impact of contiguities can be seen using a sunflower field example where the field fills the entire frame versus an image where a part of the sky is visible creating a more traditional horizon-type contiguity. This can be viewed as an interface (of field:sky) with a demarcation in both content and color distributed and identifiable as such based on the user's personal knowledge and experience base. Complexity in this sense is a function of the content, its spatial relationship and the presence or absence of contiguity. For example, an image containing a single yellow flower with a brown center framed in a single color background would be ranked as less complex then a field of flowers. This is because the single flower has a stronger contiguity than the field of flowers without a horizon, but the single flower has a weaker contiguity compared to a field of flowers with a horizon-type interface (providing hierarchical relationships to figure-ground positioning of image content based on its contiguity characteristics and in comparing contiguity characteristics to other images when combined into composite image sets (see FIGS. 22A-24C).

As part of the contiguity analysis 740, in addition to assigned attributes, each image in the library is analyzed and assigned aesthetic and ambiguity values based on a subset of image characteristics; and a second value, a Compositing Factor related to combining an image with one or more other images, based on a subset of image characteristics, and is derived in part from the aesthetic and ambiguity values. The ambiguity value is also known as the Complexity Rating (CR) and which is based on contiguity characteristics of at least one dominant contiguity and/or contiguous region which can contribute to the ambiguity and/or aesthetic scoring. The CR value can also be derived for a multiplicity of contiguities contained in a single image for their potential positive and/or negative impact in a composite image construct in terms of the Compositing Factor; the relative negative or positive contribution depends on contiguity characteristics, including: content coherence, context, color composition and spatial separation.

In steps 750, 760 and 770, the CR value, the Aesthetic value, and the Compositing Factor (CGCR) are stored in association with other information about the image. In some embodiments, once the image of choice is provided with a CR value, the image is stored in association with data in the library 780. In some embodiments, once the image of choice is provided with an aesthetic value, the image is stored in association with data in the library 780.

In step 780, the image of choice and the data associated with the image of choice are stored in a library. In some embodiments, the library may be specific to a user, a health-care worker, a disease type, a research protocol, or a testing protocol.

The image library can obtain source materials from artists, which can include: individual photographers, photography groups, painters, illustrators, and other artists; image uploads from specific user groups and/or individuals, including research and clinical administrators, and which can be integrated into user-specific interactivities and/or licensed images from other 3rd party vendors including archives and content providers to meet specific use cases and/or user requirements. The use of library images is tracked internally for inclusion in any of the hands-on, hands-free and/or view only interactivities, including manipulatives as well as printed material as environmental enrichments. The tracking also serves to minimize duplication of content and/or near-content with the use of similar and/or related images and/or associated Word Lists used for assessments. The component tracking system can be used for tracking usage and any remunerations owed to the contributing artist based on previous arrangements and agreements.

In an embodiment, each of the steps of method 700 is a distinct step. In another embodiment, although depicted as distinct steps in FIG. 7, step 710-780 may not be distinct steps. In other embodiments, method 700 may not have all of the above steps and/or may have other steps in addition to or instead of those listed above. The steps of method 700 may be performed in another order. Subsets of the steps listed above as part of method 700 may be used to form their own method.

FIG. 8 provides an embodiment of a method 800 for building a user profile (On-boarding). The platform utilizes puzzle-styled interactivities to engage cognition using images and composited image scenes which portray real-world content. Users engage with images and/or their composites which can be presented as two or three image combinations through a selection of interactivities and which can be rated according to the interactivity, skill level and image complexity, and metered by the cognitive status and/or capacity of the user in developing metrics. Assessments are designed to cooperatively engage processes and skills across multiple cognitive domains. The assessments are embedded in the interactivities themselves, applying a modified "activity is the assessment" model to capture both intra-activity and/or post-activity data. Through combinations of the interactivities, the platform is used to capture a range of data: speed, accuracy measures, reaction time, error type as well as process data inferred by user screen movements/placements and image part selection patterns. Assessments (see FIG. 18 and the Appendix) of cognition may also be based on user activities, prior to performing an interactivity (such as the process of selecting which interactivity the user wants to select or the process of the user reading the instructions and initiating the interactivity) and/or activities performed after an interactivity (such as the process of closing the interactivity, answering questions after the interactivity, and/or logging off the platform). Assessments may be based on multiple activities, designed to target global cognitive functioning while at the same time addressing individual cognitive domain requirements for training and/or remediation purposes.

In step 810 a user is registered. The process of registering may include setting up a login, including a username and password. The platform may include the integration of image-based passwords which can be integrated into a pre and/or post-interactivity assessment. Other information may be included such as information about a user's health, age, medication, and cognitive and physical status. Other information may also include a doctor, clinician, and/or researcher that the user is associated with as well as contact information. In some embodiments, if the user is a health-care worker, information about the hospital, specialty, research subject, education, and registrations may be included.

In step 820 a baseline assessment and health survey is performed. The assessment may include information about the cognitive and physical health of a user, language preferences, and information about diet, sleep and exercise habits, and vision issues. In other embodiments, the information may include a simple test or use of the platform to establish a baseline assessment for the user.

In step 830, the user is assigned a skill level based on the information received in steps 810 and 820. The user (and/or the user's healthcare worker) may review the skill level to identify whether the chosen skill level is appropriate. If not, the user or healthcare workers can re-evaluate the information in steps 810 and 820. The user, as part of step 830, may be assigned a skill level automatically (based on tests) or by a healthcare provider.

However, in some embodiments, as part of step 830, the user may assign him or herself a skill level and/or the skill level may be automatically assigned based on a formula provided by the cognitive platform.

In one embodiment, as part of step 830, each of the skill levels: Easy, Medium and Hard can include an expandable list of sub-levels and interactivities at each sub-level within a given skill level according to a professional or user-defined protocol. Each skill level does not need to have the same number of sub-level interactivities. When a subset of interactive criteria are met at a pre-defined threshold level range—a metric based in part on: time to task completion, correct responses (error rate), time/move, reaction time, combined with post-activityassessments (testing for language, memory and attention) with Word List Recall (WL-immediate, delayed and extended) and SQ2 questions (spatial quantitative, qualitative), Object ID and Dimensional Descriptors, which are designed to evaluate memory, vocabulary, and concepts, together with attention-focusing requirements for object-cued Object ID (OID) and Dimensional Descriptors which uses composite images. The user can be progressed and/or regressed to a sub-level within a skill level and/or the previous/next skill level. The new level possible and/or achieved may be assessed for user consistency and user progression/regression to meet the new requirements and for tracking changes over time. If consistent, the user can engage with the interactivities at or within that skill level until the user reaches a different threshold, and the interactivities and associated metrics of interactivities, number of images, image complexity, sectioning strategy and/or number and size of interactive elements (game pieces) is delivered to the user. Sectioning strategy refers to the shapes of the strips into which the image is cut, typically something that is prescribed to the user, but may be manipulated by the user by choosing different difficulty levels. Sectioning Strategy can apply to the shape of the cut section, as well as the size of the section or part of a section, but primarily refers to the number of slices and width of the section (same or variable) generated from cutting an entire image 25% cuts=4 sections; 20%=5 sections. A sectioning strategy may include the types of sections into which an image is divided into for solving a puzzle. The image may be divided into horizontal or vertical strips and pieced together accordingly. The matching interactivities use whole sections, parts of a section, or can span multiple sections with shape variability of the presented parts. In a FreePlay type of scenario (or other scenario), where the user selects the features of the "game/interactivity," size, number, the percentage of the image that individual pieces make up, and/or the shape of the pieces may all be variable that the user may control. Similarly, in a protocol or fixed progression type of gameplay the variables may be pre-configured and related to skill level and image complexity. Similarly for baseline assessments users can be assigned to a skill level based on age, gender, cognitive status using referenced norms, and adjustments made to the skill level for follow-up assessments as dictated by the user's health/cognitive status, including changes in vision, and fine and gross motor control for example.

For the FreePlay mode, the user may be allowed to override suggested skill levels at defined points in time. For a training mode, any assessments which are not embedded directly in the user data (for example, speed, accuracy, reaction time, movement mapping), and specifically where the user is not required to answer questions after the interactive, can facilitate compliance and data gathering. In some embodiments, FindIT-type games can be integrated into the platform to eliminate voice and/or text-based inputs both under FreePlay, and also in Clinical Assessment and/or training mode. A FindIT type game is a game in which a user is requested to find something, such as a game in which the user is asked to find a face of an individual in an image. In the FindITtype game, the user may be given a list of items to find in an image or image set—the image list may include relatively easy to find image parts (that is salient image parts that have a relatively high saliency score) and parts of the image that are relatively hard to find and that therefore have a relatively low saliency score, size, and/or where there may be competing content (flower with brown center versus flower with yellow center); or, for example in a "reaction time" evaluation to match as many image parts within a specified time. In a reaction time evaluation, the user is given a task to accomplish and the user is timed and scored based on the time taken to complete the task. Reaction time evaluations can include: find the red-roofed house in a landscape image or find the red-roofed house from within a group of non-red roofed houses where the user is timed on how long it takes the user to find, and optionally click on, one or more red-roofed houses) or click on all brown-centered flowers (and the user is timed on how long it takes the user to find, and optionally click on, all brown-centered flowers). As an aside, a reaction time evaluation may also be used as a positive or negative Turing test, depending on conditions.

In step 840, the user is assigned to a protocol, which may be a protocol for providing therapy or evaluating a patient. Step 840 may occur in combination with step 830 or separately. In some embodiments, the user is part of a research protocol, in which case the skill level is not needed. The user may be assigned a protocol by a healthcare worker In step 850, the user completes the interactivities that are provided based on the user's skill level or a protocol in which the user is participating (e.g., a healthcare worker or research protocol or study). In each of the interactivities one or more image sections or image segments can be used. The sizes can be varied to change the complexity level of the task and corresponding to skill levels.

The interactivities may include one or more of any of the interactivities contained in the platform. Some examples of interactivities that may be included in the platform include: Missing Pieces, Extrapolation, MatchMe!, MatchIT!, Mutation, Compose, Construct, Object ID, Dimensional Descriptors, Parts of the Whole. All interactivities are weighted according to each cognitive domain, ensuring that a battery of selected interactivities reflects and simultaneously engages multiple cognitive domains.

In one embodiment using single images in the Missing Pieces interactivity, an image part may be vertically oriented and/or horizontally-oriented spanning across multiple grid units and/or fill a single grid unit. The size of the image parts can represent between 1.5% to 50% of an image, for example. In one embodiment using composites in the Missing Pieces interactivity, an image part may be vertically oriented and/or horizontally-oriented and can span across multiple image sections. The size of the image parts can represent between 1.5% to 50% of each image.

In general, the user can move an image part to the reference image and then over to the grid, with additional back and forth movements between the image part being over the grid and the image part's original position (or another position) to effect a process toward arriving at a correct placement through estimation and/or approximation of the location of the image part on the grid, as well as, for the other interactivities to check their decisions and/or problem-solving skills with a given game piece against a reference image or other interactive resource.

Extrapolation is a variation on Missing Pieces, but instead of using a single image, uses a composite image set. The user is tasked with extrapolating the position of the image part from the composite and placing it in its proper location on a grid. The grid can vary in size, the number of pieces to be placed, the number of images and whether the composite is a stable or multi-stable type.

MatchMe! is an interactivity in which the user matches isolated sections of an image with portions of a reference image; MatchIT! uses composites and applies the same strategy of matching whole sections and partial sections, including spans. Spans refer to playing pieces which span across multiple images sections in a composite. Mutation is an interactivity in which parts of an image are altered and the user is tasked with identifying the altered portions, such as by correcting or removing the alteration. Compose is an interactivity in which the user assembles isolated parts of an image into a complete image; whereas Construct tasks the user with constructing a composite image from the isolated sections.

The Jumble-Sort interactivity, the system presents the user with a mixed grouping of one or more images that can include both vertically and horizontally sectioned pieces which can be the same width (all 25%, 20%, 10% for example) or mixed. The user is tasked to separate not only the images, but to separate these according to their sectioning strategy. In Speed Sort, the sorting process, accuracy and number of pieces sorted is measured against a fixed time; for example, 15, 20, 30 or 60 seconds, depending on testing conditions and the user's status.

In one embodiment, the user may work with a reference image which represents the original image in its entirety and/or the reference image may be a part of a larger reference image, which is extracted and which may become the new reference image. Corresponding image parts to be placed by the user are presented to the user for placement on a grid. In one embodiment, a portion of the reference image is masked and/or removed as a visual reference, and the user is tasked with placing image parts from this masked section on a grid. This same type of image manipulation where a part of the reference image is masked can be applied to other interactivities such as Missing Pieces, MatchMe!, Compose and/or Construct requiring that the user rely on their memory and attention to detail to complete the interactivity with speed and/or accuracy.

Interactivities can be used with a Reference Image which can be presented to the user as a preview—requiring that the user remember what they have seen, on-demand/hint, or continuously. Memory and attention demands differ for each and are weighted accordingly. All hands-on interactivities using composites are differentially weighted based on whether the composite combination includes 2 or 3 images and whether the image set is stable or multi-stable. In addition, the use of a composite Reference Image musters a virtual, View-Only interaction as users refer to the Reference Image and the mind subconsciously identifies parts of the whole and tries to resolve the ambiguous nature of the configured image set and where the cognitive demands differ between multi-stable and stable image sets.

The interactivities may include one or more of any of the interactivities provided herein and configured as a battery of individual multi-domain interactivities, which may be Mem+ analyzed for processing speed type, reaction time assessments (time limited placements), accuracy, and figure ground (f-g) dimensional and The Word List Recall (which may be referred to as Memory Recall) may be a memory recall of 3, 5 or 7 words. For example, at an initial predetermined time (e.g., T=0'), the user may be given a set of words and optionally immediately asked to recall the words. Later, after an intervening distraction activity, at a second predetermined time (e.g., at T=5'), the user may be asked to recall the words of the same word list (the second recall may be referred to as a Delayed Recall). Optionally, the WL Recall may also request more recalls of the word list at an additional predetermined time. In an embodiment all of the predetermined times are spaced apart by approximately the same time interval, during which the user is distracted with other interactivities. For example, there may be another Word List Recall at T-15', an Extended Recall. Alternatively there may be another word list recall at T=20'. In an embodiment, the time from initially receiving the Word List and the last Word List Recall may be between 10' and 20'. In other embodiments other durations of time may be used and/or chosen (e.g., automatically) based on the user's cognitive abilities and/or cognitive issues, as can the number and nature of the word lists, including image-cued word lists with a varying number of image-cued words.

In one embodiment of the compose interactivity, the user is presented with a sectioned image and/or images and is tasked to construct a matching pattern using a reference image which can be presented for a specified period of time and/or can be made available throughout the interactivity session and/or previewed for the user prior to the start of the interactivity, and/or is available to the user on demand. If the interactivity involves constructing a composite of two or more images, which is referred to as the Construct interactivity, then the user is also required to sort through the image sections in being able to find the appropriate sections matching to each of the component images. The user's placement pattern and order of placement (end pieces, one entire image first, then the second) provides insight into process. Behavioral patterns associated with age can also play a role in user gameplay, patterns and process analysis with regard to risk tasking users, choosing rapid placements at the expense of errors versus risk averse users, who might choose slower placements to make fewer mistakes- and variations in between. The user can also be directed to place parts belonging to only one of the images, an attention task to ignore the flanking and/or distracting pieces. User behavior and performance on tasks can be impacted by frustration, anxiety and stress. User cognition can be evaluated under stress conditions by changing the assessment conditions, the mix of interactivities, the number of speed rounds, for example.

Images can be sectioned in a pre-determined manner with the corresponding number and size of image parts/sections provided. Throughout this specification, the phrase "tasked with" refers to the user being presented with one or more interactivity screens having the tools for performing the task in question and being presented with indications of what task to perform, including practice opportunities. In one embodiment, the user may be tasked to place a special image section which is presented separate from another image section and/or sections and highlighted for the user. The user is tasked to place the "special" image parts into the correct locations within a defined time-period. Depending on the configuration whether the configuration is for assessment, training, and/or treatment purposes, the user may be penalized or not penalized on the task, and a type of reward assigned or not assigned for the correct placement of the image part. The task can be used for accuracy, reaction time, speed evaluations, and to assess user responses to changes in piece size, color, shape, sectioning strategy for advancement assessment and threshold fine-tuning.

In one embodiment of the Construct interactivity (composites), the platform can use a single sectioning strategy for each of the images or a mixed multiple sectioning strategy for each individual image in a composite and within an individual image.

In one embodiment, the user is presented with whole sections or with parts of each section (smaller interactive elements) for the interactivities. The use of smaller interactive elements and/or different sectioning strategies can be used to vary the complexity of the interactivity and the attention to detail required, as well as the image content and color characteristics.

Interactivities involving composite image sets may use a 2- or 3-images with any number of sections between 4-100 and/or image parts representing 0.1% or less of an image, depending on the intended interactive tasks, level of complexity and purpose of the interactivity.

In one embodiment of the Mutation interactivity, the user is tasked to identify introduced changes to the image set and/or individual images that result in an error of some type in the image or image sets composition. Examples of mutations, include, but are not limited to: the duplication of elements that are not duplicated in the original image, the insertion of an unrelated image part, the deletion of an element of the image, the inversion of an element of an image, rearrangements of elements in an image, and/or transpositions of two or more elements of an image with each other, among others. In one embodiment, the transposition-type mutation involves a composite where a section or a segment and/or segments/sections belonging to Image #1 is reciprocally transposed or non-reciprocally inserted into Image #2 or Image #3. In one embodiment, the inversion type mutation is where an image section or segment can be vertically flipped Smaller segments can be involved, increasing the challenge level in looking for what is different from the template or what is not correct in a presented construct. An image and/or image set may contain more than one mutation and can include more than one type of mutation, and can be provided with a count on the number of mutations present, and a countdown as these are found. The user may be presented with a series of progressively more challenging Mutation interactivities and/or the Mutation interactivity can be combined with another interactivity as part of a therapeutic and/or training protocol.

In one embodiment of a MatchMe! interactivity, the user is tasked to identify one or more matching sections and/or segments of a collection of images to a reference image which provides the user with an active template that can be copied. Segments in single images can range in size, in both the horizontal and vertical orientation between 1.5%-50% of the total image and/or can consist of a mixed variety of section percentages. In one embodiment, the reference image template is intact and the user looks for a matched section. In one embodiment, the reference image template is missing sections leaving holes in the reference image template, similar to an incomplete puzzle where the pieces are to be placed. The pieces can be the same size or of different sizes as one another. In one embodiment, using 2- and/or 3-image composites, the MatchIT! interactivity involves a missing segment and the piece that is to be inserted to that position. The missing or to be matched segment can be a span of multiple sections from more than one of the component images. In other words, the missing section or to be matched section that needs to be matched and filled may include two or more adjacent image sections in a composite image.

The platform can be used for multiple learning styles based on the interactivities' mix which is used and which allow users to demonstrate their skills in one or more areas, but which can also highlight differences in user ability without penalty for a matched learning style interactivity but which is adjusted based on user's capacity and capabilities.

A unique feature of the platform is the integration of composite image sets with the inherent ability to interact with the user on a subliminal and/or subconscious level, an effect due in part to the illusion of depth which is generated by juxtaposing image sections in both stable and multistable image sets, and which is amplified with the dynamic shifting of images in the figure-ground positions which users can perceive with multi-stable image sets. As the user is interacting with the image sets, a switch in which image appears as background, i.e. in the ground position can occur. This process engages a second process for the image in the ground position as the gaps in the confluency of the ground image are largely ignored based on Gestalt principles and appears assembled. This can occur independently of the user's conscious awareness and/or tracking across alternative contiguity lines, and which may trigger a perceptual switch. The perceptual switch, while occurring subconsciously, can also be linked to active engagement of cognitive processes where the user is guided and/or made aware of the switch and/or alternate percepts, and is directed to focus on a particular areas of the image. This kind of a value-added engagement of cognitive processes can be factored into the cognitive benefits offered by the platform, and which can be evaluated with functional Magnetic Resonance Imaging (fMRI) and/or directed Electroencephalogram (EEG)/Event Related Potentials (ERP) signals and/or eye-tracking to provide users with an adjusted baseline. Functional MRI is a type of specialized MRI scan, which measures the hemodynamic response related to neural activity in the brain or spinal cord of humans or other animals. Higher amounts of blood flow are seen as indicating activity areas of the brain that have higher amounts of brain activity. Thus, fMRI measures areas of activity—the theory being that the user is lighting up areas of the brain involved in performing the interactivities. Monitoring the brain with fMRI or EEG/ERP spikes associated with the user's interaction would occur in a clinical setting. The fMRI or EEG/ERP can also be used to differentially evaluate multi-domain cognitive engagement especially in patients/users who have suffered traumatic brain injury, concussion or following stroke where other areas of the brain may compensate for loss of function in one area. A regular user might use a commercially available EEG headset (like Muse) which is configured for the platform, or use an eye-tracking system which can be used today with an App or Google glasses to track user eye movements across and around image/image sets. However, a home user could also be given access to these types of clinical measurements.

By supporting and/or improving awareness and thinking skills among users with cognitive impairments and/or other changes in cognitive status, and/or in building cognitive reserve through attention focusing, memory triggering and language-building interactivities, the platform has the capacity to impact ADL (Activities of Daily Living), a practical value and measure of the transfer of gaming skills and learned skills to providing practical improvements to the lives of platform users.

In step 860, the data based on the interactivity (e.g., performance data) is stored in association with the information about the performance of steps 810, 820, 830, and 840.

In step 870, the user's profile may be updated based on the results of the interactivity. Step 870 may include a change in information about the user's diagnosis, cognitive health, physical health, skill level, and/or which protocol the user should be assigned.

In step 880, a progress metric is displayed for the user, giving the user the results of the interactivity in combination with information about the user's skill level, progress, diagnosis, and other profile and/or signature features. The progress metric may be displayed only to the user and the user's clinician or researcher. Alternatively, the information may only be provided to a health care worker who may then decide how to communicate the information to the user. After the progress metric is displayed, the session ends in step 890.

In an embodiment, each of the steps of method 800 is a distinct step. In another embodiment, although depicted as distinct steps in FIG. 8, step 810-890 may not be distinct steps. In other embodiments, method 800 may not have all of the above steps and/or may have other steps in addition to or instead of those listed above. The steps of method 800 may be performed in another order. Subsets of the steps listed above as part of method 800 may be used to form their own method.

In some embodiments, the invention uses images and image sets as the basis for hands-on and/or hands-free and/or view-only challenges and interactivities; though other parts of the invention can be configured with non-visual content for a subset of puzzle-styled interactives (interactivities that are in the form of a puzzle) and/or be combined with non-puzzle-type interactivities. Visual inputs can be conveyed through a variety of means including, but not limited to, sighting, implants, signal transducing wearables and other devices, and/or brain-computer interfaces. For visual inputs, the interactivities can be applied to individual images, to composite image set constructs made up of two or more images, and/or to the individual images (component images) comprising the composited constructs.

In one embodiment, the platform may utilize content-rich, real-world images. Images can be color, halftone, black/white (b/w), and/or degraded images/photographs, and/or other types of source images. Some examples of types of source images are as video-captured still images, artwork, illustration, drawing and/or paintings in various combinations. In one embodiment, individual images can depict single objects as line drawings, illustrations and/or photographic images, and/or other type of representations with and without applied graphical filters and masks. Some examples of representations that may be used by the platform may include a degraded image or an image with partially obscured image content. A degraded image or partially obscured image may be used for a subset of interactivities primarily related to one or more of the following: building object and pattern recognition, language skills and attention skills, and executive function among other learning and/or skill-based objectives.

Images with content-rich elements can depict a scene with people, animals and/or inanimate objects in various combinations and/or be set in an urban or rural environment, in a multiplicity of combinations. The term "images" can include static images, a combination of images, a sequence of images, or moving images. Some examples of moving images that may be included in the term "images" are video or film scenes and clips, as well as static screenshot-type images captured from video or film sources. Images can be sourced from pre-screened libraries of selected images and/or be supplied by the user, according to image specifications and security requirements, and the images may be tagged according to the platform's requirements with image characteristics (color, content, and contiguities) analyzed as described previously.

Composite images can be generated by serially sectioning and juxtaposing the image sections from two or more images to portray the illusion of depth. The illusion of depth may be a visual illusion effect that is rooted in the figure and ground relationships. The illusion can portray a second characteristic if one or more of the component images contain specific image attributes referred to as contiguities.

Content, color, and context may aid in defining a contiguity or the interpretation of a contiguity. As such, in an embodiment contiguities in an image can provide visual cues which the user can use to track across an image when two or more images are combined in a specified fashion and where at least one image contains a contiguity or when two or more images contain contiguities in a composite of two images or in a composite of three images. A contiguity does not need to span across the entire width of an image and a specific contiguity's characteristics can change across the width of an image from being pronounced to less defined, and vice a versa. The visual effect of the composite and the impact of the composite on the user differs, depending on each image's contiguity characteristics with a set of variables, including: color, content, context and the image's overall complexity, and which can be used to personalize image sets, and by default, the user's interactive gameboards/interactive surface and experience. Users with higher degrees of cognitive abilities may be able to piece together an image in their mind with fewer visual cues, such as contiguities and/or contiguities that are less noticeable, as indicated by the numerical values associated with the contiguity's characteristics. As a result, interactivities may be chosen based on the characteristics of the image and the contiguities in the images to test for higher and lower degrees of cognitive ability.

Images can be contained in an image library (PICSSL) and can be tagged with attributes. Attributes can include text and/or audio labels of image content and elements, a category label, and assessment attributes, for use with Word List Recall using the image's embedded visual cues, and associated SQ2 (Spatial, Quantitative and Qualitative) questions, Object ID and Dimensional Descriptors. Each image may be analyzed based on its contiguity characteristics to derive aesthetic and ambiguity values which are used to define the complexity of the image and its potential complexity contributions in a composited image set.

The image library may be restricted to include a subset of images which may be presented to select user groups, depending on skills and learning requirements. For example, in an embodiment, the use of nature-themed images in the platform leverages prevailing knowledge about interactions with nature and the effect of the interactions with nature to improve well-being based on Attention Restoration Theory and Stress Reduction Theory. The system can be configured to deliver defined images based on their content and/or a subset of image content to meet therapeutic and/or training requirements, such as to train or test the end-user's memory and/or attention. The images and/or subset of images may be chosen needs of place and time. In one embodiment, the platform may be configured to use images with people's faces or with portions of people's faces, such as a profile. The images with people's faces or with portions of people's faces may be included to support facial recognition and/or other biometrics-styled interactivities for training users with deficiencies in related to being able to recognize faces as can occur in people following stroke and with Autism Spectrum Disorder.

The library may include a searchable index and categorical groupings to facilitate use of images and/or searching for/selecting images. Contiguity characteristics and/or relationships of contiguities to establishing figure-ground relationships in and between images not only provide visual landmarks, which can be used as search parameters, contiguity characteristics and/or relationships of contiguities to establishing figure-ground relationships can also be used for general image analysis purposes in computer vision applications, and which apply principles of visual perception and attention.

In some embodiments, the platform may be utilized to deliver a subset of interactivities for entertainment purposes and/or as part of a marketing and promotions strategy using visual content to support customer engagement, acquisition, and retention. Content may be user-supplied and/or content supplied by a third party, which may be used to provide users with incentives, rewards, discounts and other promotions related to the content and or the promotional objective. The incentives may include travel and tourism, entertainment venues and film, and/or other entities with promotion objectives which can utilize an interactive and/or engagement tool to engage current and prospective customers and/or users.

In some embodiments, the platform may be used to effect a team-building and/or to effect a change in management strategy within a corporation, a user's health, and/or a business. The platform may be used to effect a change in an activity and/or to effect compliance with a rule, such as a change in maintaining a drug and/or treatment protocol and/or adoption of a new software solution in support of a deployment. The use of the platform in these types of situations can be viewed as a combination of entertainment and learning facilitation, according to the platform's cognitive engagement capacity.

FIGS. 9-12 provide embodiments of methods of using the interactive cognitive platform by a user.

Figure 9:
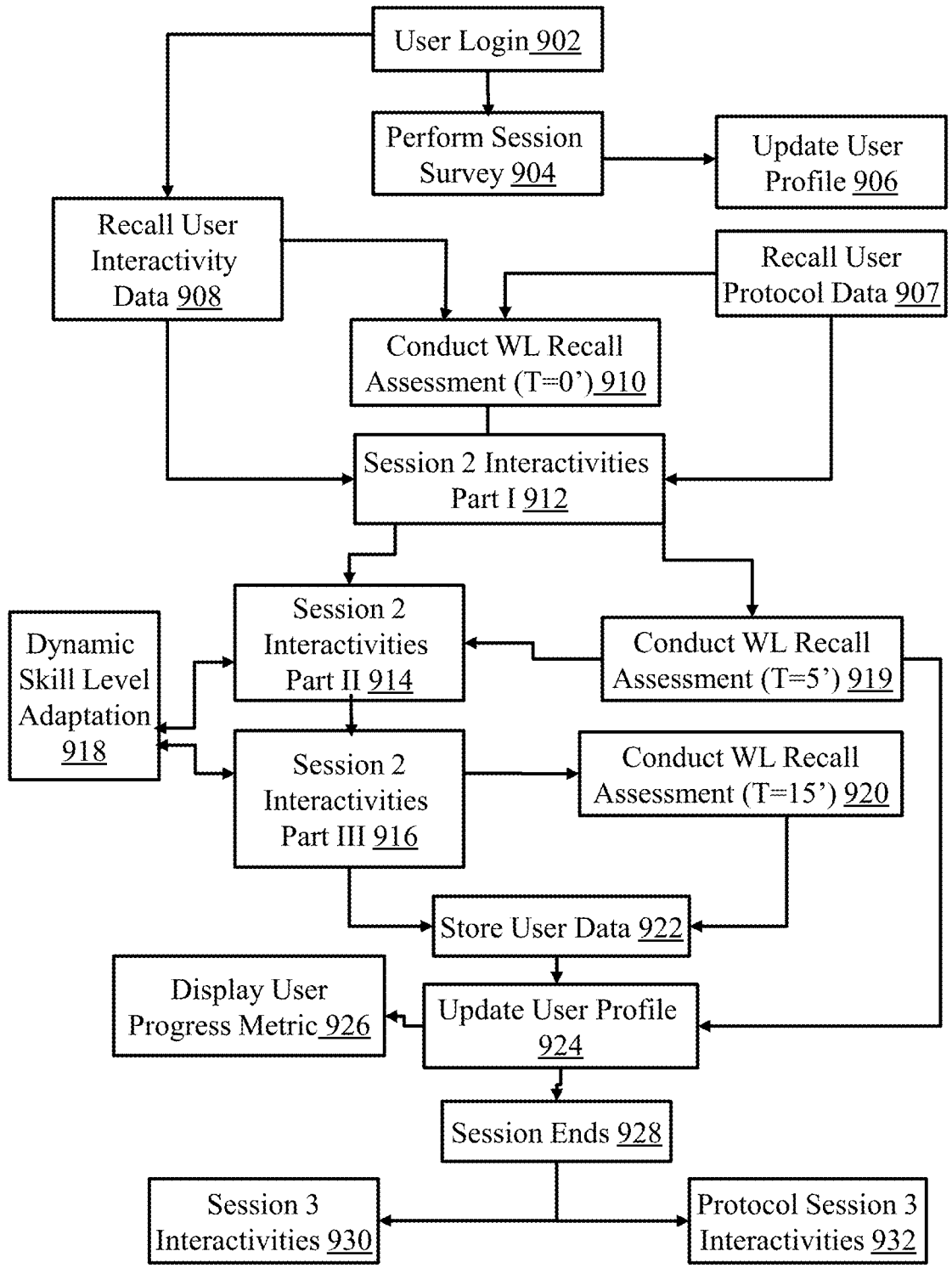
FIG. 9 shows an example of a flowchart of a method of using a multi-purpose interactive cognitive platform for a returning user (a multi-session protocol).

FIG. 9 provides a multi-session protocol for a returning user. Both professional users (e.g., health care workers) and end-users (e.g., patients) may access the platform's multiple interactive modes, including: FreePlay, Challenge and Mem+ mode. The Freeplay mode allows the user to choose what game the user would like to play and to play any given game for as long or as short of a time period as desired with user defined selections for skill level and images. The challenge mode includes interactivities that challenge the skill level of the user with preset progressions. The Mem+ modes includes interactivities that involve the use of memory. Based on instructions given to the user by the professional, and/or as the user directs themselves, a subset of interactivities may be performed for a specified period of time according to a prescribed frequency and/or as directed by the system with recommendations on frequency and skill level, and/or as part of an intervention or maintenance regimen to support cognition. The user can manually engage the assessment mode for a specific interactivity or set of interactivities, and add those measures to their user profile.

FIG. 9 shows a multi-session protocol for a returning user 900. In step 902, a returning user is provided with a login interface, via which the user may login (see also 810 in FIG. 8 for login information that may be required).

In step 904, the user performs a session survey. A session survey is presented to the user. The session survey may include questions asking the user whether the user found the previous interactivities and/or the cognitive protocol useful. Questions may be presented to the use, via the platform, to identify specific information that allows the cognitive platform to be better personalized to the user. There may be other questions that request other information to identify whether the protocol is helping the user (e.g., via diagnosis or treatment of a disorder). Alternatively or additionally, the survey may ask whether the protocol has been entertaining and/or engaging to the user to further support compliance. For example, questions may include, but are not limited to, how long the user sleeps, sleep patterns, diet, dietary habits, current medications, medication changes, stress levels, etc. These are variables that can impact user data and may explain why scores are significantly different from a baseline score, that the changes are not progressive or permanent, but conditional. There may be questions asking for information about the user's health, dietary, and sleep patterns and other things that may affect the user's performance for a given session and may erroneously imply changes in cognitive status but which are situational. However, in an embodiment situational changes would be tracked to facilitate identification of actual changes in cognitive status which are associated with long-term changes in sleep, diet, exercise for the user and which may be applied to other users in developing predictive analytics. In some embodiments, the survey can include questions enquiring whether the clinician found the interactivity useful.

In some embodiments, the session survey identifies what type of learner a user is in combination with previous progress metrics. For example, an interactivity where a user is unable to perform a certain task with accuracy or within a predetermined time threshold, may be used as an indication of the user's cognitive status. The user's cognitive status may be further assessed using alternative protocols within the platform optionally together with third party assessments of the user. For example, visual-spatial tasking can be highly developed in some users that are deficient in other areas as a matter of history (despite, for example, a statistical correlation between those other areas in which the user is deficient and visual tasking, indicating that it is unusual for someone with this user's deficiencies to be highly developed in visual-spatial skills), and the high visual spatial skills is in the case of this user is therefore not an indication of changes in cognitive status over time or due to a condition (even though a temporary further exacerbation of their inabilities may occur. As another example, a user who has historically been an auditory learner and not a visual learner would find certain tasks challenging as a matter of course, and even though most people that perform poorly on certain auditory test also typically perform poorly on certain visual tests, the poor performance of this user on those visual test and the good performance of this user on those auditory tests is not a result of a change in their current condition or cognitive status. The converse may also be true in that a strong visual-spatial learner may have auditory learning deficiencies. Similarly there may be users having an array of mixed types learning styles along a continuous spectrum.

By leveraging a knowledge of the user's learning style, an assessment of changes in cognitive status is informed by the user's general abilities as a factor in choosing and evaluating the value and validity of certain types of assessment indices. The variability in learning styles is viewed as a factor in personalizing gameboards and interactivities to better meet user needs, rather than as a deficiency to be remedied and/or negatively contributing to a user's evaluation. The dynamic aspect of the platform allows for the integration of multiple learning styles in order to foster cognitive gains whether for remediation, training and/or skills development. The platform does, however, place a premium on visual input, hand-eye coordination and reasoning—critical tasks needed for everyday living. As such, the platform may not be suitable and/or effective for people who have little or no interest in puzzle-type interactivities.

In step 906, the user's profile is updated based on the information received via the survey.

In step 907, the user's previous protocol data is recalled. This may occur to enable the protocol to choose a skill level, to identify which protocol and interactivities the user should do next (perhaps based on a clinical protocol the user is involved in), or based on the user's preferences.

In step 908, the user's interactivity data is recalled. Optionally, the survey may be skipped and the user may be immediately presented with the interactivities. Along with recalling the user's interactivities data and presenting the interactivities pages to the user, the interactivities may be personalized and a new interactivities page (with new interactivities) may be presented to the user based on the user's previous personalized interactivity.

In step 910, the system conducts a Word Language (WL) Recall assessment at time 0. In the pre-session survey, the user is also tasked with a word list recall assessment administered at T=0'. A significant part of the assessment protocol is that the assessment protocol may be built into the platform—the assessment may be an embedded assessment that is embedded in the interactivity process, which may be implemented as the user engages in the interactivities, as described below. The Word Lists are derived in part from objects and elements contained in the images and/or image sets which are used as the basis of the interactivities. As such, the words in the Word List which the user is tasked to remember over time are image-cued and embedded in the interactivities. During the interactivities, the user is physically manipulating, or in the case of a view-only option, the user is mentally manipulating, the image parts, and interacting with a subset of the objects and elements in their Word List (WL) both on a conscious and subconscious level. The Object ID Memory (OIDm) assessment has similarities to Word List Recall assessment in that the words are image-based and image cued, only with IODm the user derives the word list from an image. With OIDm, they are given 15 seconds to come up with 5-7 descriptive words about the image. After 3-5 minutes of other interactivities, they are tasked with remembering as many words as they previously listed.

Back to Word List Recall, each image may be tagged with descriptors which identify objects and elements contained in each image and from which images or parts of images are associated with a list of words, creating an image-associated Word List that may be derived for the user and/or with one or more user sessions. A Word List Recall assessment may contains three (3) or more words. The number of words to be recalled is also metered to the user skill level and cognitive status. For example, Image #1 can contain representations of a bird, a branch, sunrise, day, a silhouette, a hawk, no leaves, a tree, and golden. The words associated with an image can be represented in the image as visual elements or derived from the image inferred such as the "day" tag. The number of words used in the assessment is based on and/or derived from an image and/or image set is approximately forty (40) percent; such that for a 3-Word WL, at least one word is based on, and/or derived from the image and/or image sets. Similarly, in a 5-Word WL, at least 3 image-cued words would be integrated into the assessment. Optionally, the words derived from the image may be derived automatically, based on an automated image recognition program, which may make use of contiguities, for example to identify parts of the image.

In an embodiment of the Word List Recall assessment, the user is tasked to recall the word list (WL) at multiple time points. The first time point is T=0'. Similar to traditional Recall assessments, the user, after hearing and/or reading the list of words aloud, is tasked to repeat the words back into optionally a microphone of system 100, twice, for example A Delayed Recall assessment is deployed at or about T=5'. During the intervening time, between T=0' and T=5' (other time periods of other lengths of time may be used instead), the user is tasked with performing a set of interactivities using the images with tagged words related to and/or conveyed by the image or image sets, depending on the interactives the user has been tasked with in a session. Traditional cognitive assessments which integrate a Word List Recall and Delayed Recall protocol generally use only T=0' and T=5' time points results to calculate a cognitive metric. The cueing used allows the recall assessments to use visual cues of tangible real-world objects readily available in the user's immediate environment with words such as chair, desk, table, window—familiar and within the user's visual field, which can test the associations the user makes between words and images. The platform uses visual cues as well but the visual cues are embedded in the image sets with which the user is tasked to interact with, generating a "do" operation, enabling an enhanced potential for user learning, memory retrieval, attention focusing, and skills development through the interactivities and their use and/or manipulations of the image and/or image sets as well as the reference image to support a user's solving stratagem.

The platform provides the user with directed interactions with the associated cues with the goal of fostering a stronger connection and memory recovery and memory building opportunities through an active learning approach and potential associative scaffolding.

In one embodiment, the platform uses an extended time point for conducting a recall assessment which is timed to occur at T=+10' from the start of the user's interactions with the image-based interactivities and/or within that time frame up to approximately T=15' in one embodiment and/or to the completion of an active interactivity. In one embodiment, parts of the recall assessment can extend to longer time-periods within a given session, or may extend beyond a given session to another designated time point within a treatment protocol or beyond the treatment protocol depending on the requirements of the treatment and/or training requirements. The number of correct and incorrect absolute responses, such as the recall of the precise word and/or words is assigned a score. As the recall assessment assigns points, users may receive partial points for errors in word list recall assessments, if the words the users recall are categorical, i.e., the word, "table" might be called furniture by the user or might be called, desk or dining room table with an elaboration on the to-be-recalled word or words.

In one embodiment, users can be tasked to place object labels on associated objects. Placing object labels on associated objects can be used to reinforce learning for those with cognitive and/or language impairments. Text labels may be configured as part of a multi-language pack to make the platform user-friendly to non-native English speakers and/or to people who have developed linguistic challenges associated with cognitive changes. In one embodiment an auto-sequence may run where the system places object labels on image objects to support recovery and learning for users with limited fine and/or motor control. The interaction in this case is View-Only but offers mock-ups of the interactivities for viewing in addition to viewing engagement of the image sets themselves.

A Tangible User Interface (TUI) device and/or prop can also be programmed to present a word label. The user would then place the device with a label proximal to the object as part of the interactivity and/or assessment. In one embodiment, the labels can be on-demand activated or automatically displayed by the system in order to assist a subset of users with specific cognitive issues, including linguistic challenges and where tagging of image elements can help support cognitive health.

In step 912, Session 2 begins with interactivity part I. In step 914, Session 2 proceeds to interactivity part II. In step 916, Session 2 proceeds with interactivity part III.

In step 918, a dynamic skill level adaptation assessment is performed based on Session 2, in particular based on the interactivities part II and III.

Parts I, II and III is a shorthand used to describe interactivity sets, where parts I, II and III would be interactivities set 1, interactivities set 2 and interactivities set 3. Each set may be comprised of a collection of interactivities using the same image sets throughout. Since there is a 5 minute time gap between WL Recall T=0' and T=5' and similarly between T=5' to T=15', the time can be filled with interactivities. For example, a healthy young person might complete a standard interactivities set 1 in a minute, making the time interval required for performing a WL Recall (immediately then delayed) in need of filler interactivities to have a delta of 5' to get to T=0' and T=5' recall time points. Optionally, the user may automatically be given other interactivities to fill the remaining time. In other embodiments, a time interval that is different than 5 minutes, and where the different time intervals may have different durations.

In step 919 alternatively a word list (WL) Recall assessment is performed at time=5 minutes after Session 2 interactivities Part I (step 912).

In step 920, a WL Recall assessment is performed at time=15 minutes after Session 2 interactivities Part III (step 916). In addition to a T=+5', T=+10' and/or a T=+15' recall as part of the extended Word List Recall, a modified Word List Recall assessment can use compiled word lists from multiple sessions and associated images, and where the user is assessed at another session and/or at the midpoint and/or conclusion of a therapeutic protocol.

The Word List Recall assessment, together with other assessments, can be conducted in sessions in the presence of a health care worker, in a digital, remote or physical mode. Assessments can also be conducted in a self-directed manner by the user themselves using audio recordings and analysis of the user's responses for Word List Recall assessments, and/or for SQ2 questions which can be a verbally transmitted and/or using a device including direct input into a device with transmission of user data, and/or through a secondary device, such as a scanner where the user's inputs are recorded on paper and then scanned for analysis by the platform and/or health care worker.

Similarly, for a facilitated assessment the user is tasked to recall the Word List at specified times and to verbally state and/or manually record their responses. The latter can be accomplished with a compiled list of words from the word list as well as non-word list words. The user is then tasked to identify from the mixture of words, only those words contained in the word list. The audio recording of the user's verbal responses can be used as a biometric tool to indicate changes over time in various vocal and/or voice related metrics.

In step 922, the user data is stored. Storing the data occurs in either alternative, after steps 920, 919, and/or 916. The data can be used in future sessions to identify an appropriate skill level and/or personalized interactivity for the user.

In step 924, the user's profile is updated with the information provided in step 922.

In step 926, the user's progress metric is displayed.

In step 928, the session ends, although if the user and/or clinician desires, a third session can be started in step 930 or 932 with Session 3 interactivities within the same sitting.

In an embodiment, each of the steps of method 900 is a distinct step. In another embodiment, although depicted as distinct steps in FIG. 9, step 902-932 may not be distinct steps. In other embodiments, method 900 may not have all of the above steps and/or may have other steps in addition to or instead of those listed above. The steps of method 900 may be performed in another order. Subsets of the steps listed above as part of method 900 may be used to form their own method.

Figure 10:
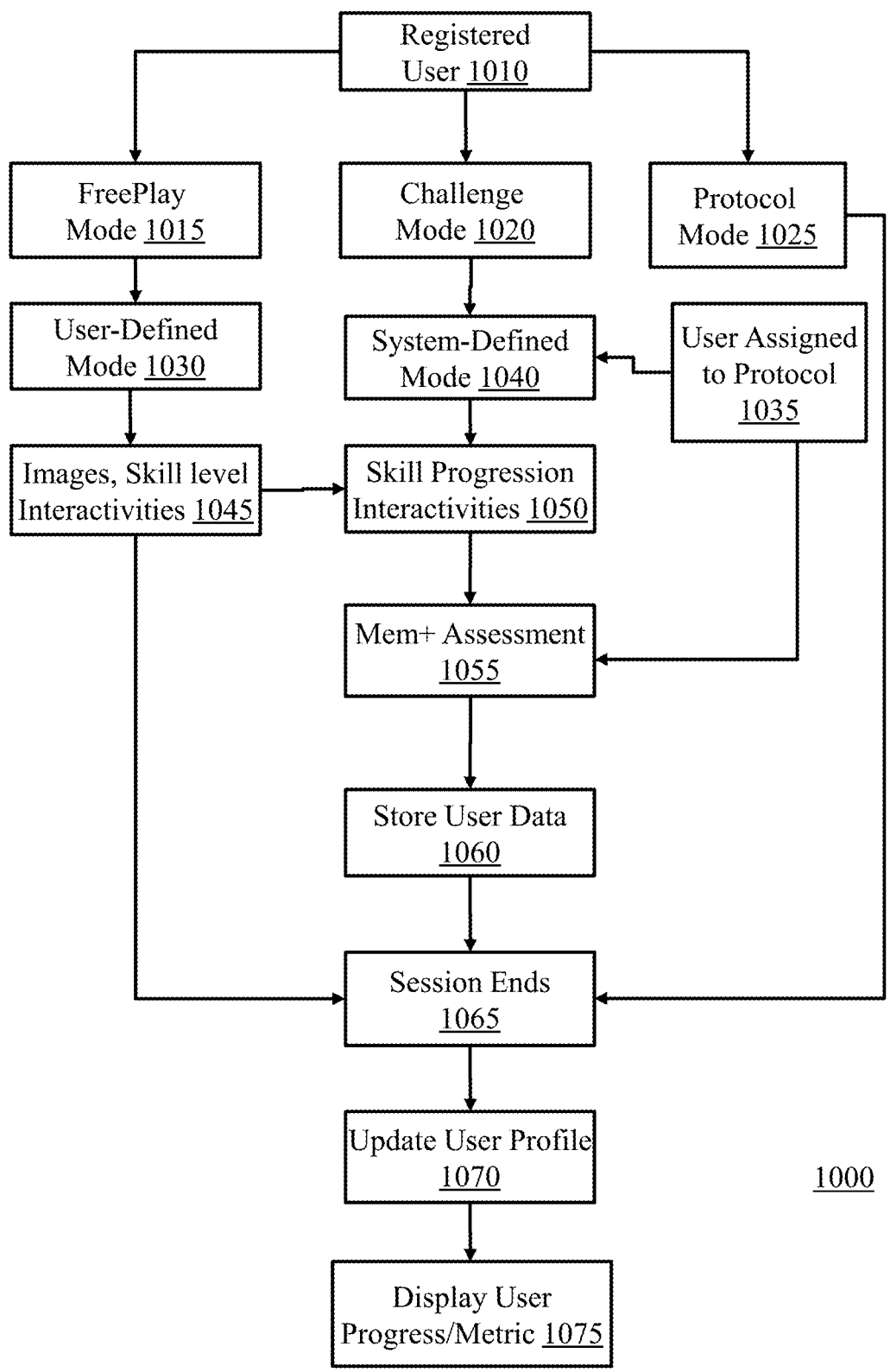
FIG. 10 is an example of a flowchart showing three options for how a registered user may interact with an interactive cognitive platform.

FIG. 10 is an example of a flowchart showing three options for how a registered user may interact with an interactive cognitive platform resulting in the display of a user progress metric 1000. The user may choose FreePlay Mode, Challenge Mode, Protocol Mode, and User-defined mode. In addition to choosing the mode, the method provides many steps that allow the user to personalize the GUI, the game, the interactivity, and/or to include the Mem+ protocol. The personalization process may include interactivity sequence and skill level progressions as well as customization of the User Interface to allow the user to adjust and manipulate the left-right, top-bottom configuration of interface elements. The personalization process may include spatial manipulations of the reference image, template/grids, work area containing interactive elements, resizing of elements, zoom capabilities, image library hide, timer toggle, among other platform features.

The platform presents the user and health care worker with a Mem+ mode, which can deliver multiple therapeutic and training interventions based on the user's requirements and dynamic cognitive status. The Mem+ mode can also be implemented by a health care worker to address user-specific issues as part of a chronic and/or transient condition to help support brain health and as an assessment for baselining a user's cognitive status to track changes over time, the introduction of new medications, drug safety during drug development, cognitive norms following anesthesia administration, and/or to evaluate the effectiveness of an intervention. Mem+ mode delivers a series of interactivities in a directed fashion, and/or as part of a progression. The Mem+ mode may be divided between Easy, Medium, and Hard levels which may be entered at any of the sessions automatically and/or according to a health care worker's directions (in other embodiments there may be fewer or more gradations of the level of difficulty of a test or battery of tests).

In one embodiment, each level has a minimum of number of sessions (e.g., 12 sessions per level) and may use the same image set for a predetermined number of sessions (e.g., for groupings of 2 sessions) over a predetermined time-period (e.g., on a weekly basis), as an example Within each skill level, the interactivities may range from easy to difficult along a continuum or vary only with the image sets presented to the user which are used in grouped sessions (for example the grouped sessions may be weekly sessions—sessions grouped by the week). In general, the therapeutic protocol can use switch-capable image sets (multi-stable), non-switchable image sets (stable) and/or a mix of switchable and non-switchable image sets, as well as, the component images, according to the therapeutic or training protocol.

Mem+ can have multiple modes, including an Attention Focusing mode which may allow the user to develop and/or advance their skills using a subset of the interactivities of the Mem+ interactivities. In the attention focusing mode, the user is presented with a series of interactivities using image sets that utilize a variable sectioning strategy which can be portrayed as a progression of changes but where the collection of interactivities or the individual interactivity is still multi-domain in nature to greater and lesser degrees across the different domains. The platform may also deliver a subset of images, which may also contain distractor and/or attractor elements. The image content's objects may be represented as part of an image or may be represented as the image itself in its entirety. For example in the case of a flower, the flower may be viewed as either an attractor or distractor depending on the protocol and the second and/or third images in a composite, and the user may then be tasked with an appropriate measure of attention using Mem+ and SQ2 questions related to the flower image and/or one of the other images in the composite.

In step 1010, a user is registered (see also step 810 in FIG. 8). A summary of how the user may use the platform is described here. The user registers to use the resources or is registered by a facilitator (professional, therapist and/or caregiver). If the user is engaged with the platform in a self-directed manner, the user can access one or more of the following in a session: FreePlay, Challenge, or Protocols (in other embodiments there may be other options. Each new user is tasked with completing a baseline set of interactivities, given at one of the three skill levels, depending on their assessed estimated and/or projected abilities to obtain baseline measures. A re-evaluation may be conducted periodically and the initial data may also be compared to other point-in-time data for FreePlay and Challenge users across ages, gender, conditions or other parameters for comparative purposes. Users engaged in Protocols options are assessed within the protocol, relative to their baseline measures and to other normed data sets.

In step 1015, a user decides to use FreePlay Mode. In FreePlay mode, the user may resume a saved interactivity or begin a new one. The user is responsible for choosing the images, interactivities and skill level. The user progress may be measured according to best times to complete and which may be posted and compared to other users scores using the same scenario (images, skill-level and interactivities) in a modified type of competitive play against other users and also themselves to improve their personal scores.

Alternatively, in step 1020, the user may choose to proceed in Challenge Mode. In the Challenge mode, users are also provided with a set battery of interactivities, where completion of the tasks progresses the user through levels of increasing difficulty and/or complexity with respect to image content and number of tasks required to complete the level. Completion statistics are available for each user at each level and sub-level, and which can be made available to peers using the site based on user privacy settings. In addition to the professional collaborative space, a challenge space can be included in the platform which encourages use by users through game design and competitive play between users who have developed their own user-defined configurations and want to share their configuration. This social space can include stats, chats and potentially live tournaments similar to multi-player game site where time to completion is the metric of success. In addition, the cross-over opportunities can include testing of professional gameboards with volunteer end-users; and/or, the development and sharing of a wider range of interactive tools suited to different user groups with different health conditions through these types of collaborations.

Alternatively, in step 1025, the user may choose to proceed in Protocol Mode. In Protocol Mode, protocols may be developed by clinicians for users and/or suitable to groups of users across ages, gender, language and motor capabilities, and/or conditions. The users may be users that are not responding to standard therapies. Users may be individuals who have been selected by professionals to participate in one or more health care programs. In some embodiments, as part of the protocol mode 1025, if a user attempts to enter the protocol mode, and if it is determined that step 1025 proceeds to step 1065. In step 1065, the session ends, because the user is not assigned to a protocol mode yet or because the timing of the protocol does not allow a user to participate at this time. Protocol users may also be users in research and/or clinical studies. Protocol users may also be represented by general users who have an interest in the health care program, i.e., self-recruited into the program studies to beta test software and/or as participants in the studies directly. Protocol users may also access a separate development area for non-professionals (or professionals) as developers for developing new protocols for new therapies and/or test. The interactivities can also be made available to Professional Protocol Developers for use (and/or further subsequent study). In step 1030, the User may choose to proceed in User-Defined Mode. Interactive protocols developed by non-professionals or professional may be placed into a test bed area and which can be shared with other general users (optionally the protocols developed may be protocols for tested and proven treatments, but which may need to be tested for software bugs or optionally may be part of a research program). In some embodiments, as part of the protocol mode 1025, the session ends in step 1065 because the user is not assigned a protocol mode yet or because the timing of the protocol does not allow a user to participate at this time.

User-defined Mode may include any choices the user made previously to personalize one or more interactivities, the GUI, the images, etc.

In step 1035, alternatively to step 1030, a user is assigned to a protocol by a health care worker.

In step 1040, the user chose Challenge Mode (step 1020) or the User was assigned to a protocol (e.g., in step 1035) and the system automatically proceeds with a system-defined mode. System-defined mode may be based on protocols provided by health care workers or researchers for this user. Alternatively System-defined mode may take into account all of the previous information about the user and, via an algorithm, decide which mode would be best for the user. In some embodiments, after the user is assigned a protocol, a Mem+ assessment occurs (step 1055).

In step 1045, images, skill level and interactivities are chosen by a user via User-defined Mode.

In step 1050, skill progression interactivities are provided by the system based on either the images, skill level, etc. chosen by the user in step 1045 as part of the User-defined mode, or chosen by the user based on the system-defined mode implemented in step 1035.

In step 1055, a Mem+ assessment occurs by the system. Assessments are based on a set of interactivities which the user is tasked to complete. Time to completion of the task contributes to building the metric as can the following: how the task is completed, the number of correct or incorrect placements, repeat errors in mis-placements, reaction time, and rated according to the overall skill level and skill level adjustments during the interactive, stable or multi-stable image sets as well as the overall complexity rating of the multi-domain interactive or battery of multi-domain interactivities. The user's interactivity pattern is factored with multiple variables, including: time of day, sleep patterns, medication changes, stress/daily impacts, and other changes in health status which can be assessed through pre-session surveys.

In step 1060, the user data is stored and in step 1065, the session ends.

In step 1070, the user profile is updated after the session ends, and, if desired by the user or the healthcare worker, in step 1075, the user progress/metric is displayed.

In an embodiment, each of the steps of method 1000 is a distinct step. In another embodiment, although depicted as distinct steps in FIG. 10, step 1010-1075 may not be distinct steps. In other embodiments, method 1000 may not have all of the above steps and/or may have other steps in addition to or instead of those listed above. The steps of method 1000 may be performed in another order. Subsets of the steps listed above as part of method 1000 may be used to form their own method.

Figure 11:
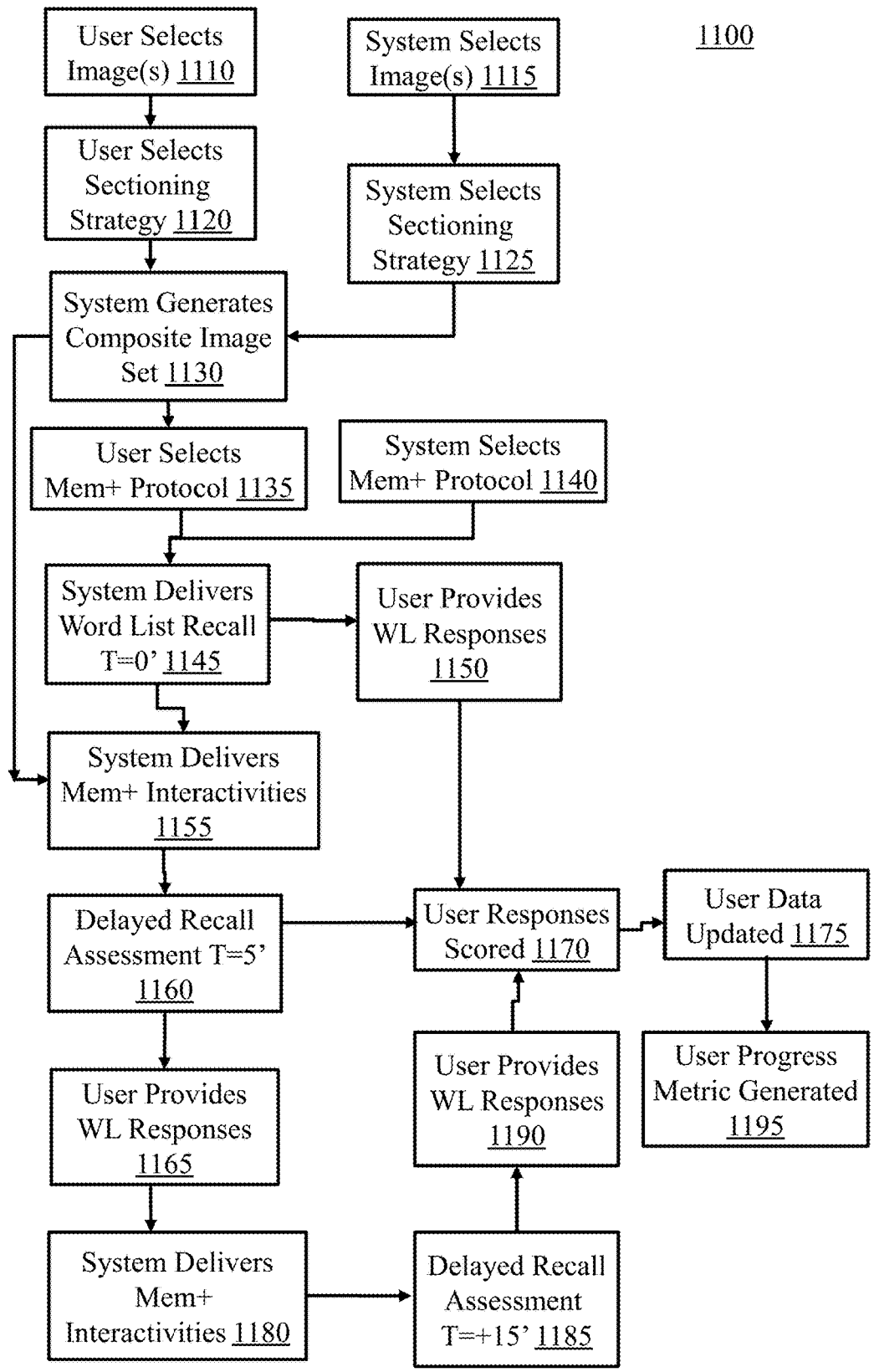
FIG. 11 is an example of protocol options for a user starting with the selection of one or more images from a graphical user interface.

FIG. 11 is an example of protocol options 1100 for a user starting with the selection of one or more image from a graphical user interface. Thus the option 1100 can be whether the user or the system selects the images that are then used for interactivities for the cognitive platform. See FIGS. 21-25 for examples of images that have been sectioned in various ways.

In one alternative, the user selects one or more images in step 1110 from a library of images. Alternatively, the user may upload one or more images.

In a second alternative, the system selects one or more images in step 1115 from a library or may upload one or more images.

In step 1120, the user selects the sectioning strategy for the image or images that the user selected in step 1115.

In step 1125, the system selects the sectioning strategy for the image or images that the user selected in step 1110.

In step 1130, whether the images are selected by the user or the system, the system generates composite images sets based on the images and the sectioning strategies chosen. At this point the system may immediately deliver Mem+ interactivities to the user (step 1155) or the User may select Mem+ protocols (step 1135).

In step 1130, whether the images are selected by the user or the system, the system generates composite images sets based on the images and the sectioning strategies chosen. At this point the system may immediately deliver Mem+ interactivities to the user (step 1155) or the User may select Mem+ protocols (step 1135).

In step 1140, alternatively, the system may select the Mem+ protocol based on the composite image set (step 1130).

In step 1145, the system delivers a word list recall activity to the user at time 0. The word list recall and WL recall methods are discussed in detail in FIG. 9 (see step 910). However, the embodiment of step 1145 includes a timed aspect. Optional visible timers may be used, as noted, above where each turn must be completed within a specified time frame, and in an embodiment, in some interactivities users are provided with a special piece that may need to be placed within a specified time to score the number of full points or to meet a specified threshold for error, time and/or reaction time. The reward and/or rewards attendant awards the rewards, when the piece is correctly placed by a user in compliance with an incentive program. In one embodiment, such a program is designed to encourage user compliance with a "you win" strategy to promote adherence to a protocol, to introduce new platform features and/or to include a special points earned to support and/or encourage user progress or completion of a task associated with an interactive protocol of any type.

The use of rewards in interactivities may include audio rewards, points in a game type setting, to indicate progress and/or regression when points are removed. The rewards may be incentivized tangible rewards offered through third parties such as coupons, discounts, tickets or other premiums, and/or intangible rewards such as a completed image set posted in a user gallery, and/or high scores/best times posted on a leader board depending on the configuration which can be designed for competitive game play for team building and/or for remediation and treatment with incentives offered for compliance with a therapeutic regimen. The rewards approach can be applied to the entire user interactive experience or to parts such as with the "special" interactive element (game piece) which has a reward above and beyond what may be included in generalized interactivity.

The use of a score or other composited value may be provided to the professional and/or user to assist them in measuring the effectiveness of the user's efforts and to identify areas of improvement and/or in need of improvement. The metric is factored with other "point in time" measures as well as the assessments delivered to the user as part of the baseline measurements and subsequent formative and summative assessments during a given protocol. The assessment design may be intra-activity, post-activity, or with 3' party assignments to domains+(multi-domain) comprehensive global (markers which demonstrate global cognitive engagement skills and processes, along with domain-referenced skills—local).

In step 1155, based on the word list (WL) recall, the system delivers Mem+ interactivities. In one embodiment, the Word List Recall is not included in an assessment battery and an alternative such as Object ID-Memory and/or Dimensional Descriptors can be used. In one embodiment, a language-based memory assessment may not be included though other memory assessments are included in interactivity battery to capture working, short- and long-term memory functions. The Mem+ interactivities can be any of those discussed herein. In some embodiments, the Mem+ interactivities may be chosen by the user, based on user preferences, and/or chosen by a health care professional.

In step 1160, a delayed recall assessment is delivered to the user at time 5 minutes. Meaning that the user has 5 minutes to complete the word list recall test.

In step 1165, the user provides the word list (WL) responses.

In step 1170, the user responses are scored. In step 1175, the user data is updated. In step 1195, the user baseline and/or progress metric is generated.

In step 1180, the system delivers Mem+ interactivities based on the WL responses in step 1165. In step 1185, a delayed recall assessment is made at time 15 minutes, but can be at other times in other embodiments. In step 1190, the user provides the WL responses. Based on the delayed recall assessment interactivity, the user's responses are stored, and which can include actual voiceprint recording data, and the user's responses are updated, and a progress metric generated (see steps 1170-1195).

In an embodiment, each of the steps of method 1100 is a distinct step. In another embodiment, although depicted as distinct steps in FIG. 11, step 1110-1195 may not be distinct steps. In other embodiments, method 1100 may not have all of the above steps and/or may have other steps in addition to or instead of those listed above. The steps of method 1100 may be performed in another order. Subsets of the steps listed above as part of method 1100 may be used to form their own method.

Figure 12A:
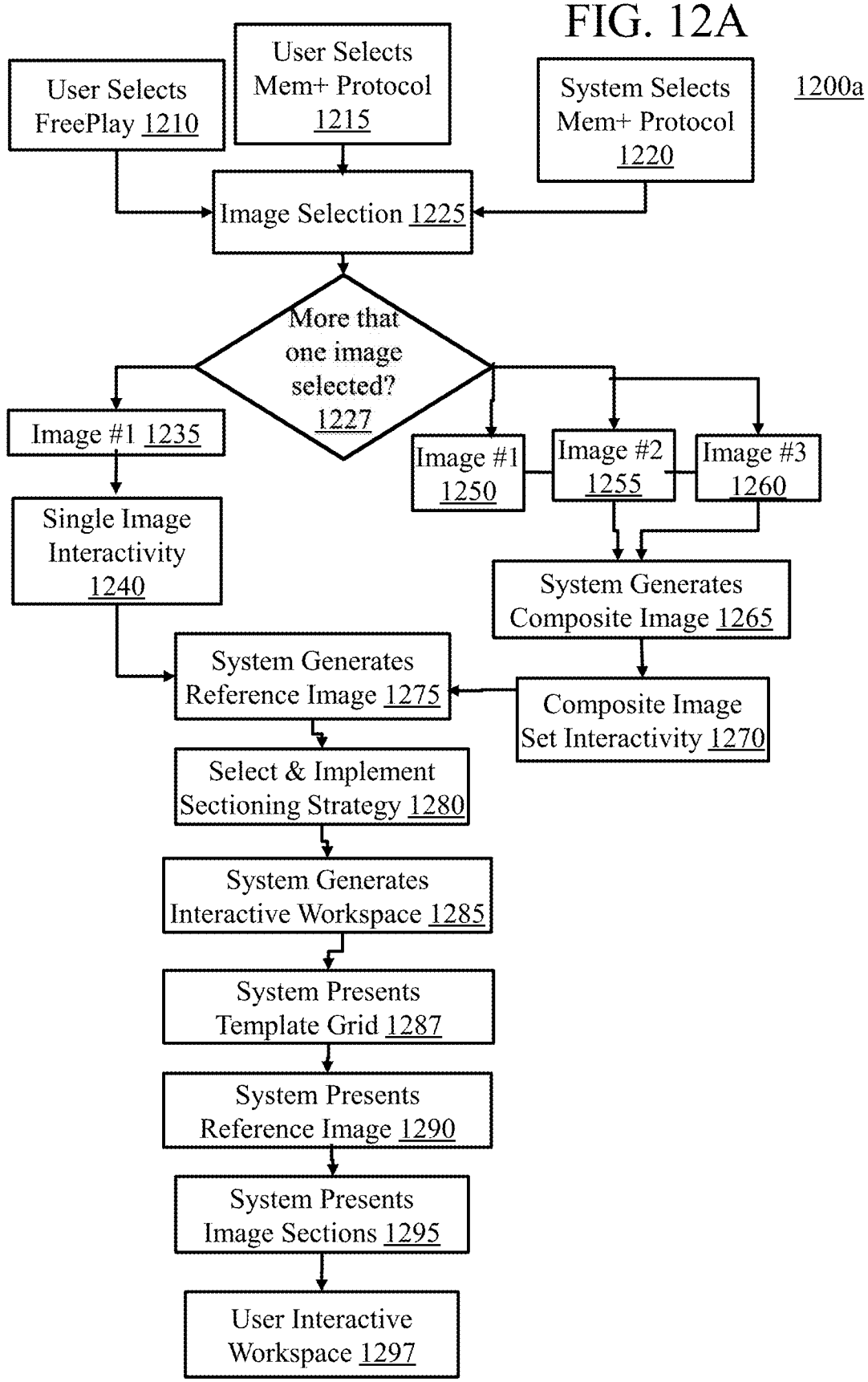
FIGS. 12A and B are an example of a method of making a user interactive workspace.
Figure 12B:
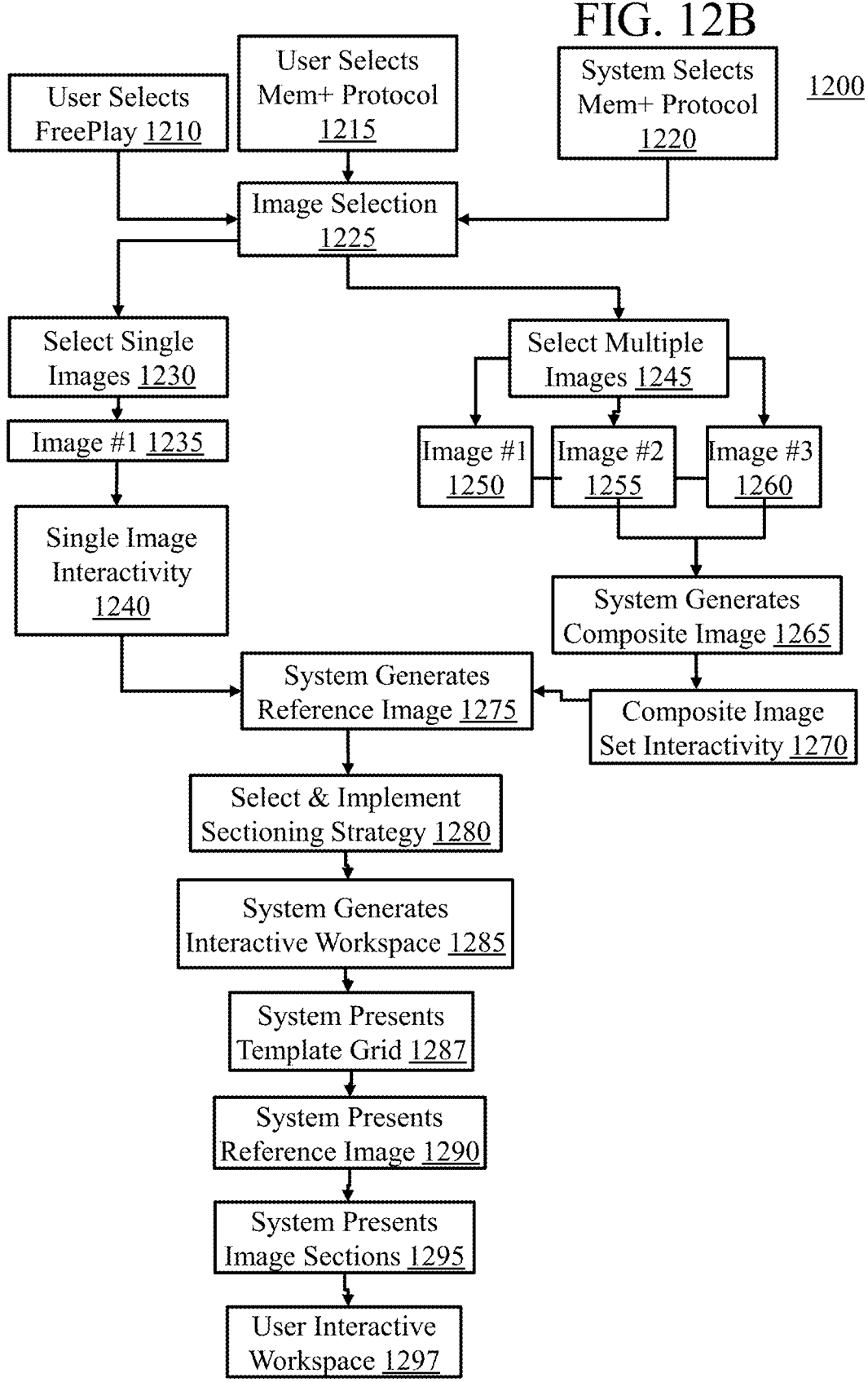

FIG. 12 is an example of a method of making a user interactive workspace 1200. The workspace may be produced in one of several ways. See FIG. 21 for an example of a graphical user interface or workspace. The user may be tasked to work through a series of interactivities using the individual images, and/or through a series of interactivities related to composites comprised of 2-3 component images where the individual component images are serially sectioned and juxtaposed to generate an interspersed pattern of non-adjacent component image sections. Interactivities may include hands-on as well, hand-free activities, such as view-only interactivities, where a hands-on interaction with physical and/or digital manipulatives is not necessary as a part of the process of working with the platform. Such interactions occur in the user/viewer's mind (user input may be received via a microphone and/or camera or in the case where a user is interacting with the platform on their own, there may not be any user input). As such, the view-only interaction of method 1200 is also termed as an interactivity because the view-only interaction requires the user's engagement, whether actively or passively conveyed to the user and whether the user is consciously or subconsciously engaged in the interaction. Assessments in View-only mode, however, require the use of additional biometrics type tools such as eye tracking and EEG, though speed and accuracy measures would not necessarily be available to users or for analysis. The lack of speed and accuracy data does not diminish the value of the platform, but does limit the availability of a subset of data for analyses and reporting.

In step 1210, the User selects FreePlay. FreePlay is discussed in FIG. 10 (step 1015). Alternatively, in step 1215, the user selects a Mem+ protocol.

Alternatively in step 1120, the system selects a Mem+ protocol based on the user information stored and provided when the user logs in.

In step 1225, in all cases (steps 1210, 1215, or 1220), a determination is made as to how many images are selected by the user. The image or images may be combined into 2-3 image composites where the individual component images are serially sectioned and juxtaposed to generate an interspersed pattern of non-adjacent component image sections.

Composite images can be made up of 2 or more component images which have been serially sectioned and the image sections from one image interspersed with another one or two images. Component images may be sectioned into two or more sections across their entire width and the sections juxtaposed next to sections from a second, and/or third image, such that sections from any one component image is not placed immediately adjacent to one another. Sectioned parts may be subdivided/sectioned further, and the user may be presented, for example, with half-height pieces, quarter-height pieces and smaller segments or pieces which span across multiple sectioned images. The gap between otherwise adjacent sections in a component image may be between 1%-50% of the image's total width, depending on specifications to effect the re-assembly of the hyphenated image segments to occur, despite the gapped appearance of the construct. The gap may be filled by a second and/or a third image, cut according to specifications or by white or other solid color spaces which can be viewed as a background substrate generated by placement of one of the images with a defined spatial gap between the image sections. In one embodiment, a solid white background can serve as a virtual or physical substrate for both online and offline manipulatives.

As noted previously, the serially sectioning and juxtaposition of multiple image sections in an alternating fashion generates the illusion of depth based on figure-ground relationship. The presence of one or more contiguities in a composite image can confer an additional aspect of the visual illusion in terms of the stability of the image which occupies the ground and/or background position. In one embodiment, the configuration may be referred to as stable when only one of the images in a composite contains at least one contiguity. The image with the contiguity occupies the ground position, and in the stable configuration, the second image in a 2-image composite; or the second and third images in a 3-image composite will occupy the figure (foreground) position. The image or images in the figure position can appear as columnar pop-outs supporting the portrayal of the illusion of depth. In a stable configuration the same image always occupies the background position. A multi-stable configuration one where at least two of the images in a 3-image composite or both images in a 2-image composite can occupy the background (ground) position; the switch capability as such is high for the image set. Both stable and multi-stable constructions can be generated using either the platform's device-based and/or offline components, and/or a hybrid version.

In both stable and multi-stable embodiments, the image in the ground position can be viewed by the viewer as being intact, confluent, despite the spatial hyphenations between sections and where these spatial gaps are largely ignored. This gap filling (perceptual completion) can occur when the intervening spaces are filled with one or two content-rich images and/or when the gap space is filled with a solid color, such as white (empty space). The dynamic re-assembly of the hyphenated image segments of the image occupying the ground position can occur based on the presence of visual, context, and knowledge-based cues as part of the user/viewer's experience base and predictive inferences, continuity, together with gap-filling (perceptual completion) capacity of the information conveyed by and through the contiguities present in the image.

For example, a green-blue colored interface extending across the entire width of the image can potentially be identified by the user as a field/sky interface based in part on the color of different regions and spatial characteristics, and the user's knowledge of field and sky. The regularity and continuity of the interface can be anticipated by the user and the intervening disruptive and/or distractor image sections are largely ignored as the viewer tracks the next image section containing a green-blue interface. Interference can be established with the choice of intervening images and overlapping contiguities between the component images including the image set. Together the Gestalt principles of figure-ground, closure, continuity and gap filling (perceptual completion) can be used to understand the scientific basis of the visual illusion and its applications in the platform for assessment, diagnostics, remediation and training purposes. Continuity refers to the mind's tendency to complete a continuous region.

In describing figure and ground relationships, the terms of recessive and dominant can be used, respectively. Dominant may be used to refer to the image which assumes the ground position in a fixed and/or dynamic fashion in a stable configuration, or images in a multi-stable condition, respectively. In the stable condition, the figure position is then occupied by the other image in a 2-image composite or 2 images in a 3-image composite, if neither of these images contains a dominant contiguity relative to the image occupying the ground position.

For a multi-stable composite, the presence of at least one contiguity in at least 2 of the images in a 2- or 3-image composite, the composite image will generate a multi-stable image, and/or that each of the three images in a 3-image composite each has at least one contiguity will also generate a multi-stable image.

The term multi-stable refers to the ability of more than image, or image section or part to assume the ground position (with a concomitant flip or switching/shifting of the previous ground occupant to a figure position). A multi-stable, figure and ground relationship in an image set is where the images can be perceived in more than one way, i.e. the perception of the image set changes/switches. This flip or switch can occur spontaneously and the different forms are referred to as percepts. In these types of embodiments, the image which occupies the ground position dynamically shifts between the image and/or images in the figure position at a given point in time and is perceived in an alternate fashion by the viewer. Both stable and multi-stable image sets share the illusion of depth, but differ in their switch/shift capacity as described previously and in the following sections.

Not all percepts are equally stable and dominance is relative to the composite's composition. For example, if the component images in a stable 3-image composite are extracted and reassigned to a 2-image composite, a previously figure-bound image in a 3-image composite can assume the ground position, because of a relative state of contiguity dominance. In other words, a weak contiguity can be in the ground position relative to a composite with a second component image with weaker contiguity characteristics, but be relegated to the figure position in a stable composite if the weak contiguity is dominated by an image with a contiguity with stronger characteristics. In part one reason that a weak contiguity may occupy the ground position relative to a composite with a second component image with weaker contiguity characteristics is due to the presence of a minor contiguity whose contiguity characteristics while present were otherwise perceptually masked in the 3-image composite or a 2-image composite, but which can be expressed in certain combinations of the derived 2-image composite and/or in combination with other images.

As such, in one embodiment, an image with a weak contiguity can be combined with one or more images which do not contain any contiguities, making the image with the weak contiguity the dominant image and when the sections are combined, the image with the weak contiguity can assume the ground position. The hierarchy in which the image with the highest contiguity assumes the ground position can be driven in part by the contiguity's characteristics and user's/viewer's input and/or bias and/or preferences. The multi-stable capacity is nonetheless conferred on an image based on the individual image's absolute contiguity characteristics and are metered by the combination of the image with other images in terms of the expression of the contiguity. FIGS. 25A-C uses the same set of three images in multiple combinations which can be described as 2:3, 1:2 and 1:3 to demonstrate hierarchical dependencies. In this example, Image 1 in FIGS. 25B and 25C is dominant to Image 2 and Image 3. Both Images 2 and 3 would appear to portray similar figure position tendencies, but when Images 2 and 3 are combined in FIG. 25A as figure-ground hierarchy places Image 2 in the ground position relative to Image 3.

In both stable and multi-stable images, the image which occupies the ground position, with or without a perceptual switch, can be perceived and conveyed to the user as a coherent image, intact despite the spatial separation between the image sections, and their disruption with interspersed content-rich image sections and/or blank spaces if the second (or third) image(s) are solid in color, and which can be viewed as distractor or attractor elements, depending on their use. This gap-filling capacity despite the hyphenation is consistent with the Gestalt principle of completion, which is that the mind tends to complete an image.

The integration of multi-stable images into the cognitive platform allows for dynamic cognitive engagement of the user with the composited image sets, whether in a conscious and/or unconscious mode as perceived by the user/viewer. This engagement is facilitated by selecting and using image sets of differing complexity for select training and treatment modalities, together with the interactivities mix. Contiguity characteristics form the basis of developing a complexity rating for images based on their ground position capacity and/or switch capacity depending on the image configuration together with image content, color and context variables. The prospective image combinations can be defined according to a set of rules where a composited image scene can be categorized as stable and/or multi-stable, and with a determination in the stable condition which image will assume the ground position, with assignments to varying complexity levels for the various interactivities.

In multi-stable image sets, the switch frequency can vary between users and as a function of cognitive status related to: age as a factor and/or neuropsychological conditions, such as schizophrenia and autism.

Switching events and, as such, switch frequency for multi-stable images have traditionally relied primarily on user-identified switch events which are signaled by a click of a mouse or other type of device to indicate conscious awareness of a switch event. In general, the images used for measuring altered switch rates are binary ambiguous images, in that the switch occurs between two alternate perceptual states (percepts) within the same image. Examples of these types of images include the Necker Cube and Rubin Wine Glass-Face illusion. The multi-stable image sets used in the platform involve a switch between different images, guided in part by the user tracking (e.g., moving the user's eyes) across a given contiguity or towards salient image parts. As such, interactive measures and/or an analysis of switch rates among different population groups can be improved and used as a diagnostic tool using both user-identified switches combined with objective measures such as eye tracking analysis to detect a shift in the user's gaze or eye focus from the spatial location of a contiguity in Image #1 to a contiguity in Image #2 and/or Image #3. Optionally, throughout this specification, any time an eye is tracked, the eye may be tracked automatically via a camera in system 100, and analyzed by the processor system of system 100 or 200. Switch events such as eye tracking can also be monitored using EEG tools in part, because of the integration of real-world images into these dynamic image sets and the recognition/discovery process which can occur when the ground image becomes confluent coincident with and/or part of a switch event. The potential for identifying evoked/event response potentials together with eye tracking data, as well more sophisticated biometric and analytical tools, can be used to improve these measurements and assess their potential value as part of a diagnostic profile of cognitive function and status.

Figure 23A:
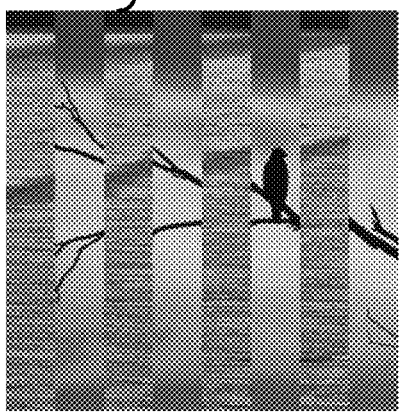
FIGS. 23A-F show examples of two-image composite images where the contiguity has been serially removed, stabilizing the figure-ground relationship.
Figure 23B:
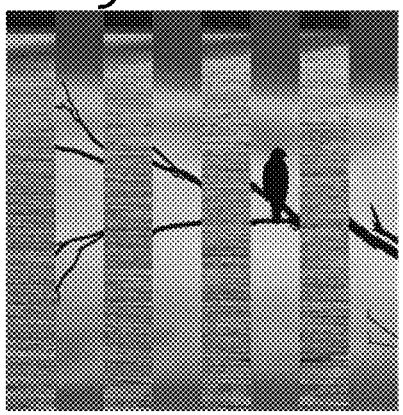
Figure 23C:
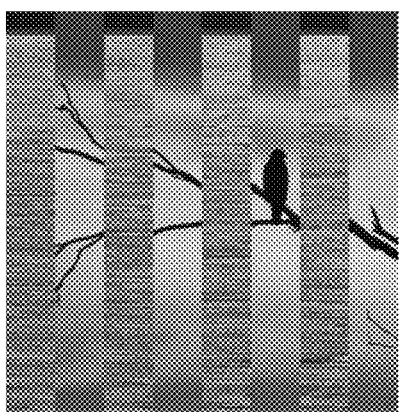
Figure 23D:
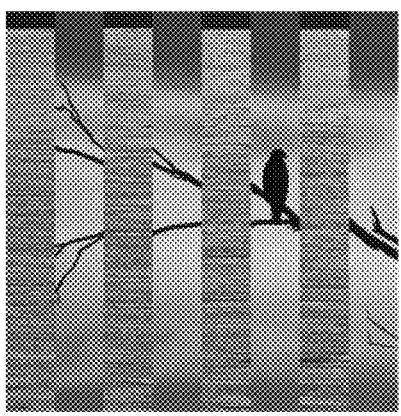
Figure 23E:
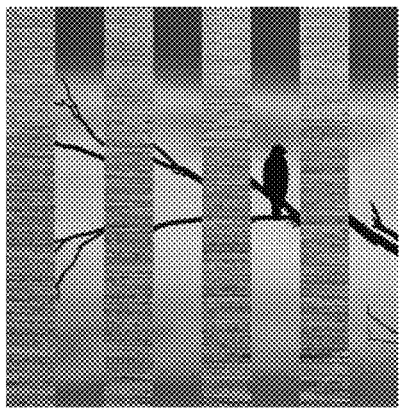
Figure 23F:
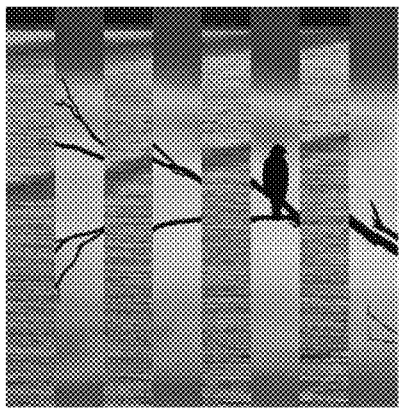

In one embodiment depicted in FIGS. 23A-F the multi-stable nature of an image set can be shifted to a stable configuration by selectively removing one or more contributing contiguities which otherwise positively enables the image set's switch capacity. The shifting between switch and non-switch and back to switch capable image sets can be incorporated as part of a training protocol (or a testing or therapeutic protocol). FIGS. 23A and 23F are identical but are placed separately to show the multi-stable to stable progression and differences between the "fully-switch capable" multi-stable image set to the stable "fully-switch incapable" stable image set. Shifting between switch and non-switch and back to switch may be used to impact one or more cognitive domains, including the translation of response times from changes in processing speed parts attributable to switch speed for attention focusing.

If it is determined in step 1225 that a single image interactivity is desirable, the method proceeds to step 1230, and a single image algorithms loaded. In step 1235, system offers the user a choice of images to select. After receiving a selection, the system proceeds to step 1240. In step 1240 a single image interactivity is produced based on the single image selected.

If in step 1225 it is determined that the user would like to select multiple images, in step 1245 the user is offered a multiple image to select from and is allowed to select multiple images. In step 1245, algorithms for creating multiple-image interactivities are retrieved. In step 1250, Image #1 is selected, in step 1255, Image #2 is selected, in step 1260, Image #3 is selected. In some embodiments, more than three images are selected. In some embodiments, two images are selected. In some embodiments, three images are selected. In one embodiment, in composited image scenes at least one of the images (Image #1) may contain real-world content portrayed as a photograph, graphic, painted or as a constructed image including a tangible prop or other type of physical and/or digital manipulative, while at least one other image (Images #2, #3 and/or #4) can contain content and be presented in a format similar to Image #1 or can consist of a solid color or mix of solid colors including: white, black or gray tones of varying percentages or other type of illustration. The sectioning strategy may be uniform or variable for one or more of the images. The juxtaposition strategy may be sequential, non-sequential, may include partial or full masking (skipping) of one or more image sections, and/or use a solid color image giving the appearance of unfilled gaps between image sections. Sectioning strategies may be uniform for each of the component images between 1% and 50% and/or portray a mixed sectioning strategy, depending on the construct, where each image may follow an independent sectioning strategy and may itself portray a mixed sectioning strategy. The variation in sectioning can contribute to the designated skill level for one or more of the platform's interactivities. In general, the thinner and/or smaller the image sections, the more challenging the interactivities and the user's cognitive demand requirements to focus their attention on the contiguities and/or component elements of an image for assessments, including embedded assessments for memory and/or attention based in part on the amount of available information which can be used for cueing and pattern analysis to identify parts of the whole. In one embodiment, the impact of the sectioning strategy, 10%, 12.5%, 20%, 25% and 50% for example is adjusted with a weighted factor, reflecting the availability of image content cues and image details within the image sections for facilitating the user's analyses of the image set's content and the complexity level to solve the interactivities. In one embodiment, a 20% sectioning strategy may lend itself to ease of use as compared to both a 25% sectioning strategy or a 10% sectioning strategy because of the ease of access and/or hyphenation of content in more refined sectioning strategies within a sectioning strategy range, a "sweet spot" so to speak.

In one embodiment, a progressive reduction in the sectioning width, and/or an increase in the number of sections conveyed to the user for part of the image, can be used as part of training protocol to convey attention focusing skills development through an increase or decrease in the sectioning used and the subsequent interactivities used for one or more of the images in a composite image set, and/or individual images with associated interactivities.

In step 1270, a composite image set interactivity is produced based on the selected images.

Based on these images, the system creates a user interactive workspace. In some embodiments, "user-interactive" means that at least one user-preference was incorporated into the workspace. In step 1275, the system generates a reference image. The user can be provided with a reference image. The reference image can be presented in several modes: continuous, intermittent, preview, limited and/or on-demand display mode. The reference image can serve as the source of the visual cues where the user can match to and/or work with associated manipulative elements related to the reference image towards working on and completing a task. The non-continuous display of a reference image for an interactivity and/or set of interactivities increases the cognitive requirement for memory and attention. As described for sectioning strategy, factors are applied to adjust the weighted values for each cognitive domain's representation/contribution to the multi-domain character for each interactivity. In one embodiment, the user is provided with a reference image by which to model their tasks for a subset of the platform's interactivities but with variable engagement of multiple cognitive domains as compared to intermittent, preview or on-demand use of reference images.

In one embodiment, where the reference image is presented as a composite image set, the user's referencing of the image to perform associated tasks can provide for additional interactivity based on the platform and the composite image sets' view-only capacity for interactivity based on cognitive engagement—a factor which is differentially weighted into the multi-domain character of the interactivity and its contribution with a battery of interactivities (see the Appendix). The additional image set interactions based on the user's referencing of the image set can be viewed as a value-add and which is delivered via the cognitive platform's presentation of a reference image to the user and the use of the reference image by the user.

In an embodiment, reference images can be presented to users for a specified period of time and/or can be available throughout the interactivity session and/or previewed for the user prior to the start of the interactivity, and/or is available to the user on-demand, depending on the requirements of the treatment and/or training protocol.

In step 1280, the system selects and implements a sectioning strategy, in step 1285, the system selects or generates an interactive workspace using the sectioning strategy and the images chosen, which may still need to be populated with an image and images sections. In step 1287, the system selects or generates a template grid. In step 1290, the system presents the reference image. In step 1295, the system presents the image sections. In step 1297, the user interactive workspace is developed using the image or images selected.

In an embodiment, each of the steps of method 1200 is a distinct step. In another embodiment, although depicted as distinct steps in FIG. 12, step 1210-1297 may not be distinct steps. In other embodiments, method 1200 may not have all of the above steps and/or may have other steps in addition to or instead of those listed above. The steps of method 1200 may be performed in another order. Subsets of the steps listed above as part of method 1200 may be used to form their own method.

Figure 13:
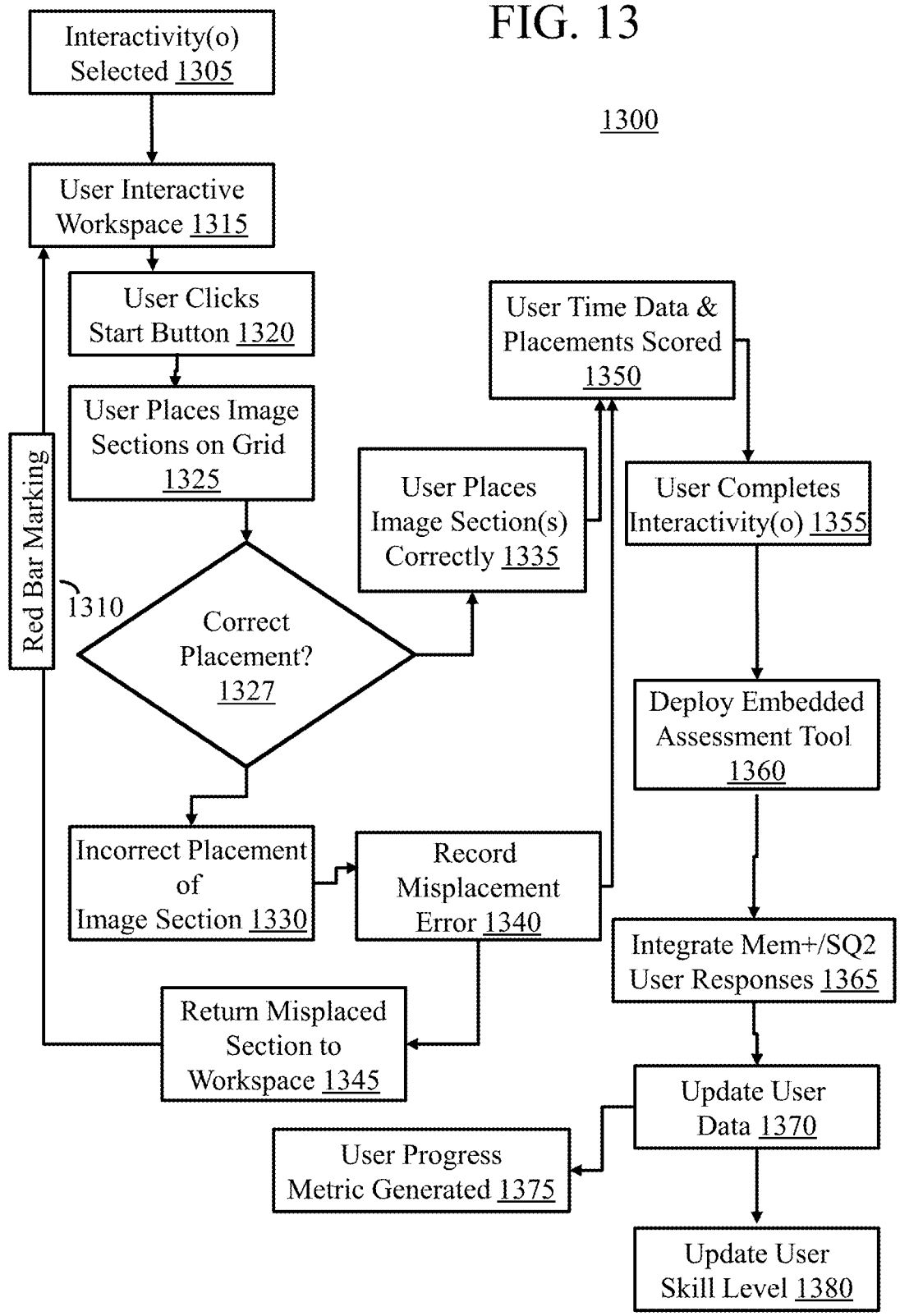
FIG. 13 is an example of a method of a user interacting with a cognitive platform to generate a metric and/or update a user skill level.
Figure 14:
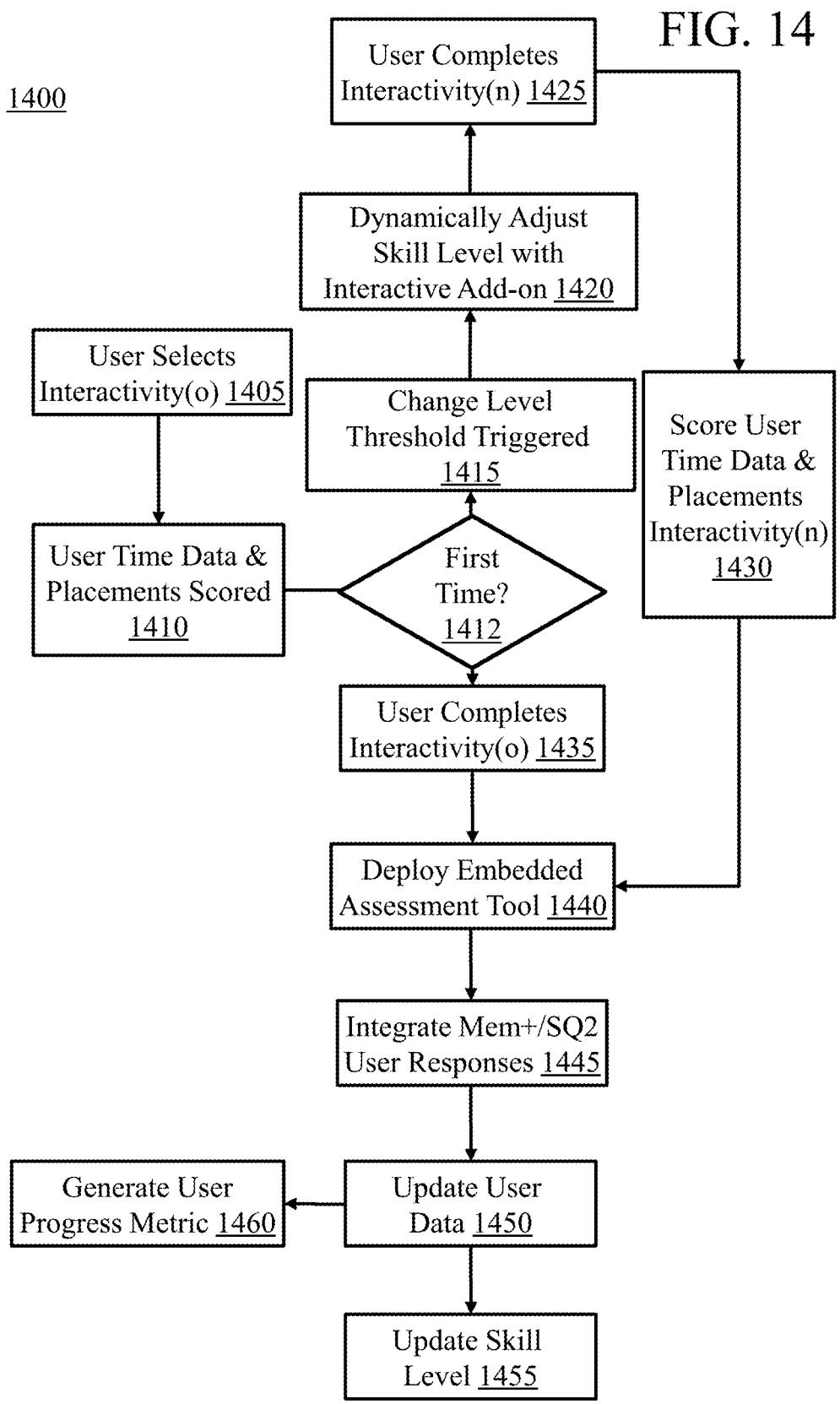
FIG. 14 is a second example of a method for interacting with a cognitive platform by a user (see also FIG. 13).

FIGS. 13 and 14 provide embedded assessment tools which are part of the interactive cognitive platform. A key component of the platform is the embedded aspect of the assessments across multiple cognitive domains, which is integrated with the interactivities and which extends the assessment capabilities to include other metrics beyond intra-activity speed and accuracy measures and sub-measures. The user can be tasked to work through a series of interactivities using the individual images, and/or these can be combined into 2-3 image composites. Interactivities can include hands-on as well, hand-free and in particular view-only interactions, where hands-on interaction can occur with physical and/or digital manipulatives but which is not necessary as a part of the process of working with the cognitive platform as physical reassembly is complemented by virtual assembly of the hyphenated image parts which can occur in the user/viewer's mind. As such, this view-only interaction is also termed as an interactivity because the view-only interaction requires the user's engagement, whether it is conveyed to the user, actively or passively.

The integration of both dynamic and stable aspects of the image sets, together with the interactivities multi-cognitive domain engagement, and by default assessment capabilities, together with, but not limited to platform personalization through image selection and interactivity features, skill level scalabilty, demographic-neutrality, multimodal (View only, Hands-On) use including: self-directed, group and/or facilitated use with the use of a hidden timer and/or untimed interactivity based assessments, and other features make the invention a versatile multi-purpose platform suitable for use across a range of user capabilities and in multiple user environments.

FIG. 13 is an example of a method of a user interacting with a cognitive platform to generate a metric and/or update a user skill level 1300.

In step 1305, an interactivity (0) is selected by a health care worker or user. Interactivity (0) refers to an interactivity which has not yet been personalized to a user.

In step 1315, a user interactive workspace is provided for the interactivity (0). In step 1320, system waits to receive input from the user, such as click on a start button. The user starts the interactivity (0) by first clicking the start button when he or she is ready (step 1320) and then in step 1325, system waits to receive a placement of an image section on a grid (step 1325) where grids are used in a Compose, Construct, Missing Pieces and/or Extrapolation interactivity, for example.

In step 1330, if the system determines that the user incorrectly places one or more sections, an auto-alert element indicates the incorrect placement to the user. In an embodiment, in the all-edge design, all placements are possible because of the elimination of specific fitted shape restrictions. In some embodiments, in the digital version of the platform, the user can be alerted to a misplacement with visual and auditory alerts, and/or kinesthetic and or vibratory indicators of correct, incorrect placements, and/or can be used to provide proximity hints to the user. In some embodiments, as the user places an element incorrectly, the misplaced element can be automatically returned to the "active" interactivity space or gameboard area, and can be marked or tagged as having been tested and/or tried by the user. In some embodiments, a visual signal (e.g., a red bar) is placed above used pieces which have been incorrectly placed by the user. However, other graphical or sensory methods can be used to indicate incorrect placement. In an embodiment, the user is given the chance to correct the placement until the placement is correct (in another embodiment the user may be given a finite number of chances to correctly place a piece, such as between one and 30 chances to correctly place the section on the grid). In some embodiments, the user is given the option to change the skill level if the placement is too difficult (e.g., if the user tries more than 5 times to correctly place the section on the grid and does not accomplish correct placement). In some embodiments, the interactivity will go on to the next step if the user cannot correct the placement after a present number of tires, such as one and 10 tries.

The alert systems may be configured to allow the user to receive dynamic feedback to correct near-completed and/or actual misplacements; or the alert may be dispensed with to allow the user to complete the placement of all game pieces without feedback and then be scored at the completion of the task. Depending on the protocol, the user can be given an opportunity to correct misplacements for the purposes of achieving a better score, and/or for learning purposes about missed visual cues and cognitive skills development, including second choice or second best choice options. A secondary digital interface such as a phone, tablet computer, or other type of smart device can also be used to scan or capture an image of the user's completed interactive task and results conveyed to the platform's assessment module for scoring purposes.

In step 1335, the user is presented with an opportunity to correct the incorrect placement. In step 1340, the misplacement error is recorded. In some embodiments, the number of times required for the user to correct the incorrect placement is also recorded. Tracking of user errors and categorization of error types, including repeated attempts of placements in the same location provides insight in user strategy and decision-making (random versus targeted), attention, memory and other cognitive considerations.

In optional step 1345, the misplaced section is returned to the workspace (in an alternative embodiment, the misplaced section is left where placed, optionally with a visual indication that the placement is incorrect), and in step 1350, the user time, data & placements are scored. A time may be recorded after the user clicks the start button (step 1320) to record time information, after the user places an image section correctly (step 1335), after the user completes the interactivity, and/or after a misplacement error (step 1340).

In step 1355, a determination is made that the user has completed interactivity (0), which may occur when the image has been properly constructed or other interactivity task completed, the system indicates the user has completed the task, and/or after the user has spent more than a predetermined about of time with the interactivity. In step 1360, the embedded assessment tool is deployed—the interactivity is assessed. The embedded assessment tool may compute and/or recompute other test other metrics, such as those in step 1365 and the WL recall tests, based on input from the current interactivity. Thus, in step 1365, the Mem+/SQ2 is integrated with the user's responses to the interactivity. Word List Recall assessments and SQ2 questions are image-based evaluations integrated into and with the interactivities, allowing for a more sensitive and accurate assessment of the user using the platform which can be metered to address a user's changing and evolving status and/or requirements.

The platform's embedded assessment tools therefore include an evaluation of number of correct/incorrect responses, time taken to complete an interactive task, pattern of errors together with the recall/delayed recall and extended delayed recall, and SQ2 responses to provide a usable metric to help assess a user's cognitive capacity relative to baseline measures and other measurements taken as points in time and/or at defined interval as part of a clinical and/or research protocol, and/or other comparative measures, including a Big Data analysis of user data obtained from a sample pool and compared across user data, physical and physiological variables including: age, sex/gender, diagnosis, stress levels, EEG, education, professional positions and/or potentially other contributing variables.

These data contribute to the user profile in building both point in time and changes over time metrics based on user data, as well as contributing to large cohort analytics (Big Data), including the integration of third party data towards informing the platform's evolution, an approach which uses a continuous improvement model for product research and development to meet current and future user needs, and for developing predictive analytic benchmarks for a broad range of uses, including: diagnostics and change monitoring.

In step 1370, the user data is updated based on the integration and, in step 1375, the user progress metric is generated. In step 1380, based on the interactivity and the embedded assessment, the user skill level is updated.

In an embodiment, each of the steps of method 1300 is a distinct step. In another embodiment, although depicted as distinct steps in FIG. 13, step 1305-1380 may not be distinct steps. In other embodiments, method 1300 may not have all of the above steps and/or may have other steps in addition to or instead of those listed above. The steps of method 1300 may be performed in another order. Subsets of the steps listed above as part of method 1300 may be used to form their own method.

FIG. 14 is a second example of a method for interacting with a cognitive platform by a user 1400 (see also FIG. 13). FIG. 14 provides possibilities for what happens after a user selects an interactivity.

In step 1405, the user selects an interactivity (0).

In step 1410, the user time, data and placements are scored. At this point, based on the scoring in step 1410, the user may either complete the interactivity (step 1430) or a change level threshold may be triggered (step 1415) based on the previous progress or results by the user and/or the progression of the user's cognitive disorder. In some embodiments, the change may be due to the fact that, as a user practices the types of interactivities provided, the user may get better at them and may require a higher skill level.

In step 1420, after the change level is triggered, the skill level is dynamically adjusted by the system with an interactive add-on.

In step 1425, the user completes the new interactivity (n)

In step 1430, the user time, data and placements in the interactivity (n) are scored.

In step 1435, if the change level threshold is not triggered, the user completes interactivity (0), not interactivity (n).

In step 1440, the embedded assessment tool is deployed after completion of either interactivity (0 or n), after either step 1430 or after 1425.

In step 1445, the Mem+/SQ2 user responses are integrated with the assessment of the interactivity. In an embodiment, Mem+/SQ2 is used as an example of a post-activity assessment (beta category assessment) as described in conjunction with FIGS. 25 and 26.

In step 1450, the user data is updated, the skill level is then updated in step 1455, and/or the user progress is generated in step 1460.

In an embodiment, each of the steps of method 1400 is a distinct step. In another embodiment, although depicted as distinct steps in FIG. 14, step 1405-1460 may not be distinct steps. In other embodiments, method 1400 may not have all of the above steps and/or may have other steps in addition to or instead of those listed above. The steps of method 1400 may be performed in another order. Subsets of the steps listed above as part of method 1400 may be used to form their own method.

With reference to FIGS. 1-14, in some embodiments, two or more of the platform's components can be combined. For example in a Stress module, a suggested sequence of interactivities may be provided to the user in response to an assessment and/or the user may elect to use the platform in a self-directed manner accessing a user-defined module which allows the user to select the image sets, the interactivities, the skill level and the optional use of a timer. The user's interactivity statistics are analyzed, recorded and stored, and can be presented to the user to help inform platform-assisted recommendations and/or the user's own decisions. The platform can be integrated with additional devices, including tablets, phones and other touch-mediated devices and/or add-ons and/or equipment which allow for the monitoring of physiological metrics including but not limited to: multi-channel EEG, single channel EEG, heart rate, respiratory rate, blood pressure, galvanic skin response, pupil dilation, temperature and other spatial, temporal and/or frequency brain states as assessment tools.

FIGS. 15-18 provide methods for use of the platform by a professional to create a specific cognitive diagnostic or test. In the platform, the term "professional user" can refer to a clinician, a researcher, a healthcare worker, a professional game maker or gamer. The platform is designed to allow for dynamic configurations and the assembly of the elements to generate personalized game boards, and interactivity batteries based on user preferences and/or health care worker-based inputs for therapy and/or diagnostic and/or assessment or other professional purposes ("professional"), as well as configurations generated by system AI logic in evaluating a user's preferences and/or cognitive requirements.

Figure 15:
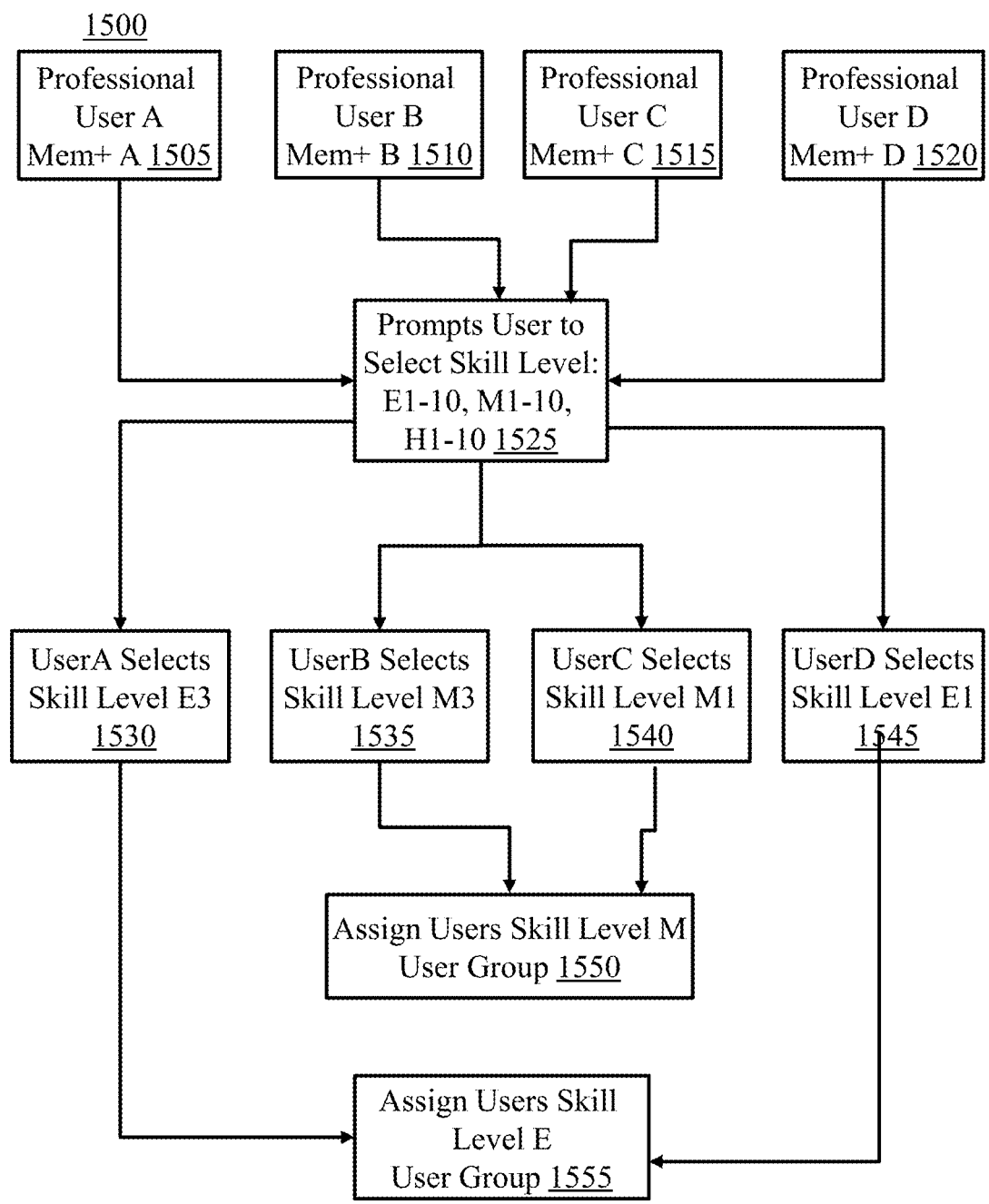
FIG. 15 is an example of a collaborative method in which professional users (e.g., health-care workers) analyze data from users based on skill levels.

FIG. 15 shows a method 1500 for allowing professional users to build diagnostic, assessment, treatment, and training tools. Professional communities would be able to use a menu of choices and branched options to establish interactivity parameters towards building their own protocol configurations (Protocol configuration builder). Configurations can be stored under a Mem+ label towards building a dynamic library of diagnostic, assessment, treatment and training tools to support cognitive well-being and skills training FIG. 15 is an example of a collaborative method in which professional users (e.g., health care workers) may analyze data from users based on skill levels 1500. The method in FIG. 15 may be used by a health care worker for treatment or diagnosis of a disease, or for understanding a diagnostic tool, producing an effective treatment, producing an effective diagnostic tool, producing an effective treatment tool, and/or for research into understanding brain, neuronal and neurocognitive processes for example. In some embodiments, the method can be used in combination with other treatments (to analyze their effectiveness) or with other diagnostic tools. FIG. 15 shows collaboration between four professional users, but in other embodiments, collaboration can take place between any number of professional users from 2 to 100s or 1000s or more. Professional users may include, but are not limited to, health care workers, analysts, professional game makers, and/or gamers. Professional users typically do not include patients or those that interact with interactivities for training, therapy, and/or testing themselves, but the collaborative space can provision for interactions between professional users and enrolled users in a trial or study where researchers can virtually interact with users and/or study participants.

In steps 1505-1520, Professional users A-D create Mem+ A-D. Mem+ interactivities are discussed in detail in FIG. 10. However, also included in the Mem+ interactivities are interactivities that can be done in view only mode (VO) and/or hands free mode. These are particularly useful for users that have patients with diseases where patients no longer have the use of their extremities, cannot speak, and/or have difficulty with speaking or physical movements including temporary situations such as following the administration of general anesthesia where recovery of cognitive functions can be temporarily slowed. Under these circumstances, one way to diagnose is to observe patterns of what part of the brain is active during an interactivity. For tracking progress, the part of the brain that is active can be tracked over time and/or with treatment. The part of the brain that is active can be compared to that of a normal individual (one who does not have the cognitive disease) for diagnosis and treatment tracking. In some embodiments, parts of the patient's brain may be compensating for damaged parts of the brain and/or the patient's may also be trained as part of doing the interactivities.

View only may be referred to as Virtual/View-only (VVO) mode. For any hands-on interactivities or if the user has limited or no fine/gross motor control, the user does not have access to eye-control technology or the person has limited or no ability to communicate verbally. VVO allows the user to use other methods for approaching the interactivities for cognitive benefit to them. For example, when looking at the image sets—stable or multi-stable—the mind is engaged in resolving the ambiguities, in discerning figure and ground relationships, in re-assembling the hyphenated image parts into a confluent image. This type of engagement can be trapped, tracked, and imaged using eye-tracking, fMRI, EEG/ERP and other physio biometrics to identify cognition in the user. EEG and ERP are methods of measuring brain activity. Electroencephalogram (EEG) is a test used to evaluate the electrical activity in the brain. Brain cells communicate with each other through electrical impulses. An EEG can be used to help detect potential problems associated with this activity. An EEG tracks and records brain wave patterns. Event Related Potentials (ERP) are measured in EEG. For example, the health care worker says "flower" and the eye tracking shows eye movement to the flower region of the image set. If the health care worker then says "yellow flower", there is specific eye movement to a yellow flower. In some embodiments, to refine (temporally and spatially) these kinds of signals, EEG/ERP signals (or fMRI) can be matched to image recognition. Further, the system can discern the switch between the component images in an image composite, for example, done with the user clicking a button and saying switch. The process can be refined by applying technology to demonstrate and characterize the switching phenomenon, which can be done because the platform integrates the use of both stable and multi-stable images, and transitional image sets where a multi-stable image can be turned into a stable image and in the reverse sequence as well. This can be done because there are hierarchical relationships between contiguities and in image combinations (1:2:3 versus 1:2 versus 2:3 versus 1:3) image driven differences which are processed differently as shown in the figure-ground positioning hierarchies in FIG. 25. It is no longer just random parts that user perceives, but rather parts of the whole, and/or the whole itself. Because of this, these properties can be linked to interactivities and assessments. For example—the user has a stable image set and is asked to describe what they see. That process is different when using a multi-stable image set where the user must concentrate (prevent attention shifting and ignore the flanking content) to describe each component image's content individually.

The platform's hands-free mode is to be distinguished from the view-only mode which is also hands-free and involves engagement of the user. The hands-free mode refers to the use of an alternative user adaptive type of input devices or other assistive technologies such as eye-control, mouse cursor control, voice-activated controls, and/or brain-computer interfaces, and/or another type of intermediary device or tool for the device-based platform components and/or offline and/or hybrid-type components. The use case for this modality can also be where the user is not impaired in terms of the user's manual dexterity but where the user requires the use of their hands for other purposes or functions. Such a device can include Virtual Reality/Augmented Reality and/or mixed reality training devices such as pop-up displays on visors, helmets and/or glasses and/or holographic type projections. For some users a Tangible User Interface (TUI) may be preferable to the graphical user interface (and/or the keyboard). Examples of TUI can include a physical puzzle piece with or without other embedded sensors (grip strength, grasp, galvanic skin response, pulse) and/or equipped to detect and track motion.

In step 1525, the system prompts a professional user to select a skill level. In some embodiments, the skill level is a mixture of the sectioning strategy, the number of images, interactivity mix, image content and thresholds to evaluate a new category of users from a clinical research and/or training standpoint. In some embodiments, the skill level is chosen from E1-10 (Easy1-10), M1-10 (Medium 1-10), or H1-10 (High 1-10), where each of E1, E2, E3, . . . E10 are different skill levels, each of M1, M2, M3, . . . M10 are different skill levels each of H1, H2, H3, . . . H10 are different skill levels, which labeled sequentially according to increasing or decreasing degrees of difficulty. In some embodiments, a 1 is the easier level and a 10 is the highest level within a skill level bracket.

Leveraging complexity variables as a function of the platform's skill levels, combined with the "game is not the only assessment" approach gives the platform a powerful capacity and versatility to address a multiplicity of cognitive issues and/or learning and/or training situations. For example, the number of interactive elements (game pieces); image content; image type, including: photographs, artwork, line drawings, color, and/or halftone, b/w; number of images (2+) used in a composite; size of the elements; the content character of the elements-high/low detail and color variability; spatial assignment of the elements; the presentation mode of the elements-grouped or random, single elements; individual image sectioning strategy, such as: 1:2 (50%), 1:4 (25%), 1:6, 1:8, 1:10, 1:12, 1:15, 1:20, and/or higher/lower percentages; fixed, mixed or variable sectioning strategy between the images and within an interactivity; type of interactivity mix for both component/single images and/or composite images; hint availability and use of reference images, timed/un-timed interactive components; time constraints (time to completion requirements); AI adaptations and tolerance/threshold levels; word lists and number of words to be recalled in an assessment protocol; SQ2 questions, number of questions and level of difficulty; among other elements can be modulated to meet a user's needs and/or user groups' assessment, learning, remediation, and/or training needs.

In steps 1530-1545, each User (A-D) selects a skill level. For a given interactivity, the size and width of an image's sections, together with the image and/or image set's complexity can be varied to reflect a user's skill level and/or changes to their skill level, and/or abilities to make dynamic adjustments to gameboards and game pieces in assessing and challenging cognitive function on a global cognition basis (multi-domain), but with a particular focus on attention and memory, and in general towards evaluating the user's strategy and problem-solving abilities using the interactivities in terms of user process, solution-finding, task completion and follow-up assessments.

In step 1550, the system assigns the users of the same skill level (E, M or H) to a user group. For example, in step 1550, User B and User C are put in the same group because User B and User C selected skill level M and in step 1555, User A and User D are put in the same group because User A and User D selected skill level E. In some embodiments, setting multiple users to the same group allows the professional users to better analyze the progress of a user by comparing that user to other users of the same skill level as a cohort. The professional user may also identify whether a user needs to be moved to another skill level based on this comparison or in other embodiments the system's AI logic may initiate recommendations or depending on the configuration automatically perform skill level or other adjustments to user interactions with the platform.

In an embodiment, each of the steps of method 1500 is a distinct step. In another embodiment, although depicted as distinct steps in FIG. 15, step 1505-1555 may not be distinct steps. In other embodiments, method 1500 may not have all of the above steps and/or may have other steps in addition to or instead of those listed above. The steps of method 1500 may be performed in another order. Subsets of the steps listed above as part of method 1500 may be used to form their own method.

Figure 16:
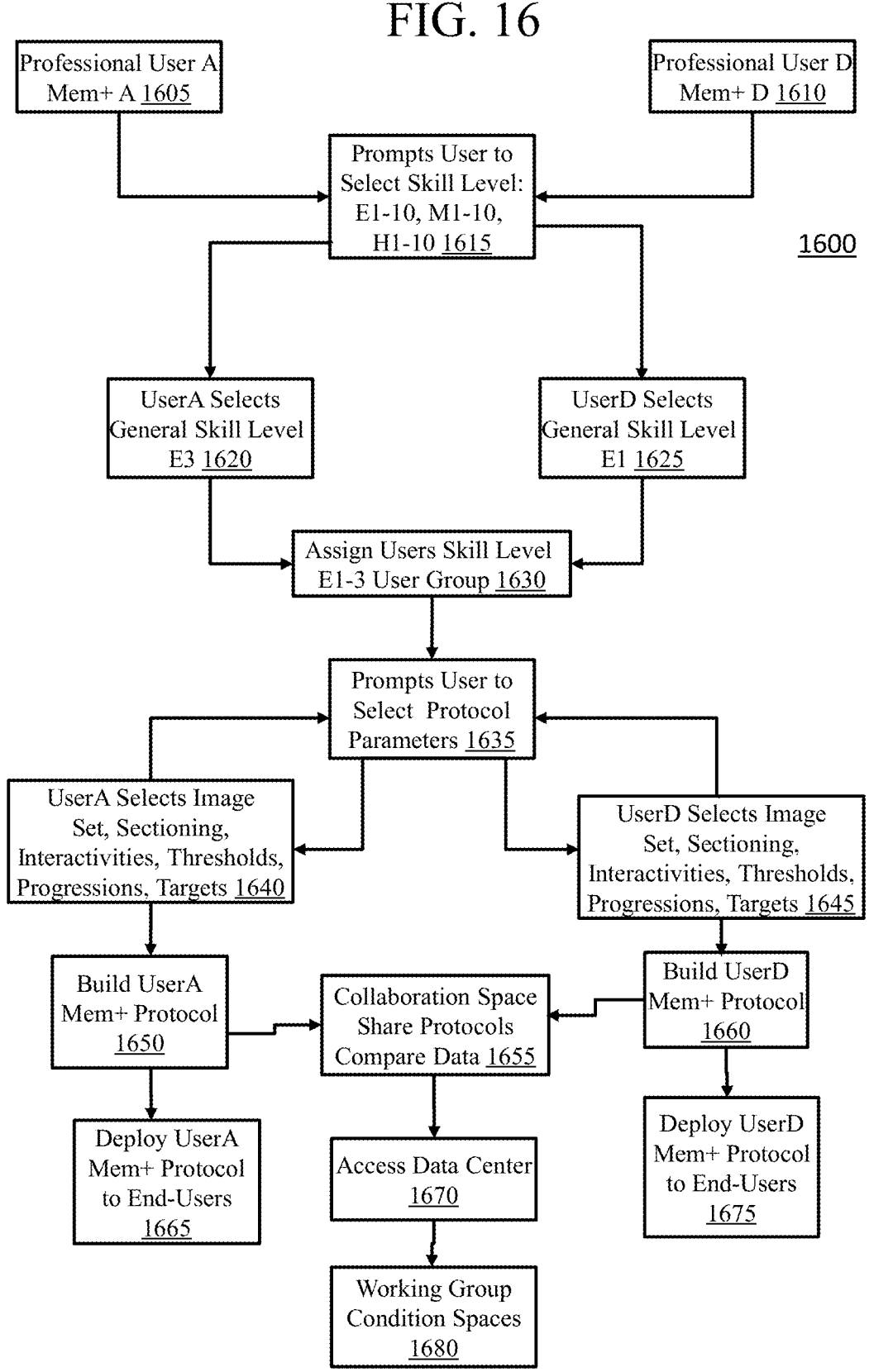
FIG. 16 is a second example of a collaborative method in which professional users (e.g, health-care workers) analyze data from users based on skill levels (see also FIG. 16).

FIG. 16 is a second example of a collaborative method in which professional users (e.g, health care workers) analyze data from users based on skill levels 1600 (see also FIG. 16). In FIG. 16, professional User A and D are collaborating.

In steps 1605 and 1610, Professional User A and D choose a Mem+ (A and D). In step 1615, the system prompts a user to select a skill level.

In steps 1620 and 1625, User A selects general skill level E3, and User D selects general skill level E1.

In step 1630, users that choose skill levels E1-3 are assigned a user group.

In step 1635, the system prompts the User to select protocol parameters, allowing that user to choose how long he or she wants to work on a test or image set with specific contiguity characteristics, how many the user may want to do, etc.

In steps 1640 and 1645, User A and User D selects an image set, sectioning, interactivities, thresholds, progressions, targets, etc. allowing User A and User D to create a personalized Mem+ protocol that is still at skill level 1-3. The images and/or image sets can be presented to the user by the system according to a protocol and/or can be selected by the user.

In step 1650 and 1660, the system builds a Mem+ protocol based on the skill level and selections (in steps 1640 and 1645) for each of User A and User D. Progressions refer to the sequence of interactivities. For example: staying with "Construct" for two images where the user first uses 25% sectioning, then 20%, then 10% is a significant skill level jump, and which lets the user downgrade (or upgrade the skill level) to an in-between point or to a higher skill level (7.5% cuts, 5% cuts) or to 3 images, not just two images. Progressions can also define what comprises an Interactivities Set (Compose 25%; Construct 20%; Construct 10%; Missing Pieces 4×4 grid; MatchME! 25% cuts with half and quarter size pieces).

In step 1655, a collaboration space allows the Professional users A and D (and perhaps other Professional users) to share protocols and compare data for group E1-3. Utilizing a collaborative format and forum, a professional configuration can be shared and re-purposed and/or modified by other Professional users for their applications without having to build a protocol from scratch. The original protocol configuration developed by a Professional user would remain unchanged but where other users are provided with copies of the configuration for their use. The collaboration can be shared protocols for research. Thus, the platform can be a research platform for collaboration and sharing of protocols.

In steps 1665 and 1675 UserA and UserD Mem+ protocols are deployed to the end-users. As determined by the administrator, a professionally developed configuration can be deployed in the consumer end-user space. In some embodiments, this results in an output of assessment data to the collaboration space to build the platform's analytics capabilities with a dynamic source of additional datasets.

In step 1670, the Professional users can access the data center and create working group condition spaces in step 1680. As determined by the administrator, a professionally developed configuration by voluntary agreement can be tested with different user groups in a modified evaluation of the configuration by target audiences. "Condition Spaces" can be defined as areas of collaboration for specific diseases. Specialists tend to think about cognition and the kinds of patients a clinician would be treating in this way by their disease and thus provides a useful, though limited, perspective on disease-based cognitive associations In an embodiment, each of the steps of method 1600 is a distinct step. In another embodiment, although depicted as distinct steps in FIG. 16, step 1605-1680 may not be distinct steps. In other embodiments, method 1600 may not have all of the above steps and/or may have other steps in addition to or instead of those listed above. The steps of method 1600 may be performed in another order. Subsets of the steps listed above as part of method 1600 may be used to form their own method.

Figure 17:
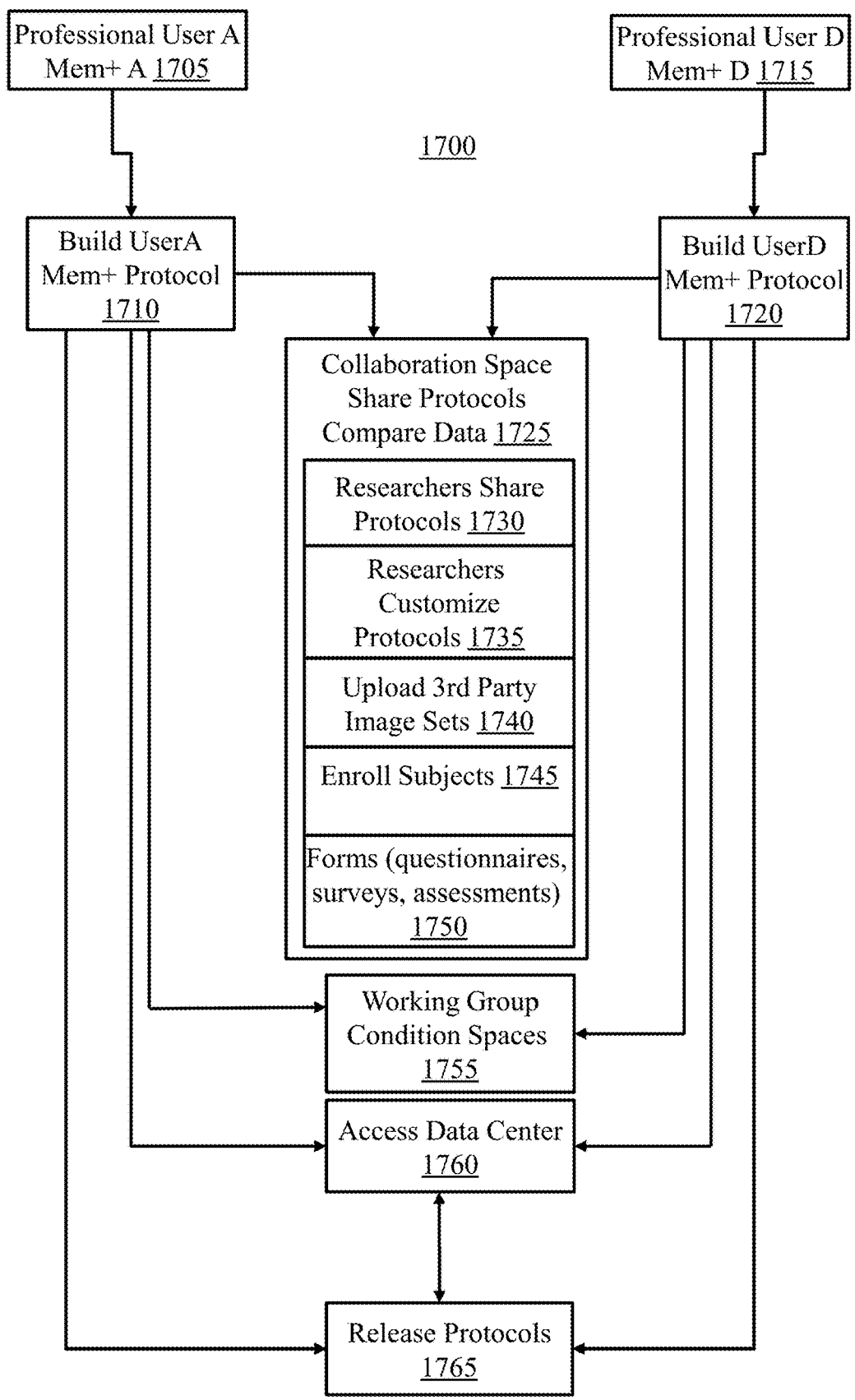
FIG. 17 is an example of a method that allows professional users to create a cognitive platform for specific uses (e.g., tests, diagnoses, treatments of specific diseases) in a collaborative way.

FIG. 17 is an example of a method that allows professional users to create a cognitive platform 1700 for specific uses (e.g, tests, diagnostics, treatments of specific diseases) in a collaborative way. The cognitive platform can be produced using collaborative processes between Professional users.

In FIG. 17, two Professional users (A and D) are collaborating to produce a cognitive platform for a joint study.

In step 1705 and 1715, Professional user A and D each activate a Mem+ protocol.

In step 1710 and 1720, Mem+ protocols are produced for Users A and D.

In step 1725, a collaboration space is produced for sharing protocols and comparing data. Steps 1730 are sub-steps of an embodiment of Step 1725. As discussed in FIG. 16, 1655, in the collaboration space a professional configuration can be shared and re-purposed and/or modified by other Professional users for their applications. The original protocol configuration developed by a user remains unchanged and other users are provided with copies of a configuration for their use. The collaboration can be shared protocols for research. Thus, the platform can be a platform for collaboration and sharing of protocols that are best for a specific patient, group of patients, type of patient, or other user group (see steps 1730-1750): In step 1730, clinicians share protocols. In step 1735, clinicians customize protocols based on the sharing. In step 1740, third party image sets are uploaded. The images and/or image sets may be presented to the user by the system according to a protocol and/or can be selected by the user (e.g., a professional user). In step 1745, subjects are enrolled. The subjects may be anyone that wants be take the customized protocol. In step 1750, forms (questionnaires, surveys and assessments) are prepared, given to subjects and included in the collaboration space. Protocol user statistics and associated data, including questionnaires and assessments are kept separate and in a research safe assigned to each professional developer who is conducting research studies so as to protect participants' identities and other privacy related data and considerations.

In step 1755, working group condition spaces are identified. Working groups may include groups that are appropriate for specific collaborative protocols (e.g., patients with the same diagnosis, patients at the same skill levels, people who want to use the protocols for keeping their cognition healthy, patients who need a customized treatments those enrolled in a specific test protocol, etc.).

In step 1760, a data center is accessed. The data center may contain the information about whether a user can access a specific protocol. In setting up safeguards ensuring only users authorized to access a particular set of data have access may help ensure that a protocol may not be accidentally provided to the wrong user. In this embodiment a user may be a professional collaborator.

In step 1765 final collaborative protocols are released to the collaboration space to be used by the collaborators.

In some embodiments, steps 1725-1750 can be skipped and the Professional Users can immediately include their Mem+ protocols within the working group condition spaces. In some embodiments, steps 1725-1755 can be skipped and the Professional Users can immediately include their Mem+ protocols in the data center (step 1760). In some embodiments, Professional users can immediately include their Mem+ protocols as released products (step 1765).

In an embodiment, each of the steps of method 1700 is a distinct step. In another embodiment, although depicted as distinct steps in FIG. 17, step 1705-1765 may not be distinct steps. In other embodiments, method 1700 may not have all of the above steps and/or may have other steps in addition to or instead of those listed above. The steps of method 1700 may be performed in another order. Subsets of the steps listed above as part of method 1700 may be used to form their own method.

FIG. 18 shows an embodiment of a PICSSi prototype GUI. In some embodiments, the PICSSi platform GUI components can include: a digital application, an expandable image library, categories of interactivities or a pre-defined battery of interactivities (Jumble-Sort, Compose, Missing Pieces, MatchMe!) which may be applied to individual images and to 2-image composites (or multi-image composites) at fixed or variable complexity levels. The percent (%) sectioning strategy (that is the percentage of the total image that each sectioned part is) may be varied, which may affect the number and size of the playing pieces. In an embodiment, a timer can be toggled and hidden. In an embodiment, user gameplay statistics (alpha-type speed and accuracy assessments) may be displayed, and which may include the time taken for each move, the time taken for each group of moves, reaction time (time to first move), average reaction time, and/or the total time taken to complete the interactive, number of errors and which may be stored as part of the user stats and incorporated into built profiles for registered users. A Mem+ protocol may designed to be taken in a unit of 12-sessions, in which the user performs 2 sessions per week with fixed interactivities and image sets, at the easy level, for example.

In another embodiment, the platform may include a Screening/Assessment Tool and/or Therapeutics module, with multiple play options, which may include, but are not limited to, FreePlay: user defined image selections, interactivities, and complexity; and/or Auto-Sequence Play. Auto-Sequence Play may be a set of interactivities based on user progress through a pre-defined sequence of increasing complexity, in which the user completes tasks within countdown clock and proceeds through the pre-set thresholded progressions. The platform may include a Cognitive Health Sequence, which may be similar to sequenced play, but with embedded Mem+ assessment (Remedial, Easy, Medium, Hard levels), with additional scales, and/or to include the use of an optional visible time. The platform may include specialty modules, which may be a subset of interactivities and related assessments which may be deployed (e.g. one of the interactivities may include Stroke Recovery module, which may include an interface and configuration personalized for those who have suffered a stroke, and therefore may include a view-only/auto run, for example) with a progression from VVO to Hands-on modalities as users recover/regain language and/or fine/gross motor abilities.

In some embodiments, there may be alternative presentation modes. In one presentation mode, there may be a user-specific registration and back-end user data stored, Language pack which has an association between words and elements of images, and/or an expanded library which excludes a subset of images based on color, content and/or context. The expanded library may include a number of images that are potentially searchable based on content tags, User-supplied images, semi-automated contiguity analysis, image descriptors tagging, and/or image usage statistics to eliminate potential bias in user selection and overly frequent use of images.

In some embodiments, user statistics may include a movement mapper (that maps movement of the user as the user interacts with the interactivity), saved data linked to the user, a Slide bar to adjust percentage sectioning, Unequal sectioning of the different images (e.g., the size of the section of image 1 may be different than the size of the sections of image 2, which in-turn may be may be different than the size of the sections of Image 3). The presentation may include a tool for converting a 2-image composite image (e.g., which may have strips of two images interleaved with one another) to a 3-image composite image (e.g., by adding a strip of the third image between a strip of image 1 and a strip of image 2). The presentation may include increased size of the composite image as the reference image. The presentation may include an Improved Navigation. The presentation may include an option for fixing or changing the size/change of an image changing the content of an image, a feature for pausing the Game pause, and Piece rotations, among other presentation features.

FIGS. 19A-D shows a table of rules and values that summarize some computations that may be performed to identify and/or characterize contiguities. Referring to FIG. 19D, the prominence and number of contiguities may be represented by a contiguity rating value (CR also referred to as the Ambi Value or juxtaposition value), which may be computed based on the formula, $CR=\Sigma(AF_1+AF_2+AF_3+AF_4+AF_5+AF_6)/n$ (where n=6), where $AF_1$, $AF_2$, $AF_3$, $AF_4$, $AF_5$, $AF_6$ are ambiguity factors (AF). In other embodiments, there may be other factors and/or one or more of $AF_1$, $AF_2$, $AF_3$, $AF_4$, $AF_5$, $AF_6$ may be divided into multiple factors, while one or more others of $AF_1$, $AF_2$, $AF_3$, $AF_4$, $AF_5$, $AF_6$ may be left out thereby changing the value of n.

As indicated in the table, $AF_1$ is a contiguity number, which is determined by detecting edges, using an edge detection technique and/or threshold techniques edge detection technique and/or other types of filters, which produce a binary image based on a threshold that determines which of two values a pixel is assigned.

Contiguity Count Total ($AF_1$) is the average of the count of contiguities based on a variety of methods of counting contiguities. For example, a number of different threshold images may be produced for a variety of intact or different stitched images (which may be stitched differently), where the thresholded values for the image measured at a starting point of 127 value (for example) and then at 160 (for example) for standard images, where the color may be represented by pixels values of 0 to 255, for example, and for each image and stitched image the number of contiguities are counted. The number of contiguities may also be separately computed from the edges generated by an edge detection technique, such as a Sobel. A variety of color map images may be generated for a variety of different stitches, and the contiguities for each image may also be counted.

Then the total number of contiguities counted for each variation of the image and method of counting contiguities are averaged.

More than just two thresholds may be computed. For a thresholded Image at 127 and 160, Averaged Contiguity Count$_{T127}$=(Parts$_{T127b}$+ Parts$_{T127w}$, Averaged Contiguity Count$_{T160}$=(Parts$_{T160b}$+ Parts$_{T160w}$)/2, where Parts$_{T127b}$ and Parts$_{T160b}$ are the number of parts of the image, that after thresholding have an average pixel value of black, and where Parts$_{T127w}$ and Parts$_{T160w}$ are the number of parts of the image that after thresholding have an average pixel value of white, and the subscripts T127 and T160 represent the threshold used for generating the threshold map. Each part may be a continuous region of a set of contiguous pixels of the same pixel value after thresholding. In an embodiment, one may count the number of black and white regions across the width of the image to arrive at the number of parts (e.g., along the central horizontal axis of the image or a long a line that is halfway between the top and the bottom the image). In another embodiment, a vertical disruption larger than a predetermined threshold divides a region into different parts. Additionally, or alternatively, the horizontal disruptions may also divide a region into parts. Additionally, or alternatively, disruptions in other directions may also divide a region into parts. In an embodiment, a disruption is more than 50% of the distance from a first edge to a second edge facing the first edge. For example, a vertical edge that is 50% of the distance from the top edge to the bottom edge of the region divides a region into parts. In other embodiments, the ratio of the length of the disruption to the distance between the opposite facing edges (e.g., between the top and the bottom edge) may be a different percentage, such as 15%, 25%, 75% or 80%.

Contiguity Count Total (AF$_1$)=(Averaged Contiguity Count$_{T127}$+ Averaged Contiguity Count$_{T160}$)/2. AF$_2$ is the color block. Color blocks may be determined based on a sequential color extraction using a reduced, fixed number of colors (e.g., 2-6) from which color images may be based. Color blocks are a kind of contiguity. AF$_2$-CB defines the distribution of color. A color block may extend in any direction. A color block may be formed by a concentration or density of similar colors representing an object or region across a continuum or continuous region in both the horizontal and vertical directions. An example of a color block is the sky. Even in a stitched image, the sky can be blue, albeit of different hues, across the width of an image. The image may be divided into regions (e.g., quadrants and sub-quadrants) and dominant color or colors are determined for each region. Color blocking allows for the identification and analysis of the colors in an image. Color blocking allows for an analysis of the colors in an image, the distribution of the color, and the identification of breaks in the block may be determined, indicating the presence of one or more vertical disruptors or other objects. The interruptions in color confluency can disrupt the color block's saliency and/or facilitate identifying what the color block is. In this process, the image is progressively reduced to a smaller number of colors (e.g., less than 8, less than 7, less than 6, less than 5, less than 4, less than 3) During color reduction, the pixels may grouped into bins of a histogram according to which color bin color value of the pixel is closest (e.g., if the image is reduced to the colors having color pixel values 100 and 200, then a pixel with a color value of 75 would be place in the bin for the color 100). A color extraction is performed on each color-reduced image to determine the number of pixels in each color bin. The values are averaged to arrive at the AF$_2$. Up to 6 color blocks can be identified and used for the calculation, depending on the number of colors and their percentage of contribution to the image.

For example, for a 3-color reduction the formula for the AF$_2$ is CB.c$_{\bar{x}}$(AF$_2$)=(CB.c2+CB.c3)/3. More generally, the formula for AF$_2$ is CB.c$_{\bar{x}}$(AF$_2$)=(CB.c2+CB.c3+ . . . CB.c(n))/n (where n is the number of colors which are in the image, and which is an integer number having a value selected form the numbers 2-6). In the above formula CB.c2 is the number of regions of contiguous pixels of one color identified after a reduction to two colors. CB.c3 is number of regions of contiguous pixels of the same color identified after a reduction to three colors, and CB.c(n) is the number of regions of contiguous pixels of the same color identified after a reduction to n colors.

AF$_3$, is contiguity linearity (C$_{linearity}$) for a contiguity using a stitched image. AF$_3$ may be computed from C$_{linearity}$=C$_A$+C$_D$, where C$_A$ is a value that represents an average of the degree to which the angle of the contiguity changes (e.g., the angularity) across the contiguity, and C$_D$ is average the number of breaks in the contiguity. C$_D$ also represents a value that reflects how disrupted the contiguity is, as measured using the stitched image. For example, in an embodiment, C$_D$ may have one of two values, which are 0 and −0.25, where C$_D$ is assigned the value of zero if the contiguity spans more than 75% of the width, and C$_D$ is assigned a value of −0.25 if the contiguity spans less than 75% of the width.

The contiguity angle may be computed from C$_A$= (L2C$_{\bar{x}}$+R2C$_{\bar{x}}$)/2, where L2C is the angle made by a line connecting the center of the contiguity to the point where the contiguity intersects the left side of the image, and R2C is the angle made by a line connecting the center of the contiguity to the point where the contiguity intersects the right side of the image R2C is the line that best approximates the angle made by the right side of the contiguity whether or not the contiguity intersects the right side of the image. L2C is the line that best approximates the angle made by the left side of the contiguity whether or not the contiguity intersects the left side of the image.

Some rules for determining linearity according to at least one embodiment are as follows. The values in this discussion are based on the angle of the dominant contiguity and, the distance off of the X-axis. The measured angles are computed and averaged. The measured angles are further distilled with rules, so that images which differ significantly in terms of content can be still be grouped and categorized according to their angular complexity. However, having the angularity data for each stitch and peel image additionally allows for the extraction of other information.

A value of 0 is assigned if the contiguity disruption is a straight edge, extending across more than 75% of the image width and if the averaged angular difference of a single baseline point is less than 5°.

A value of 0.15 is assigned to the linearity if the average angular difference is between 5° to 30°. A value of 0.25 is assigned to the linearity if the average angle difference is between 30° to 45°. A value of 0.75 is assigned to the linearity if the average angle difference is greater than 45° and if the contiguity extends across the image as a diagonal. A value of −0.15 is assigned to the contiguity if the contiguity is disrupted and/or non-linear (or irregular). A value of −1.0 is assigned to images without a defined contiguity or without an object-based contiguity. For example, if the only contiguity is the sky, that contiguity has a linearity of −1.0.

In this embodiment, a solid block of color is not viewed as a horizon contiguity with linearity. If there is a horizon type of contiguity, the value of the horizon contiguity is different than −1, but in this embodiment, as a color block the sky has no linearity, per se, as defined by angles or disruptions since there are no disruptions in the sky's continuity.

In an alternative embodiment, the absolute value of the sine of the average angle (or the square of the sine of the average angle) may be used for linearity for contiguities with no disruptions.

Referring to FIG. 19A, $AF_4$ is a continuity value ($C_{continuity}$) for a contiguity using a stitched image. $AF_4$ is computed from $C_{continuity}=C_{VD}+C_{IE}$, where $C_{VD}$ is a value representing the average of the span (e.g., average of the total width of all) of the vertical disruptors per contiguity, and Cm is an average of the span of irregular edges of a contiguity. Some examples of VDs are a tree, a grove of trees, or a house on an otherwise continuous contiguity. Each VD has a height and can extend from the contiguity to the top edge of the image or to points in between. The irregular edges (IE) refer to what can be likened to an uneven surface—a rocky shoreline, or a city landscape which forms an irregularly edged (uneven, bumpy) contiguity by virtue of the color block of sky above and the continuity of the buildings across some or all the horizon.

The Continuity Rules for assigning values to images with Vertical Disruptors and/or Irregular Edges are summarized in FIG. 19A. The Continuity Rules are: if an image has at least one contiguity which is continuous across the entire width of the image (75-100%+/−3%), then assign a value of 1.0. If the contiguity is continuous across 50-75%+/−3% of the image, then 0; if less than 50% or if contiguity number is 0, then assign a value of −1.0. If there is/are a vertical disruptor extending more than 5% but less than 30%, individually or if combined, up from an otherwise linear and continuous contiguity but which has additional complex contiguities, then assign a value of 0.5. If there are 2-3 VD but which are spatially separated, then assign a value of 0.5. If the vertical disruptors individually extend in the vertical direction less than 20% of the distance to the top of the image from an otherwise linear contiguity then the VD is assigned a value of 0.5.

If there are multiple vertical distractors present in the image (trees in the foreground), then assign a value of −1.0. Optionally one can use progressive decrements to identify variations/objects off the X-axis and their return to an established baseline across the entire image. If there are multiple irregular edges on one or more contiguities or if there is a single contiguity without a color block greater than 30% of the image's height above the IE, then assign a value of −0.25. Assign a value of −0.15 for a single contiguity with a poorly defined edge which may be interrupted across the width of the image, be irregular, or have vertical disruptions, but which is adjacent to at least one continuous color block or a color block greater than 30%.

For Irregular Edges, a poorly defined edge is a contiguity which is irregular, and/or which has multiple vertical disruptions throughout its width and/or clustered in regions. From a quantitative standpoint a poorly defined edge would be an edge having multiple Vertical Disruptors present along the entire length of the contiguity, disrupting the horizon interface and/or where less than 30% of the contiguity's interface has a discernible color block above the disrupted portion of the contiguity. The percentage of disruption may also be defined by a series of grid tools to evaluate how much space a VD occupies and the color block above and around it.

The $C_{VD}$ is computed using the above contiguity rules (FIGS. 19A and 19B).

Note that the formula below is used to determine where a VD meets the criteria for the rules. The formula accounts for multiple vertical disruptions. For example, for a farmhouse on the prairie with a silo, windmill, barn and house in otherwise open space, each of the elements would represent a VD which would be analyzed according to each VD's contribution to the overall VD impact to disrupting the contiguity's continuity, because the individual VDs are considered to define the VD relative to one another (the space between VDs from a width perspective, and the height parameter for the image as defined by the contiguity's Y-location).

To compute the $C_{VD}$, the Sub-area$_{dc}$ is the area above the dominant contiguity. The distance between vertical distractors is measured. The ratio of the area of the first vertical distractor to the subarea (e.g. quadrant) in which the first vertical distractor is in is computed according to the formula:

$$C_{VD.a1}=\text{Vertical Distractor area1}=(VD1_{Q1w})(VD1_{Q1h})/\text{Sub-area}_{dc}$$

$VDmQ_{nw}$ is the width of vertical disruptor m of quadrant n and $VDmQ_{nh}$ is the height of the vertical distractor m of quadrant n. For example, $VD1_{Q1w}$ is the width of vertical disruptors of quadrant 1 and $VD1_{Q1h}$ is the height of the vertical distractors of quadrant 1. the subarea is the area above the contiguity, and each $C_{VD}$ is the percentage of the area above the contiguity that is occupied by the vertical distractor. The above continuity rules are applied to the first vertical distractor based on the area $C_{VD.a1}$.

The ratio of the area of the second vertical distractor to the subarea (e.g. quadrant) in which the second vertical distractor is in is computed according to the formula $$C_{VD.a2}=\text{Vertical Distractor area 2}=(VD2_{Q2w})(VD2_{Q2h})/\text{Sub-area}_{dc}$$

The continuity rules of FIGS. 19A-D, are applied to the first vertical distractor and to the ratio of the area of the second vertical distractor to the subarea containing the second vertical distractor, $C_{VD.a2}$. The process applied to VD1 and VD2 is repeated for each vertical distractor $C_{VD}$. In an embodiment, for Irregular Edges, there is only one definition for a vertical disruptor, which is based on the width of the irregularity. (All VD are irregular, but not all irregularities are VDs. For example, the trees of a grove of trees VDs are; the grass or flowers of a field with flowers or grass form an IE or part of an IE).

$C_{IE}$ describes irregular edges as part of computing the contiguity's continuity according to the following rule: If there are multiple irregular edges present on one or more contiguities; or, if a single contiguity is present but without a vertically adjacent color block with an area greater than 30% of the image above the contiguity, then assign a value of −0.25. Assign a value of −0.15 if there is only a single contiguity with a poorly defined edge, but which is adjacent to at least one continuous color block, or has a vertically adjacent color block with an area greater than 30% of the image, above the contiguity.

Referring to FIG. 19D, $AF_5$, is the color block depth 100, which defines the color block distribution (see step 524, above). The assignment of a value follows a set of rules described in FIG. 19B using a quadrant-based analysis of the color distribution in the image. The FIG. 19B rules table applies to both $AF_5$—Color Block Depth 100 ($CBD_{100}$) and $CBD_{ST}$, for the stitched image.

Referring to FIG. 19D, $AF_6$ is the spatial color-contiguity, which compares the contiguity number to the color block number. To obtain a value for $AF_6$, compare the value obtained for $AF_2$ (Color Block) to $AF_1$ (# of contiguities present in the image), and are summarized in the table in FIG. 19C as follows: If AF1 is equal to AF2, then assign a value of 0; if AF1 is greater than AF2, then assign a value of 1; if AF1 is less than AF2, unless the contiguity number is equal to 0, then assign a value of 2; and, if AF1=0 then assign a value of −1.

Figures 20A, 20B:
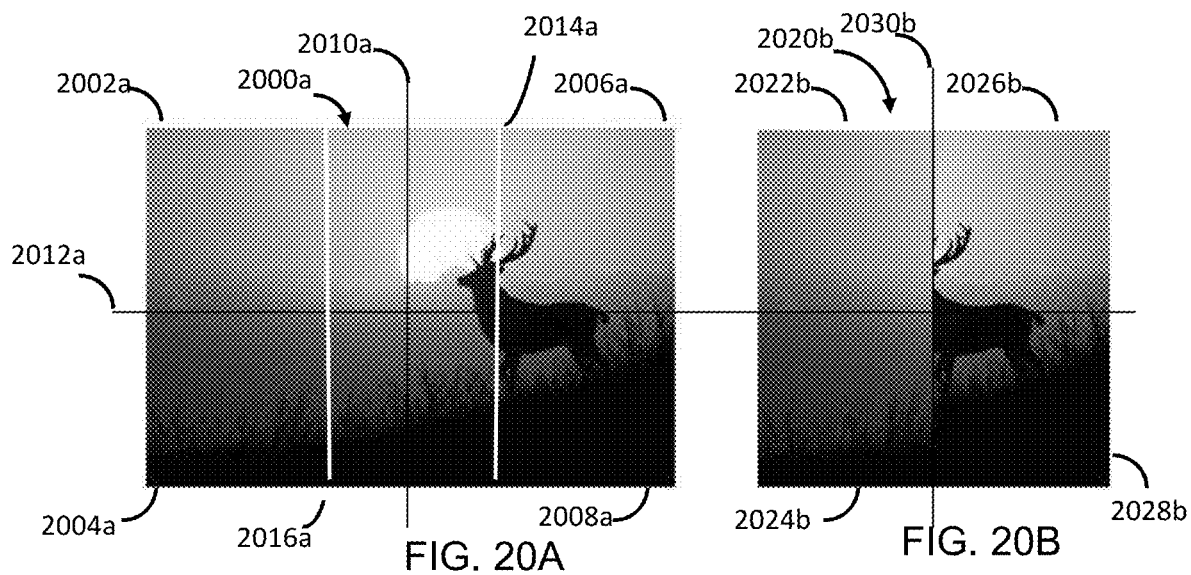
FIGS. 20A and B show an example of the application of quadrant-based measures, a stitch-based angle determination for analysis of an image.

FIGS. 20A and 20B show the application of a stitch and peel, according to at least one embodiment. FIGS. 20A and 20B show two versions of an image of a buck, which includes image 2000a which is the full image prior to being, and image 2020b which is the same image as image 2000a after being stitched.

In at least one embodiment, image 2000a (FIG. 20A) are divided into predefined sections, e.g., a first section, a second section, and a third section. For example, white lines 2014a and 2016a divide image 2000a into three horizontal strips, each horizontal strip is about ⅓ of the full image.

In FIG. 20B, the first section can be shifted from being adjacent to a second area to being adjacent to be a third area, so that the first section can mask the second section, thereby removing the second section (which in one embodiment may be ⅓ or 33% of the image) from the resulting image, which is image 2020b shown in FIG. 20B, so that in FIG. 20B, line 2030b is in the location where line 2014a has been moved to in the process of removing the middle section of image 2000a. The locations of line 2030b is also the location were line 2016a was located in FIG. 20A, So that in image 2020b, lines 2014a, 2016a and 2030b are all in the same location as a result of removing the middle section of image 2000. The first section can be peeled at another predetermined value, for example, at twenty percent, as represented by image 2020b (FIG. 20B) in which the central 25% of the image is removed); alternatively other amounts (e.g., 6.26%, of the total image, 12.5%, of the total image, 18.75% of the total image, etc.). Different aspects of the contiguities and the images, as a whole are emphasized, and by averaging the characteristics of the different stitched versions of the same image of the images 2020a and 2020b features that may be missed by looking at the image as a whole may be found or by looking at any one given stitch. In other embodiments the stitching and peeling may be done in a different way than what is depicted in FIGS. 20A and 20B). For example, a different percentage of the image may be removed (e.g., 90%, 80%, 60%, 40%, or 20% may initially be removed), and different percentages may be put back (e.g., the put back parts in each stitch may be 10% of the amount removed, 15% of the amount removed, 20% of the amount removed, 25% of the amount removed 33% of the amount removed, or 50%). The amount put back at each stitch and peel may be different. For example, in the first stitch 15% of the amount removed may be returned, and in the second stitch 55% of the amount removed may be returned, and as a result of the first and second stitch is to return a total of 15%+ 55%=70% to focus on different aspects of interest.

FIGS. 20A-F also shows the application of a stitching analysis with quadrant-based color blocking, according to at least one embodiment. Image 2020 (FIG. 20B) shows stitch of a first image 2000 (FIG. 20A), according to at least one embodiment. The first image 2000 (FIG. 20A) is divided into four quadrants, e.g. first quadrant 2002, second quadrant 2006, third quadrant 2004 and fourth quadrant 2008. The four quadrants are defined by horizontal line 2012 and vertical line 2010 (FIG. 20A).

In stitched image 2020 (FIG. 20B) the quadrants overlap to produce first stitch quadrant 2022, second stitch quadrant 2026, third stitch quadrant 2024 and fourth stitch quadrant 2028. The stitched image 2020 can enable determining that the color blocks between the quadrants, and in which of the quadrants are different and asymmetrical. By bringing together two areas of the image that are not actually juxtaposed, machine system 101 can more easily provide an indication of a disruption in the color block or the presence of an object (e.g., a vertical distractor) in the image. In FIG. 2020, the stitched image of FIG. 2000, the vertical axis 2010 is replaced with vertical axis 2030b, while the horizontal axis 2012 is the same.

In FIGS. 20A and 20b, the disruption at the seam may be less than the disruption of the foreground, which facilitates automatically identifying a contiguity (similar to the way the mind is able to piece together the horizon and distinguish the background from the foreground).

Figures 21A, 21B, 21C:
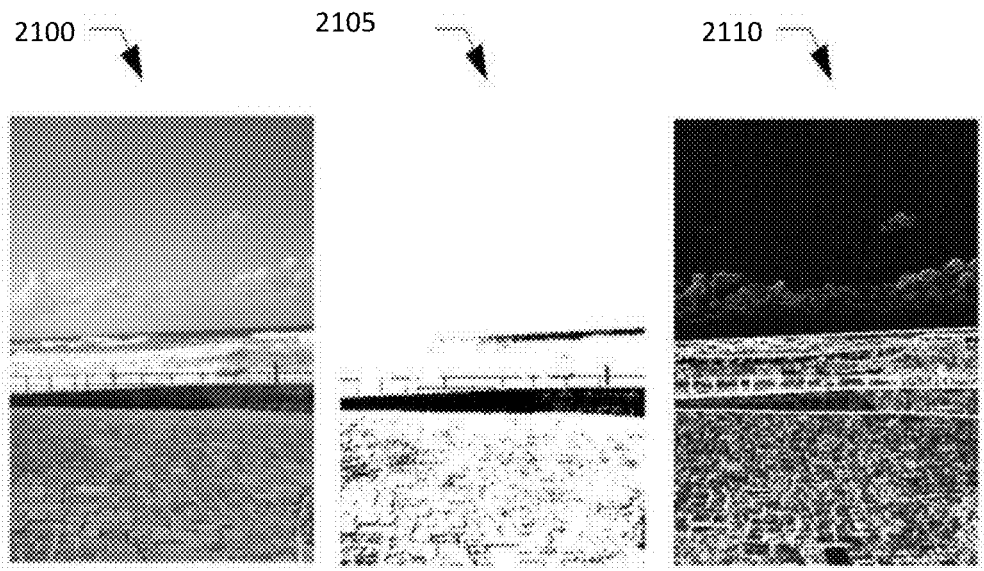
FIGS. 21A-C show an example of the application of the use of color thresholds to extract contiguities for image analysis.

FIGS. 21A-C shows an example of the application of the use of color thresholds to extract contiguities characteristics data for image analysis. In FIG. 21A, the first photograph 2100 (of the photographs of FIGS. 21A-C) shows a full color photograph of a beach scene with a fence. This photograph of image 2100 shows a number of contiguities, including the fence, the water/sky interface, and the fence cobblestone interface. The second photograph 2105 shows a version of 2100 having colors at the blue end of the spectrum removed, which brings out the fence contiguity and the fence cobblestone interface, but shortens the ocean water contiguity. The photograph 2110 shows a view of the photograph 2100 that has colors at the red end of the spectrum removed and creates some stronger contiguities (e.g., the clouds can be argued to become a contiguity), but makes some of the others less distinct (e.g, the fence, water/sky interface and cobblestone/fence interface become less distinct from each other. However, the pattern of the cobblestones becomes more distinct, without providing new contiguities.

Figure 22A:
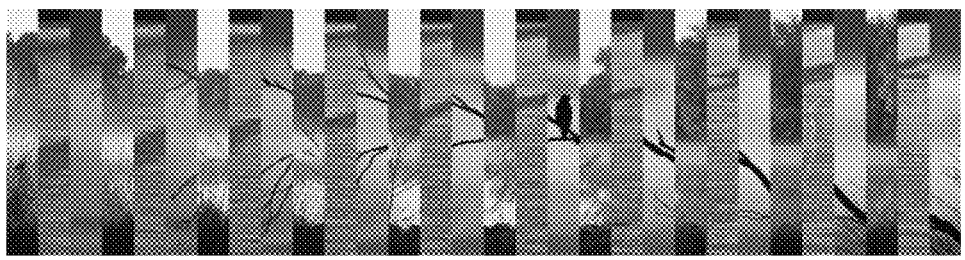
FIGS. 22A-D show an example of composite images, including multi-stable (22A and 22B) and stable figure-ground relationships (22C and 22D).
Figure 22B:
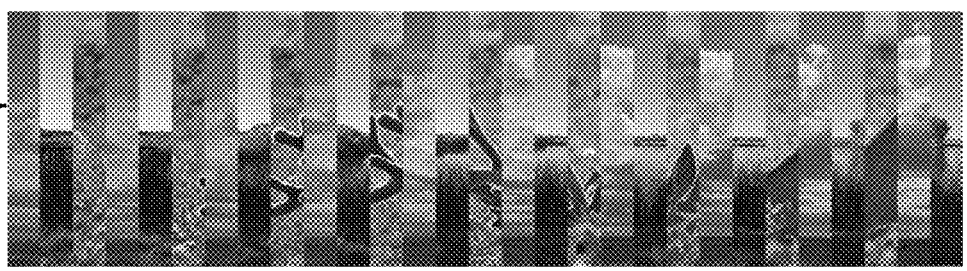
Figure 22C:
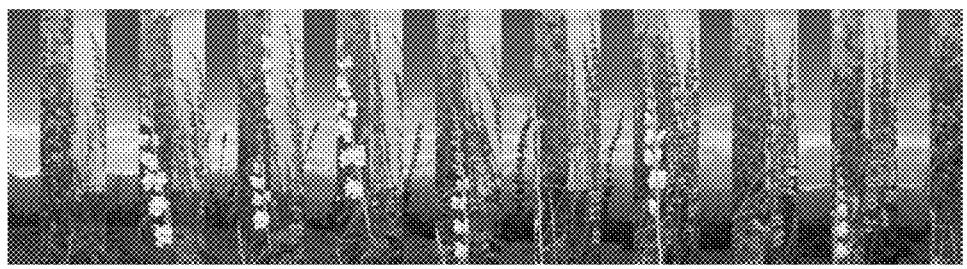
Figure 22D:
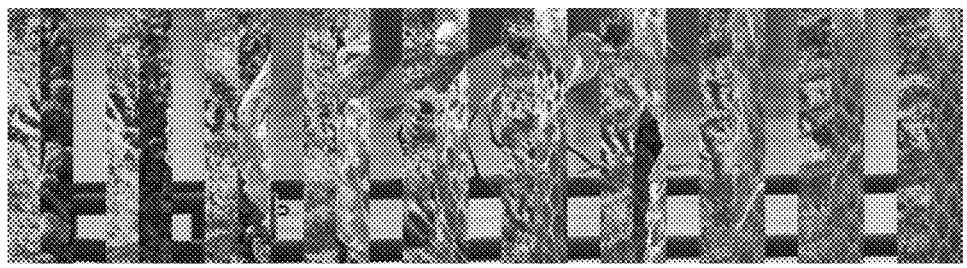

FIGS. 22A-D shows an example of composite images comprised of three images and how the presence of contiguities in one or more of the images affect the stability of the image in the ground position at any point in time. FIGS. 22A and 22B are multi-stable image sets. FIGS. 22C and 22D are stable or fixed, i.e. the image in the ground position remains in the position. FIGS. 22A-D provide an example of how image sets in a composite image may embed multiple Gestalt principles such as figure-ground, completion, and continuation which engage top-down cognition and bottom-up sensory processing as the user virtually reassembles the spatially separated image parts into the original image from which the image parts came from.

FIG. 22A shows a composite image with a bird on a tree limb as one image, a frozen lake with a crack in the ice and shadow extending across the surface as another, and a foggy lake scene with surrounding trees against the sky as the third. The full composite image of the bird on a branch when used as one component image of a 3-image composite, showing how the contiguity "strength" and sectioning strategy can affect which of the three images is pushed to the ground position. Since all three images each have contiguities depending on where the user is looking, that image will be perceived as occupying the ground position. The sectioning aspect is not trivial and in many ways counterintuitive. The greater the number of the sections (up to a point), the smaller the intervening sections which serve as disruptors and the greater the confluent capacity of the ground image, i.e. the easier it will be for the mind to reassemble the ground image.

In FIG. 22A, the tree limb in the first image, the shadow on the snow in the second image, and the interface between the water and the sky, combined with the sky and water color block size and coherency in the third image, are each reasonably distinct contiguities although each varies in width. Consequently, FIG. 22A is multi-stable, because each of the images has a contiguity extending across the image. A composite comprised of two images, each having contiguities would commonly be referred to as bi-stable.

FIG. 22B shows the top of a deer with antlers, a lake scene and a field with a cloudy sky. In FIG. 22B, the antlers and the top of the body of the deer form an object-type contiguity comprised of a single object against a relatively uniform color block (the field), the interface between the ground and the sky (which is in the middle of the image), and the interfaces between shoreline, lake and sky, and the field and the cloudy sky, each forming contiguities, which make the image multi-stable. One noteworthy aspect of the composite image of FIG. 22B is that to the middle to upper right of the composite image, the blue water in the lake and sky interface are dominant, but which become less salient on the left portion of the composite. Towards the middle left, however, the deer's antlers framed against the meadow allow that portion of the image to assume the ground position; and the field-cloudy sky image can become the ground image when the bottom 10-20% of the image becomes the focal point of the user's attention, interest or focus.

Thus, ground positioning is dynamic based on contiguity dominance. In FIGS. 22A-B, the image set has three contiguities of different weights/saliency which are spatially separated—giving it switch characteristics as a multi-stable image set. This happens because the mind predicts what comes next, infers based on information it has, color, content, context which is why the Gestalt principles of continuation, completion and closure work to fill in the gaps, or in this case to follow the visual cues, ignoring the distractions (gaps or blank spaces). Contiguities may also be formed by large regions of the same or similar texture and/or coloring (e.g., the sky, a body of water, field behind the deer).

FIG. 22C shows two different floral scenes, one against a sky and the other without a clear distinction, and an image of mountains against a strong sky background. Only the image of the mountains against the clear sky has distinct contiguities, and so the image is stable and the image in the ground position fixed, i.e. not multi-stable.

Similarly, FIG. 22D shows a snakeskin, raccoon tracks in the sand, and a bird walking along a railing against water. Only the image of the bird on the railing has distinct contiguities, and so FIG. 22D is stable and the image in the ground position fixed, i.e. not multi-stable. The virtual reassembly of the image in the ground is a facilitated process. Maintaining ground positioning for one of the images in a multi-stable image set has a higher cognitive load in removing the distracting flanking content and to prevent a switch if that is a desired attention training protocol. For FIGS. 22C and 22D, constructing the images in figure position may require a higher degree of cognition, since only one of the three images has a contiguity uniting the components of that image. The additional difference between FIGS. 22C and 22D is the ease of identifying what the figure images are; in FIG. 22C floral content is clearly discernible and recognizable, whereas in FIG. 22D, the snakeskin and raccoon have a more abstract quality making their identification more difficult and the image set more ambiguous. Both are still stable, but their complexity differs and as such the interactivity skill levels using the image sets differ.

FIGS. 23A-F show examples of two-image composite images in which contiguities are removed from one of the images to change the characteristics of the composite image. The component image content is the same as FIG. 23A, a 3-image composite. In FIGS. 23A-F, the sequential removal of contiguities transforms a Multi-stable image set into a Stable image set. FIGS. 23A and 23F are the same.

Figure 24A:
FIGS. 24A-C show examples of two-image composite images that show hierarchical relationships in the figure-ground positioning.
Figure 24B:
Figure 24C:
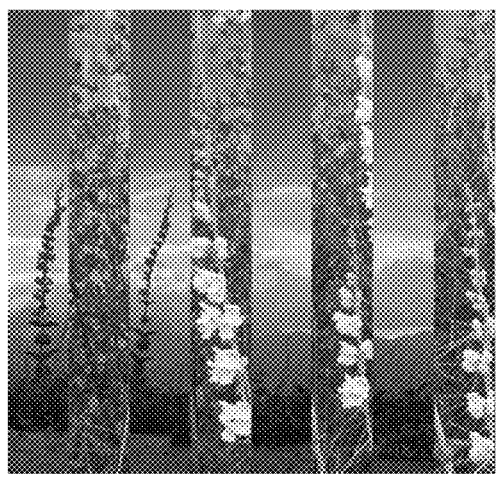
Figure 25:
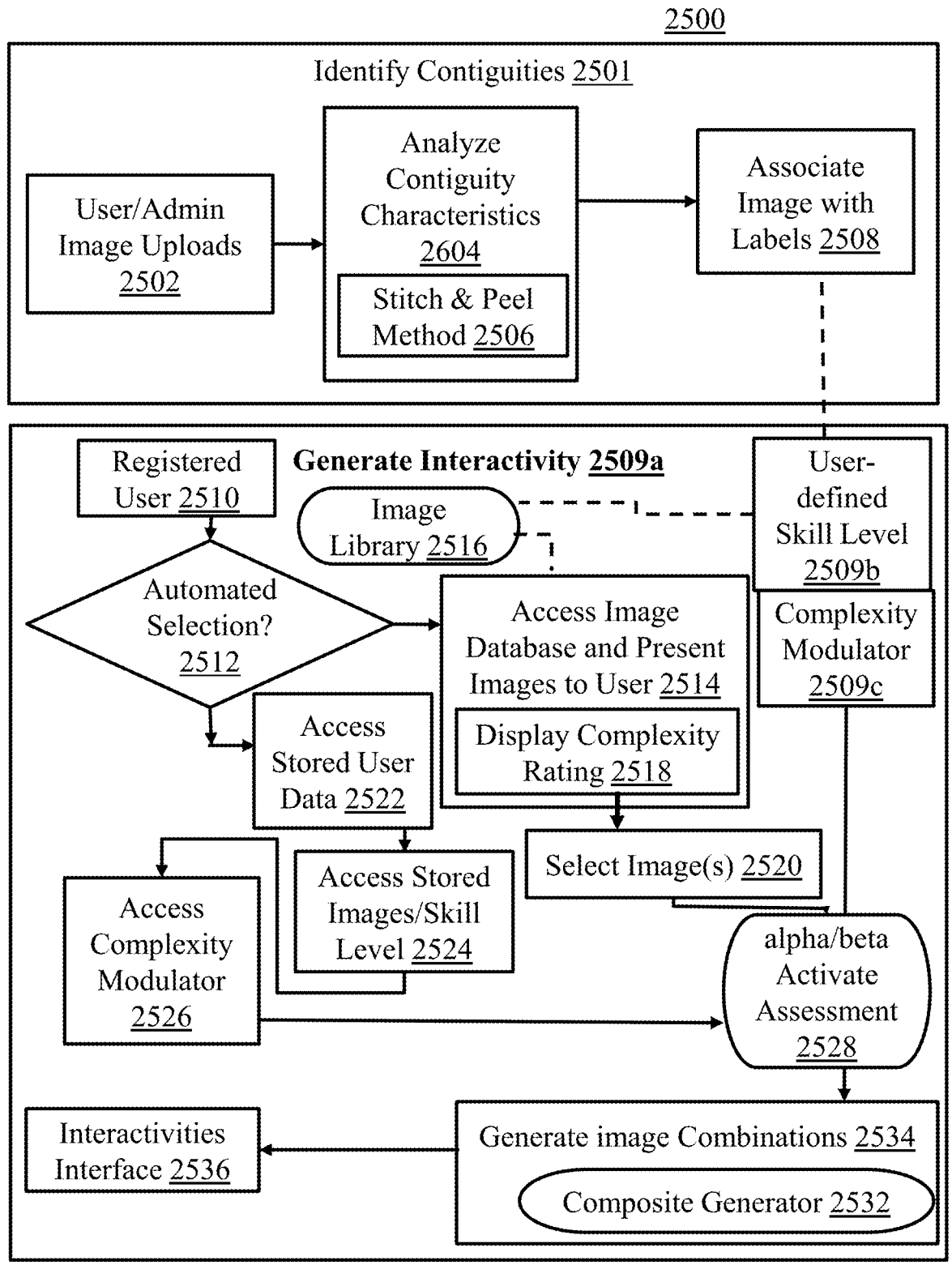
FIG. 25 is a flowchart showing an embodiment of a portion of cognitive interactivity platform for creating an interactivity.

FIGS. 24A-C show examples of two-image composite images that show hierarchical relationships of contiguities based on image combinations in figure-ground positioning. In particular, in FIG. 24A, the image in the ground position has essentially one contiguity, while the image in the figure position does not have a discernible contiguity (i.e., the sky is not visible). In FIG. 24B, the figure in the ground position has a multiple contiguities, whereas the image in the figure position has large vertical disruptors (flowers) disrupting the interface between sky and ground. In FIG. 24C, the same image is in the ground position, but the image in the figure positions does not show any sky. Thus, although each of FIGS. 24A-C are stable image sets, the stability of the image in the ground position in FIG. 24B and FIG. 24C is greater than the stability of the image in the ground position in FIG. 24A, but which is higher than the image in the figure position of FIGS. 24A and 24C. These differences allow complex, content-rich image sets to be categorized and ranked as part of the cognitive platform. These differences can be used to convey images sets of varying complexity, with different characteristics and which can be integrated into interactivities-embedded assessments and training protocols. These differences require different cognitive demand in discerning differences, identifying component parts, and resolving ambiguities which can be exploited in the platform.

Figure 26:
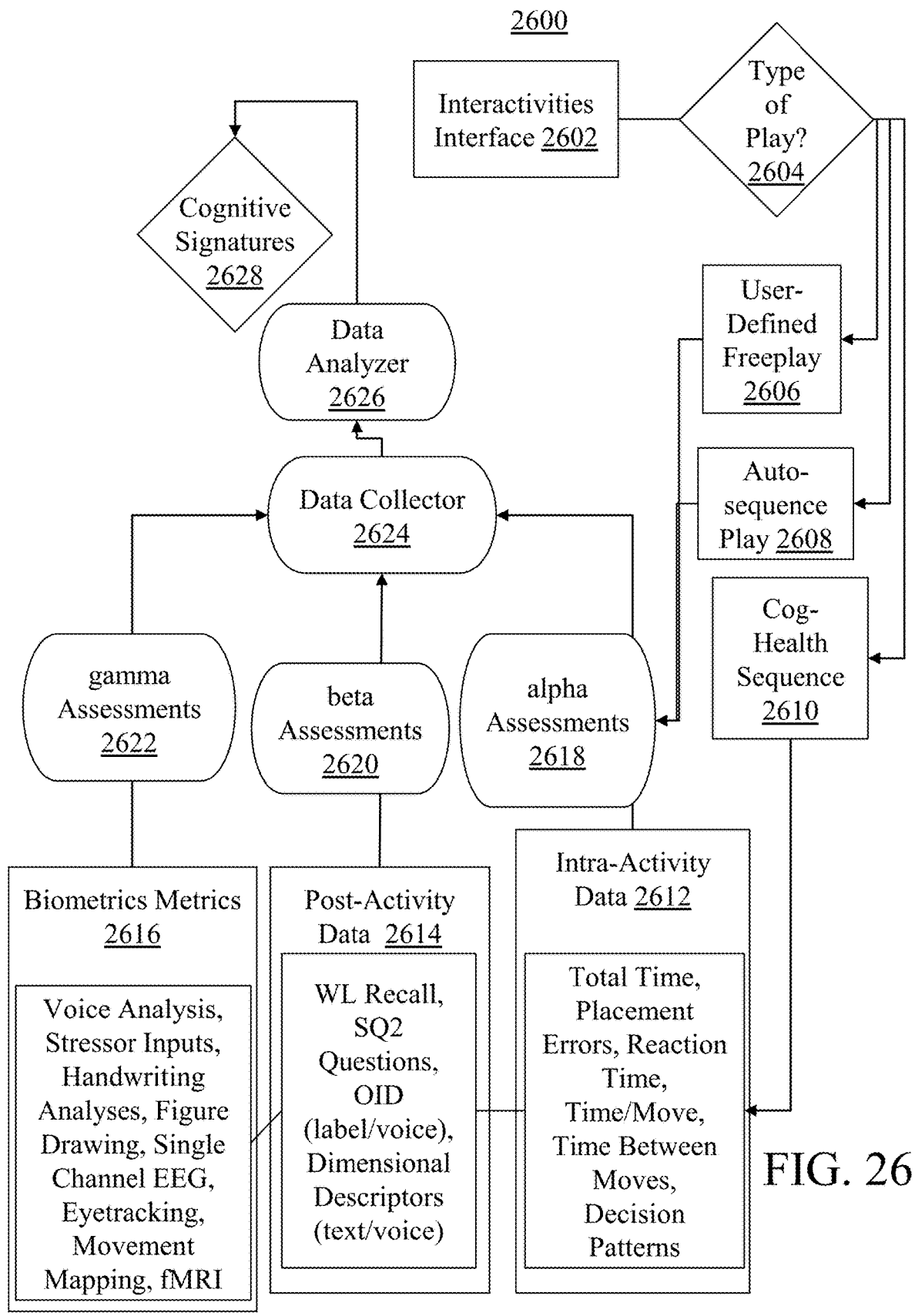
FIG. 26 shows a flowchart of a method of interacting with an interactivity.

FIG. 26 is a flowchart showing an embodiment of the cognitive platform 2600. A user can use the platform 2600 to treat, diagnose and/or train cognitive processes across multiple cognitive domains. Method 2600 starts with step 2601, in which the characteristics of the images used are analyzed. Step 2601 does not need to be repeated each time the user wants to interact with an interactivity, but may need to be repeated every time a user (e.g., a clinician, someone who desires to improve their cognitive abilities, and/or a patient) would like to add an image to the. Platform 2600 includes a system and method for identifying contiguity characteristics in an image and a Mem+ Assessment tool. A user may interact with Platform 2600 online via a GUI or the Standard Mem+ Assessment auto-launch and which can also be run offline with modifications to trap speed and accuracy data, or utilizing the TUI hybrid model—a tactile prop with digital captures.

Step 2601 includes steps 2602-2608. In step 2602, the user/administrator (whom may be a clinician or non-clinician) uploads one or more images.

Step 2600, step 2610a has two entry points. The flowchart shows two entry points one defined by the user (2610b) and potential override or merge by an administrator (2602) and the steps of the flowchart that come after the two entry points from two paths that flow into the same point.

Thus, the process can start at step 2602 when the user/administrator uploads one or more images. Alternatively, the process can start when a registered user begins to use the cognitive platform by logging in 2610 (see FIG. 9 user login).

After the user/administrator uploads one or more images in step 2602, then in step 2604, the platform analyzes contiguity characteristics of the unaltered image. As part of step 2604, the image characteristics are identified and/or quantified. Step 2604 may include determining the number of contiguities, the contiguity rating, regularity, the number of vertical disruptors, the linearity, span, distribution, and/or color block depth, for example. Step 2604 may include determining content of images, which may be added to content tags. Step 2604 may include substep of 2606. In step 2606, the image is stitched and peeled to determine the image characteristics.

In step 2608, the images are associated with descriptive information. For example, content tags (indication of the content of the image), complexity ratings, aesthetic value, contiguity, and/or switch capacity (which may have been determined in step 2604 and 2606) may be associated with the image. After step 2608, the method proceeds to step 2609*a*. Alternatively, if the images have already been analyzed and associated with labels, the user may start with step 2609*a*, In step 2609*a*, the user interacts with one or more interactivities, during which the user's activities may be monitored and analyzed, so that the interactivities presented to the user may be adjusted according to the user's needs and skill level, for example. Step 2609*a* includes steps 2609*b*-2636.

Step 2609*a* has two entry points, which are steps 2609*b* and 2610. Step 2609*b* follows after step 2608. In other words, if the step 2601 was implemented, the next step may be step 2609*b*. In step 2609*b*, the user may define what the user believes is their skill level. In step 2609*c*, based on the user's input about their skill level, the criteria are determined for selecting parameters of images for interactivities and/or interactivities. When the user enters step 2609*a*, via step 2609*b*, an administrator may be logged into the plat form by an administrator and/or may the user set up their own account. Alternatively to step 2609*b*, the user may enter step 2609*a* at step 2610, and at step 2610, the user logs into the platform.

In step 2610 (which is the second entry point to the platform), a registered user begins the cognitive platform. After step 2610, in step 2612 a determination is made whether the user would like to manually select images for the interactivities or whether the user would like the platform to automatically select the images according to the user's needs as indicated by past assessments, user category norms and predictive analytics, and/or clinician input.

If it is determined that the user wants to select images, the method proceeds to step 2614. In step 2614, the image database may be accessed, and images available to the user are presented. In one embodiment, all the images of the database may be available to the user. In another embodiment, only images selected by a clinician for the user and/or previously selected by the user as images that the user wants to be able to select from.

Database 2616 is the database of images available to the user, which may be accessed during steps 2609*b* and/or 2614.

Step 2618 may be part of step 2616. In step 2618, the complexity of the images may be displayed to inform the user regarding which images they may wish to select.

In step 2620, the user selects one or more images for one or more interactivities. As part of step 2620, the user may determine whether the user would like an interactivity with a single intact image or an interactivity that involves a composite of multiple images. If the user decides they want an interactivity that is composite of multiple images, the user decides how many images will make up the composite and then selects that number of images.

Returning to step 2612, if the user decided to have the images automatically selected by the system, then the method proceeds from step 2612 to step 2622. In step 2622 the system access the user's data if they are returning user or relevant information is contained in their profile developed at registration. In step 2624, the user's stored skill level and the image database is accessed. Then in step 2626, the method activates a complexity modulator, which establishes criteria for selecting an image and set of interactivities based on the skill level and/or cognitive ability of the user.

After steps 2609*c*, 2620, or 2624 (or any time beforehand) the activity assessment 2628 is activated, so as to include the user interactivity with the platform prior to actually interacting with the interactivities. The assessment may begin at any point prior to the start of the first interactivity, the Mem+ assessment includes a questionnaire of the user's habits and general health, as well as any recent changes to their health. In an embodiment, a full questionnaire is only used at registration, while a shorter questionnaire is used prior to the start of an assessment-linked session. Questions may include, for example, "did you sleep well?" "Have you eaten?" "Have there been any changes in your medication or health since the last time you answered these questions?" "How would you rate your alertness/attention on a scale of 1-5?" "Are you wearing your glasses?" For example, assessment 2628 may be activated as soon as the user logs in, sets up an account, and/or is logged in by a clinician.

After assessment 2628 is activated, in step 2630, an image set is selected (e.g., based on the user's skill level as determined in steps 2609*c* or 2626 or the users selection of step 2620). Step 2630 may make use of composite generator 2632 to combine 2 or more images into one composite image set which the user or clinician selected, or the system automatically selected the multi-image composite for the user. For example, composite generator 2632 generates 2 or 3 image combinations. The composite generator 2632 creates composites based on the skill level and selected images. The Composite Creator/Generator is a system and process where 2 or 3 images are serially sectioned and the image slices alternately juxtaposed.

In step 2634, an interactivity is created for the user based on the user's self determined skill level, automatically determined skill level, input from a clinician, a group the user is a part of, and/or a preassigned interactivity protocol. The width of the sections may be varied with each image or be the same for both images or within the same image. The range of sectioning is between 1.5%-50 percent. (In some embodiments, to include a Slide bar sectioning 1-50%). In other embodiments, the Composite Creator/Generator can also be used to develop a sectioned substrate where individual images can be printed on the substrate or for display on a TUI prop. In the substrate printed version, the blocks may then be combined to create a 2 or 3-image composite, for example, which may have a fixed width. The printed image sections may be used for the same interactivities using printed templates and game pieces. In other embodiments, the composite generator includes a generator of a Tangible User Interface (TUI) Prop, which may be used to interact with an active surface displaying a sectioned portion of an image. The prop may used to virtually "pick-up" a digitally displayed image section so that it can be manipulated as a physical, tactile entity in TUI prop form; tactile interactions can be accomplished using a three dimensional printer (3-D printer) that prints three dimensional objects, such as puzzle pieces having sensors and/or bar coding on the puzzle pieces/interactivity pieces, so as to detect the user's placement of the puzzle pieces/interactivity pieces on an active surface. The width of the section can be varied and the prop displays the section in whatever size it is.

FIG. 26 shows a flowchart of a method 2600 of interacting with an interactivity. In step 2602, an interface for an interactivity is shown to the user. In step 2604, a determination is made of the type of interactivity to be presented to the user. For example, the user can be presented with a choice of types of interactivities, a clinician may choose an interactivity for the user, an automated choice may be made by the system based on input information and/or assessment information indicating a type of interactivity would be best for the user, the system can make recommendations to a clinician, the user may be part of a group and the type or interactivity may be based on the group that the user is part of, and/or a predefined protocol may be assigned to the user that has a preselected type of interactivity. For example, a determination may be made whether to present to the user with a FreePlay interactivity in which the user selects each interactivity prior to interacting with an interactivity, an automated sequence of interactivities in which each interactivity is chosen for the user (e.g., by a pre-established protocol), or a cognitive health interactivity may be selected in which each interactivity is selected for the purpose of diagnosing and/or treating a cognitive issue.

If it is determined in step 2604, to present a FreePlay mode to the user, method 2600 proceeds to step 2606, and in step 2606, the FreePlay mode begins.

If it is determined in step 2604, to present an automated sequence of interactivities to the user, method 2600 proceeds to step 2608, and in step 2608, the automated sequence of interactivities begins.

If it is determined in step 2604, to present a cognitive health mode to the user, method 2600 proceeds to step 2610, and in step 2610, the cognitive health interactivities begin. After step 2610, the method proceeds to step 2612, in which intra-activity data (or alpha data) is collected while the user interacts with the interactivities. Collecting the intra-activity data may include recording the total time for an interactivity, recording the time between each move, recording the errors in placements of pieces, recording the time each move takes, recording the time between the end of a move and the start of the next move, the time to the first move, i.e the reaction time, average reaction time, and recording decision patterns (e.g., what was the sequence the pieces were placed in the correct location based on color, placement order, location sequence? Was the sequence in which the pieces were placed based on the location of the image part in the image, such as by placing first the pieces at the edges in the correct locations and then placing the other pieces in their correct locations).

Next, in step 2614, post-activity data (or beta data) is collected, which may include collecting data that relates to the interactivity after the interactivity is finished. For example, a series of questions may be presented to the user about the interactivity, for the user to respond to. For example, the user may be asked to recall a word list associated with the interactivity, the user may be asked SQ2 questions (i.e., what color was the flower, the bird in the image looked most like which of the following birds), the user may be asked to recall 5-7 objects they previously identified in an image, or to recall 7-10 items present or descriptive of the image they worked with in the interactivities. The input for the word list recall may be received, via text, clicking on a list of words or clicking on words which and/or by voice/verbal response. The user may be asked to differentially provide a description of only one of the images in a stable or multi-stable image set, such as a list of the objects in one of the images or a scene caption, which may be provided by text and/or voice.

Next, in step 2616 biometric metric data (or gamma data) may be collected (which optionally may be collected by a third party). For example, the biometric data may include, an analysis of the user's voice, stressor inputs, an analysis of the user's handwriting (where the answers to some questions are received, via a hand written response, an analysis of the user's attempts to try to draw different types of figures, conducting a Single Channel EEG (e.g., while taking assessment or while performing another assessment, tracking eye movements while the user is performing the interactivity, mapping hand movements and/or other body movements while the user is performing the interactivity, and/or performing an fMRI while the user was performing an interactivity.

After or as part of steps 2612-2616, the data is analyzed by alpha assessments 2618, beta assessments 2620 and gamma assessments 2622.

Returning to step 2606 and 2608, after steps 2606 and 2608, the method proceeds to step 2618 for an alpha assessment.

Next data collector 2624 collects the results of alpha assessments 2618, beta assessments 2620, and/or gamma assessments 2622.

Then data analyzer 2626 analyzes the data from data collector 2624.

In step 2628, a determination is made whether there are signatures of any cognitive issues and/or cognitive strengths (for example, the system may be used for assessment whether a user has unusually good cognitive skills in one or more cognitive domains, i.e. people with Asperger's with generally excellent visual spatial abilities; or people with William's Syndrome with generally poor depth perception abilities).

The use of real-world image (pictures) allows for the development of image-cued word lists for recall assessments. The word list for Mem+ are image-cued, i.e., where the word list is derived from the images with which the user will perform interactivities for a period of time. The number of words which are image-cued can be varied as can the number of words used in the memory recall assessment. In one embodiment, 40% of the words in a word list will be image-cued. For example, a person can be tasked to remember 5 words, 3 of which are image-cued or the user may be tasked to remember 5 words where all 5 are image-cued. Similarly the user may be tasked to remember 7-10 words where all or only a portion of the words to be recalled are image-cued.

The stored user images are accessed based on the user's stored skill level. User data that is stored allows the user to pick up where the user left off in a previous session. In FreePlay mode, the user can continue with the same process or change options (change skill level, images, or interactivities). With training mode to advance their skill levels, other parameters can be changed. If thresholds are not met (e.g., number of tasks completed within a specified time; increase in the number of errors, total time increase), then game logic might offer a downgrade or encouragement or a hint at solving, or automatically adjust the skill level slightly to support continued use at the higher skill level/complexity but at its lower end rather than at the middle or higher end of a given skill level. For example, if the Skill Level is measured as follows: Difficult (Diff) can be broken into Diff0, Diff1, Diff2 ... Diff(n) where Diff(n) where "n" might be 10. If a user hits all thresholds for Diff(10) then the user advances similarly within the Difficulty level with additional and more complex tasks, higher thresholds to be met and other complexity modulation adjustments which can be made. If the difficulty level is Easy a similar design can be used for E0 where the levels are E0.1 . . . E0.n between E0 and E1. In some embodiments, the platform can adjust the complexity level with changes to sectioning, color and image content, number of pieces, size of the pieces. In one example, a person is given three puzzle sections for a given image and are tasked with reconstructing the whole image using the 3 pieces. Another person, with slightly better or capable cognitive status might be given the same image, the same three pieces initially for construction, but are then tasked with constructing the image using pieces of the same width but where there is now a mixture of 2-whole sections (2-W) and 1 section which has been divided in half (2-H). The progression might continue on the same day, or another day, with a simple training exercise (which also serves as an assessment) where the user is still working with a 3-part puzzle but the sections are now 1 whole section and 2 sections which are divided into halved parts (or quarter parts) fewer parts, larger parts $\Leftarrow$|E0|$\Rightarrow$ more puzzle parts, smaller puzzle parts, etc.

The $\alpha\beta\gamma$ Mem+ data collection and analyzer shown in step 2624 and step 2626 module once activated can capture and analyze data from other interactivities including intra-activity Word List Recall (T=0'); Delayed Recall (T=5'); Placement Error; Time/Move; Time between Moves, and post-activity Word List Extended Delay Recall (T=10-15') (text/voice) SQ2 Questions (spatial, quantitative, qualitative)(text/voice); Object Dimensional Descriptors (text/voice); DescribeIT! (text/voice); ObjectID/OIDm (label/voice), and utilize embedded, API or 3rd Party tools for voice analysis, handwriting analysis, stressors, eye tracking, single channel EEG, fMRI and other biometerics.

Mem+ Alpha may be assessed during the interactivities, traditional speed and accuracy measures are recorded during game play, along with individual time records of time taken per move, and time between moves (Mem+ Alpha), and movement mapping of users decisions in arriving at inter-activity solutions, including Placement Error Repeats and patterns. The word list recalls (T=0', 5' and 15'), together with other post-game assessments are used to acquire Mem+ Beta data and which together with Mem+ Alpha and/or with or without 3rd party Apps are combined to develop a user's Cognitive Profile and their Signatures (an over time measure).

Mem+ Gamma data can be used to further refine Cognitive Signatures, we plan to integrate third-party applications which can also be factored in for intra-activity measurements, including: single/multi-channel EEG, eye tracking, and stress level measures (HR, RR, BP, skin galvanic response, pupil dilation), among others which may evolve in their utility over time.

These metrics, together with intra-activity and post-activity assessments can be used to develop Cognitive Signatures which provide more comprehensive point-in-time and changes-over-time insights into the user's cognitive status.

If the Cognitive Health Sequence is used the User may choose for themselves and/or the Mem+ $\alpha\beta$ option can be activated for them by the system.

Mem+ $\alpha$ assessment data related to the interactivities collects speed and accuracy data as a default and is correlated to the use mode (Freeplay, Challenge, CognItive Health, etc.

A registered user can elect to review a detailed analyses of data at the end of a session and/or interactivity. The Mem+ data collector collects data related to the interactivities and assessments. The data can include the a Mem+ standard or the $\alpha\beta$ ($\gamma$) data. Data is captured continuously.

Data from $\alpha\beta$ is captured before, during and after $\alpha$ and $\beta$. Alpha data is collected during and after at least in terms of WL Recall, Dimensional Descriptors, Object ID/Object ID Memory and SQ2. In general, for those interactivities which require a user to respond verbally or with input, they can be characterized as beta, if there is a break in the interactivity, and which have accuracy and speed measures associated with them.

The $\alpha\beta\gamma$ data is analyzed. For a training protocol, the results of $\alpha\beta\gamma$ (intra-activity, post-activity and biometrics data, if available) can be used to determine if the user has reached thresholds for advancement in the complexity level. Those complexity level changes could include, but are not limited to: changing the sectioning strategy, changing the size of pieces to be matched or constructed, increasing the color and/or content number of objects in an image (e.g., bird on a branch with uniform color in the background can be less complicated than a bison on the road with the mountains in the background, and a speed limit road sign). For baseline assessment purposes, age and health normative data can be developed for a given set of interactivities, using the same images, at a given skill level. Using normative references, other assessment scales for high and low "outliers" can be developed individually and across a spectrum for cognition as a whole, allowing the platform the ability to scale skill levels based on user needs. Spectrum outlier ends might be represented by healthy, superior athletes and great thinkers with superior creative and/or critical skills; and, at the opposite end conditions-based outliers on a cognitive degradation scale (e.g., end-stage Alzheimer's disease). In some embodiments, there would be other scales where a skill may be superior in one group (visual-spatial for users with Aspergers) but where other domain-based skills are deficient. In some embodiments, for a person with Williams' syndrome visual spatial and depth perception can be compromised to greater/lesser extents but verbal language and reasoning are excellent. The system can be used to identify "global" markers which demonstrate global cognitive engagement (skills and processes), and domain-referenced skills (local). These efforts can be used to inform the development of a high-impact product group which can authentically tap into associative cognitive networks across multiple domains, assessing, reinforcing and/or improving on existing skills and processes, while at the same time identifying/addressing deficiencies—a streamlined, sensitive global assessment and/or interventional strategy.

The $\alpha\beta(\gamma)$ data is analyzed and used to generate the user's Cognitive Signature which is stored and displayed to the user The Mem+ standard is assessed. This includes speed and accuracy measures (total time, time per move, reaction time, error rate) which are embedded in the process of doing interactivities. The Mem+ standard can be stored and displayed.

In an embodiment, each of the steps of method 2600 is a distinct step. In another embodiment, although depicted as distinct steps in FIG. 26, step 2602-2632 may not be distinct steps. In other embodiments, method 2600 may not have all of the above steps and/or may have other steps in addition to or instead of those listed above. The steps of method 2600 may be performed in another order. Subsets of the steps listed above as part of method 2600 may be used to form their own method.

Alternatives and Extensions

In one embodiment of the platform, the images and/or image sets are gamified to generate manipulatable game pieces which the user uses in the various interactivities. Unlike many traditional types of puzzling interactivities, game pieces, e.g., manipulative elements generated for, by, and/or used with the platform do not contain fitted-shaped edges with fit specificity. Rather, manipulative elements are produced with only edges on each of its sides. This aspect requires that the user rely on visual and cognitive cues such as: image content, patterns, horizon lines/contiguities, color contiguity coherency as well as user knowledge and experience in identifying parts and reassembling puzzle pieces and/or other actions for engaging in other interactive manipulations.

In one embodiment using offline non-digital manipulatives, the sectioned puzzle pieces can be manufactured with a magnetic bud inserted into the sides of the image sections. This format can allow for kinesthetic awareness of the image sections top-bottom orientation to provide immediate feedback on the placement attempt relative to interactivities using a single image composition and/or a composite. For older adults with pacemakers where the use of magnets can be problematic as well as with other users, the platform's offline components can be comprised of a hybrid electronic gameboard using a TUI prop, which can include a timer element and/or be programmed based on the image sets using a QR and/or barcoding type of reader or other type of sensor which can identify individual game pieces/image sections and the targeted completed image and/or image set to evaluate proper placements and map user decision-making movements. In one embodiment, the digital gameboard interface may include embedded sensors lights and/or other visual and/or auditory cues to indicate proper as well as improper placement of individual pieces.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The platform allows users to engage in the interactivities in a self-directed fashion as well as facilitated, group play and competitive play. This is possible in part because of the nature of the interactivities, where turns can be taken, but also because the interactivities do not have to be time-dependent even though a timer may run in the background but which does not have to be visible to the user. The timer can also be used to limit a person's placement time during group play, where every turn is given a specified amount of time in which to complete a given turn/placement. Each of these variations is possible because interactivities are not time constrained and/or the solution or task completion does not have to be time-dependent.

These options give the platform significant advantages over other cognitive platforms; specifically, for group and facilitated interactions. Group interactions can provide workforce partners with an opportunity for competition and team-building on a larger scale looking at time to complete a series of tasks. The second type of group interaction can provide groups of individuals with opportunities for socialization as each can take a turn or work cooperatively on arriving at a puzzle solution as part of a group interactivity.

Facilitated interactions can also be overseen by a therapist during a treatment session and/or be provided by a caregiver as a means of socialization, but which can also be used to support cognitive training and/or treatment according to a set of protocols. Self-directed interactivities can be applied to the platform's multiple modes, including: Challenge, Freeplay and Mem+ mode—where the latter describes defined professional protocols developed for diagnostic, assessment, treatment and training purposes.

In one embodiment, the platform can be used for training purposes in Volume Information Processing mode and used in conjunction with a memory and/or attention assessment. In this interactive mode, the user is provided with sections extracted from an image and the user is then tasked to identify scenes or objects the user has observed in the task, identify color and identify the scenes of the object's spatial position within the image. Another interactive can be the presentation of multiple image sections from 10 or more images, and then tasking the user to identify parts of the whole from the collection of images in the MatchMe!-Banner interactivity.

In one embodiment, the platform can be configured to include an additional variable based on the presentation mode and the additional variable can be used to build skill level differences based on how the individual game pieces/interactive elements are presented to the user. The building skill level differences based on how the individual game pieces/interactive elements are presented to the user may include the presentation of all game pieces at the same time where the user is then required to sort through the sections. An alternative presentation format is where the user is tasked with working with a composite image set, and where the sections from only one of the component images are presented to the user for placement. Being given only section from one of multiple images of a composite image set can be used to vary the skill level complexity for the Jumble-Sort interactivity or at the start of any of the interactivities where one or more game pieces can be presented to the user as whole sections and/or parts of a whole section as half and quarter pieces for example.

In one embodiment, the composite image sets can be used in a view-only mode and presented to the user as a kind of slideshow with and/or without sequences as a mini-movie or video clip, depicting the manipulation of image sections in puzzle-type interactivities. The presentation mode can also include the component images as intact images and/or a sequence which can show the construction and/or deconstruction of one or more composite image sets from its component images and to its component images, respectively as well as labeling image objects and elements to support language recovery such as may be needed following a stroke, traumatic brain injury, concussion and/or with minimally conscious patients who may benefit from cognitively stimulating activities. The slideshow-styled presentation can be viewed on a digital device, including: computer, tablet, phone, TV, monitor/screen, IOT device, and/or other type of smart device. Parts of the component image or images can also include text labels placed on image elements as noted above. Text labels can be configured as part of a multi-language pack to make the platform user-friendly to non-native English speakers and/or to people who have developed language challenges associated with cognitive changes.

In one embodiment, a user may use the platform in an offline mode using view-only images in print format and/or through a digital device and at a different point in time and which use a different platform module or component. The platform's offline and device-based interoperability and overlapping component images and composite image sets allow for the translation of data from one device to another, from one mode to another, from one subset of interactivities to another throughout the user's engagement with the platform and its components for diagnostic, assessment, treatment, rehabilitation, maintenance and skills advancement purposes adjusting to the user's requirements and changes in their cognitive status.

This kind of versatility represents a significant advance over other platforms which are generally relegated to either an offline interactive or device-based interactive but with little or no crossover between the two, and are still focussed on using relatively simple stimuli with siloed skills. Further, many platforms rely on the use of neuropsychological assessments which were not designed as treatments. As such, the invention represents a paradigm shift in developing sensitive diagnostic and assessment protocols towards identifying cognitive biomarkers and implementing effective treatment protocols as well as learning modalities to advance user skills in one or more areas.

The platform is particularly well-suited to people who are recovering from a condition which impacts their cognition within a time frame and where functional recovery is possible, and where with early interventions within a system which is responsive to their changing needs in terms of linguistic challenges, fine motor control, limited mobility and/or need for facilitated use. These functional requirements either individually and/or together in part or all can be affected over time through both natural healing/recovery processes and/or interventional impacts with transitions to a different functional capacity and/or other types of improvements and/or compensatory changes including the ability to perform platform-associated tasks at the same time and/or at a higher skill level independently in a self-directed mode over time from previous facilitated use or VO mode.

In some embodiments, the platform can have applications for people following stroke, TBI, stress, depression, MCI, Alzheimer's disease and other dementias as well as other conditions. The platform can be used with people as inpatients and/or outpatients in rehabilitation settings, and in long-term care facilities where limited mobility and/or downtime between therapies and therapist interactions may occur, and where a self-directed or auto-launched, view-only mode type of interaction can provide an interventional therapy and/or supplemental treatment modality earlier in the recovery process.

In one embodiment using a TUI prop, the face of the prop can convey an image segment on its surface. When the TUI prop is brought into proximity of another TUI and/or separate electronic game board, and/or interfaces with a computer, tablet, and/or other smart device, the selected image is "transferred" onto the game board/screen. The TUI prop can then display another game piece using an automated process or on-demand process initiated by the user, instructing the TUI prop to display the next game piece. The sequence can be random and/or placement can be facilitated with composites by presenting the user with sections from only one of the component images for directed placements or a mixed grouping from two or more images.

With a mixed grouping, the platform can provide the user with a Jumble-Sort interactivity, which can include an assessment of the user's strategy and be varied in complexity with the number and size of the pieces to be sorted. The Jumble-Sort interactive can be applied to component images in the composites or to non-composited images but where two or more sectioned images are mixed together and the user is tasked to separate the image sections to belonging to Image #1, Image #2 and/or Image #3. In one embodiment of the Jumble-Sort interactivity, the system presents the user with a mixed grouping of one or more images which include both horizontal and vertical sectioning strategies. The user is tasked with separating not only the images but to separate these according to their sectioning strategy.

The Jumble-Sort interactivity can be used as a stand-alone interactivity and/or be combined with another interactivity and scored accordingly for correct and incorrect sorting, time and strategy, though the user may not have to be aware of the timed element.

The user can be provided with a reference image or be tasked with using other visual cues embedded in the images themselves, including: color, content and context to inform user decisions and/or be provided with a textual description of the target image.

The user's ability to complete a Jumble-Sort task, including sorting according to a set of rules, as well as other interactive tasks such as a Compose interactive, and/or changes in their ability to complete tasks including error rate and speed as well as other assessment components, whether the users are using individual images and/or composite images, can serve as an index of cognitive change. These measures can be used as a baseline and/or as a change metric. In one embodiment, a user's ability to perform interactivities can improve or regress. The changes in the user's ability to perform a task can regress from being able to complete tasks using composite images and component image sections, to not being able to sort individual component image sections along a spectrum of interactivities and/or other regressions and/or progressions.

Similarly, other users may have a starting point or baseline where the user is capable of performing single image tasks, such as composing individual image puzzles using sections, to not being able to assemble single image sections into a coherent image, with or without the use of a reference image. The placement of an individual along a cognitive capacity spectrum can also be assessed by changing the number and size of the sections. In one embodiment, the same image can be used but during an assessment that image is sectioned differently, varying the number and/or size of the "game" pieces/elements used in the interactivities.

In monitoring a user's progression and/or regression within a skill level or between skills levels, the platform uses a multiplicity of internally measured factors and which can be used to signal a change in the user's cognitive profile and corresponding changes in the level of interactivity for rehabilitation, treatment and/or skills development and/or learning purposes. The internal measures combined with external inputs can provide a cogent data steam reflecting multiple cognitive domain driven interactivities which can enhance our understanding of a user's cognitive status and change tracking. The platform can also integrate 3rd party sensors to directly input non-platform based factors to derive an enhanced cognitive profile. Changes of note can include: consistent/inconsistent time to complete tasks across multiple sessions; an increase/decrease in the amount of time it takes for the user to complete a task; change in a metric and/or sub-metric for one or more tasks; an increase/decrease in the number of misplacements; increase/decrease in the use of the reference image for on-demand display; Mem+ associated responses (Word List Recalls and SQ2); deliberate/erratic screen movements; response to altered sectioning strategy trial; response to altered size of to-be-placed pieces; and/or change in the number of pieces the user works with and/or the presentation, e.g., all at once or just one or more at a time; integration of other device data such as derived from a mobile phone tracking gait, other movements and other inputs such as forgotten password, passcode, increase in the number of misspelled words or consistent keystroke errors; changes in health status, prescription drug intake, food intake and sleep status; change in gaze and/or eye tracking across a composite; eye-tracking combined with ERP and EEG analysis, and/or fMRI data for sustained attention and engagement; body language cues, increase in frustration, and/or changes in mood. Some of the user-provided information is collected as part of a pre-session questionnaire which the user is prompted to fill out and can be used with the platform in any of its modes.

When a user presents changes in one or more factors with measured impacts on their cognitive status and/or skill acquisition abilities and/or learning capacity, the platform can adjust the user's skill level and evaluate how the user adapts to the new interactive regimen and/or protocol. Changes can include moving a user to a more advanced skill level and/or to a lower skill level, and/or switch to an alternate interactivity, and/or introduce an assessment protocol, and/or within the same skill level to improve training and/or treatment efficacy.

In one embodiment, the invention's assessments use a combination of user data for conducting both "point in time" and "changes over time" analyses. Additional analyses gathers data from multiple user groups in order to help define and identify potential biomarkers for further study. A biomarker for a given user group can be used to facilitate diagnoses and implement interventions earlier in a disease process. The identification of such non-invasive, cognitive biomarkers can potentially be used with the platform, and/or be used in conjunction with other biomarker identification methods such as Big Data analysis and then used in conjunction with the platform to assess the user's cognitive status as well as with other devices capable of measuring physiological and neuropsychological inputs, and or capturing data. As such, the platform can operate as a diagnostic tool and/or an assessment tool, and/or treatment tool and/or training tool to identify and monitor change and/or in an interventional treatment modality.

In some embodiments, audio recordings regardless of whether these are obtained from self-directed and/or facilitated assessments can be subjected to additional analyzes and compiled as part of a Big Data analysis of multiple users, and/or used to analyze biometrics' changes of the individual user over time using audio recordings of their voice. Voice change indicators, vocal indicators can provide insight into changes in the user's cognitive status as reflected in nuanced changes in vocal prosody and/or manifested in other communications, physical, physiological and/or behavioral changes, For example, "vocal prosody may include a composite of supra-segmental acoustic features of speech (e.g., in addition to the lexical, syntactic, and semantic content of signals). Primary features may include fundamental frequency (F0), which may be perceived as pitch and/or intensity, which may be perceived as loudness; and timing, which is perceived as speech rate, rhythm, and patterning in normal conversation. Related features include jitter and shimmer (cycle-to-cycle variation in frequency and intensity), energy distribution among formants, and cepstral features." (See: Cohen A S, Dinzeo T J, Donovan N J, Brown C E, Morrison S C. "Vocal acoustic analysis as a biometric indicator of information processing: Implications for neurological and psychiatric disorders." Psychiatry research.2015; 226(1):235-241.doi:10.1016/j.psychres.2014a.12.054.Schuller B, Batliner A, Steidl S, Seppi D. Recognising realistic emotions and affect in speech: State of the art and lessons learnt from the first challenge. Speech and Communication. 2010; 53(9-10): 10621087.)

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A system comprising:
a processor system including at least one processor; and
a memory system;
the memory system storing one or more instructions, which, when invoked, implement a method including at least
identifying, by the system, a ground position of at least an area of interest of an image by at least identifying a contiguity of the area of interest, the area interest including at least part of the image; the contiguity being a portion of at least the area of interest of the image, which when rendered is represented by a group of picture elements, where the group of picture elements are adjacent to one another and form a continuous image element, and the group of picture elements extends horizontally across most of the area of interest of the image;
determining, by the system, an ambiguity rating for at least a portion of the image, the ambiguity rating being a value that represents a degree to which the portion of the image has multiple interpretations; and
determining whether an element is associated with a ground position based on at least the ambiguity rating.

2. The system of claim 1, the method further comprising:
determining, by the system, a relationship between elements of the area of interest of the image by at least determining that an element is in a figure position of the area of interest of the image.

3. The system of claim 1, the image having multiple contiguities that have a hierarchical relationship,
the image having multiple contiguities that have a hierarchical relationship, and the method further comprising determining features of the area of interest of the image are based on at least the hierarchical relationship.

4. The system of claim 1, the method further comprising:
the identifying of the contiguity including at least identifying, by the system, multiple contiguities;
associating, by the system, a contrast with each contiguity; and
the identifying of the ground position being based at least on a relative contrast of the multiple contiguities with respect to one another.

5. The system of claim 1, the method further comprising:
identifying, by the system, a foreground element by at least identifying a disruption in the contiguity.

6. The system of claim 1, the method further comprising:
dividing the area of interest of the image into a background and a foreground, wherein the contiguity separates between the foreground and the background of the area of interest.

7. The system of claim 1, the method further comprising:
the identifying of the contiguity including at least determining an element to be within a ground position by at least identifying the element as being part of the contiguity.

8. The system of claim 1, the method further comprising:
identifying another contiguity; and
identifying an element as being in a figure position by at least identifying the element as being within another contiguity.

9. The system of claim 1, the method further comprising:
maneuvering a vehicle based at least on the identifying of the contiguity.

10. The system of claim 1,
the identifying of the ground position further including at least determining whether edges of the contiguity separate color sections of the image, and associating at least one of the color sections with a ground position and associating at least one of the color sections with a figure position.

11. The system of claim 1, further comprising
an artificial intelligence module; and
invoking, via the system, the artificial intelligence module to analyze the image, based at least on a training set upon which the artificial intelligence module was trained, and a value associated with a figure ground relationship.

12. The system of claim 11, the invoking of the artificial intelligence module to analyze the image including at least defining a relationship between objects.

13. The system of claim 1, further comprising
establishing a color map that maps color to a spatial relationship associated with the image; and
associating a foreground with the color map.

14. The system of claim 1, further comprising
establishing a color map that maps color to a spatial relationship associated with the image; and
associating a background with the color map.

15. The system of claim 1, the method further comprising:
cropping the image prior to the identifying of the ground position, the cropping of the image resulting in at least the area of interest being contained within a cropped portion of the image, wherein the identifying of the ground position is performed based at least on the area of interest that is contained within the cropped portion of the image.

16. The system of claim 1, the method further comprising:
searching for the image.

17. The system of claim 1, where the group of picture elements forms a patch of the image, which extends at least as much horizontally as vertically and which extends horizontally across most of the area of interest of the image.

18. A system comprising:
a processor system including at least one processor; and
a memory system;
the memory system storing one or more instructions, which, when invoked, implement a method including at least
identifying, by the system, a ground position of at least an area of interest of an image by at least identifying a contiguity of the area of interest, the area interest including at least part of the image;
the contiguity being a portion of at least the area of interest of the image, which when rendered is represented by a group of picture elements, where the group of picture elements are adjacent to one another and form a continuous image element, and the group of picture elements extends at least as much horizontally as vertically and that extends horizontally across most of the area of interest of the image; and
searching, by the system, for an image that will occupy a background position of a composite image by at least searching for an image with a contiguity.

19. A system comprising:
a processor system including at least one processor; and
a memory system;
the memory system storing one or more instructions, which, when invoked, implement a method including at least
identifying, by the system, a ground position of at least an area of interest of an image by at least identifying a contiguity of the area of interest, the area interest including at least part of the image;
the contiguity being a portion of the at least the area of interest of the image, which when rendered is represented by a group of picture elements, where the group of picture elements are adjacent to one another and form a continuous image element, and the group of picture elements extends at least as much horizontally as vertically and that extends horizontally across most of the area of interest of the image; and
determining, by the system, a saliency value, where the saliency value is a value that represents a quality of at least a single pixel relative to surrounding pixels that is associated with attracting a visual focus within a chosen area of the area of interest of the image;
determining an element to be a foreground element based on at least the saliency value
the saliency value being a value that increases and decreases with increases and decreases in contrast between, or within, elements of the chosen area of the area of interest of the image;
wherein saliency values on one side of a threshold being indicative of a higher degree of the contrast between, or within, the elements of the chosen area of the area of interest of the image,
the saliency values that are on the one side of the threshold being indicative of the element being part of a foreground, and the determining of the element to be a foreground element being based at least on the saliency value being on the one side of the threshold that is indicative of the higher degree of the contrast between, or within, the elements of the chosen area of the area of interest of the image; and
saliency values on another side of the threshold that is indicative of a lower degree of the contrast between, or within, the elements of the image, the saliency values that are on the other side of the threshold being indicative of the element being a background element, and the determining of the element to be the background element being based at least on the saliency value being on the other side of the threshold that is indicative of the lower degree of the contrast between, or within, the elements of the chosen area of the area of interest of the image.

20. A system comprising:
a processor system including at least one processor; and
a memory system;
the memory system storing one or more instructions, which, when invoked, implement a method including at least
identifying, by the system, a ground position of at least an area of interest of an image by at least identifying a contiguity of the area of interest, the area interest including at least part of the image;

the contiguity being a portion of the at least the area of interest of the image, which when rendered is represented by a group of picture elements, where the group of picture elements are adjacent to one another and form a continuous image element, and the group of picture elements extends at least as much horizontally as vertically and that extends horizontally across most of the area of interest of the image;

determining, by the system, a saliency value, the saliency value being a combination of other values that characterize at least a chosen area of the area of interest of the image, the saliency being a quality of a group of pixels or a quality for a single pixel relative to surrounding pixels within a chosen area of the area of interest of the image; and determining an element to be a foreground element based on at least the saliency value.

21. The system of claim 20, wherein the other values include a contrast between elements within at least the chosen area of the area of interest of the image.

22. The system of claim 20, wherein the other values include a value representing how many contiguities are in at least the chosen area of the area of interest of the image.

23. The system of claim 20, wherein the other values include a value representing how many regions of different color are present in at least the chosen area within the area of interest of the image, where each region of a particular color has elements that are within one or more threshold values of a color value characterizing the particular color.

24. The system of claim 20, wherein the other values include a value representing a distribution of blocks of color within at least the chosen area of the area of interest.

25. The system of claim 20, wherein the other values include a value representing a comparison of at least
   (1) a value representing how many contiguities are in at least the chosen area of the area of the image and
   (2) a value representing how many regions of different colors are present in at least the chosen area of the area of the image, where each region of a particular color has elements that are within one or more threshold values of a color value characterizing the particular color.

26. A system comprising:
a processor system including at least one processor; and
a memory system;
the memory system storing one or more instructions, which, when invoked, implement a method including at least
identifying, by the system, a ground position of at least an area of interest of an image by at least identifying a contiguity of the area of interest, the area interest including at least part of the image;
the contiguity being a portion of at least the area of interest of the image, which when rendered is represented by a group of picture elements, where the group of picture elements are adjacent to one another and form a continuous image element, and the group of picture elements extends at least as much horizontally as vertically and that extends horizontally across most of the area of interest of the image;
the identifying including at least producing, by the system, a binary image to identify the contiguity, wherein pixels of the binary image have one of two values, and the pixels of the contiguity have the same pixel value; and
identifying, by the system, a foreground region based at least in part on the binary image.

27. The system of claim 26, the image being a still image.

28. The system of claim 26, the method not requiring the image to have portions associated with movement.

29. A system comprising:
a processor system including at least one processor; and
a memory system;
the memory system storing one or more instructions, which, when invoked, implement a method including at least
identifying, by the system, a ground position of at least an area of interest of a first image by at least identifying a contiguity of the area of interest, the area interest including at least part of the first image; and
the contiguity being a portion of at least the area of interest of the first image, which when rendered is represented by a group of picture elements, where the group of picture elements are adjacent to one another and form a continuous image element, and the group of picture elements extends at least as much horizontally as vertically and that extends horizontally across most of the area of interest of the first image;
searching, by the system, for a second image with a specified contiguity characteristic;
determining, by the system, a relative hierarchy between the first image and the second image found by the searching, the relative hierarchy being based at least on a value assigned to the contiguity characteristic; and
selecting, by the system, the second image based at least on the relative hierarchy; and
combining the first image and the second image into a composite image.

30. A system comprising:
a processor system including at least one processor; and
a memory system;
the memory system storing one or more instructions, which, when invoked, implement a method including at least
identifying, by the system, a ground position of at least an area of interest of an image by at least identifying a contiguity of the area of interest, the area interest including at least part of the image;
the contiguity being a portion of at least the area of interest of the image, which when rendered is represented by a group of picture elements, where the group of picture elements are adjacent to one another and form a continuous image element, and the group of picture elements extends at least as much horizontally as vertically and that extends horizontally across most of the area of interest of the image, the image being a first image; and
categorizing one or more images based at least on contiguity characteristics.

31. A system comprising:
a processor system including at least one processor; and
a memory system;
the memory system storing one or more instructions, which when invoked, implement a method including at least
identifying, by the system, a figure position of an area of interest of an image by at least identifying a contiguity of at least the area of interest of the image, the area of interest of the image including at least part of the image;
the contiguity being at least a portion of the area of interest of the image, which when rendered is represented by a group of picture elements that are adjacent to one another and that form a continuous image element that extends at least as much horizontally as vertically and that extends horizontally across most of the area of interest of the image;

determining, by the system, an ambiguity rating for at least a portion of the image, the ambiguity rating being a value that represents a degree to which the portion of the image has multiple interpretations; and determining whether an element is associated with a ground position based at least on the ambiguity rating.

32. A method comprising:

identifying, by a system, a ground position of an area of interest of an image by at least identifying a contiguity of at least the area of interest of the image, the system including at least a processor system including at least one processor, and a memory system that stores one or more instructions, which when invoked cause the system to implement the method; and the contiguity being at least a portion of the area of interest of the image, which when rendered is represented by a group of picture elements that are adjacent to one another and that form a continuous image element that extends horizontally across most of the area of interest of the image;

determining, by the system, an ambiguity rating for at least a portion of the image, the ambiguity rating being a value that represents a degree to which the portion of the image has multiple interpretations; and determining whether an element is associated with a ground position based at least on the ambiguity rating.

33. A system comprising:

a processor system including at least one processor; and a memory system;

the memory system storing one or more instructions, which, when invoked, implement a method including at least identifying, by the system, a ground position of at least an area of interest of an image by at least identifying a contiguity of the area of interest, the area interest including at least part of the image;

the contiguity being a portion of at least the area of interest of the image, which when rendered is represented by a group of picture elements, where the group of picture elements are adjacent to one another and form a continuous image element, and the group of picture elements extends horizontally across most of the area of interest of the image;

determining, by the system, a saliency value, where the saliency value is a value that represents a quality of at least a single pixel relative to surrounding pixels, the quality being associated with attracting a visual focus within a chosen area of the area of interest of the image, where the quality is based at least on factors other than just geometric factors; and determining an element to be a foreground element based on at least the saliency value.

* * * * *